United States Patent
Steingart et al.

(10) Patent No.: US 8,359,114 B2
(45) Date of Patent: Jan. 22, 2013

(54) HAPTICALLY ENABLED DENTAL MODELING SYSTEM

(75) Inventors: Bob Steingart, Wellesley, MA (US); Curt Rawley, Windham, NH (US); Joe Wisnewski, Pelham, NH (US); Dave Girard, Chelmsford, MA (US); Vincent M. Hammer, Milton, VT (US); Scott Davidson, Jamaica Plain, MA (US); Brandon Itkowitz, Sunnyvale, CA (US); Brian Cooper, Foxboro, MA (US); Yakov Epelbaum, Woburn, MA (US); Elaine Chen, Arlington, MA (US); Abbe J. Cohen, Somerville, MA (US); Terry Lindgren, Acton, MA (US); Mike Tabaczynski, Lexington, MA (US); David Tzu-Wei Chen, Wrentham, MA (US); Venkatraghavan Gourishankar, Woburn, MA (US)

(73) Assignee: DentsAble, Inc., Wilmington, MA (US)

( * ) Notice: Subject to any disclaimer, the term of this patent is extended or adjusted under 35 U.S.C. 154(b) by 691 days.

(21) Appl. No.: 12/321,766

(22) Filed: Jan. 23, 2009

(65) Prior Publication Data

US 2009/0248184 A1 Oct. 1, 2009

Related U.S. Application Data

(63) Continuation-in-part of application No. 11/998,457, filed on Nov. 28, 2007.

(60) Provisional application No. 60/861,589, filed on Nov. 28, 2006, provisional application No. 61/062,275, filed on Jan. 23, 2008.

(51) Int. Cl.
G06F 19/00 (2011.01)

(52) U.S. Cl. .......................................... 700/98; 700/182

(58) Field of Classification Search .................... 700/98, 700/182
See application file for complete search history.

(56) References Cited

U.S. PATENT DOCUMENTS

| | | | |
|---|---|---|---|
| 5,257,203 A | 10/1993 | Riley et al. |
| 5,417,572 A | 5/1995 | Kawai et al. |
| 5,587,912 A | 12/1996 | Andersson et al. |
| 5,850,229 A | 12/1998 | Edelsbrunner et al. |
| 5,880,962 A | 3/1999 | Andersson et al. |
| 5,975,893 A | 11/1999 | Chishti et al. |
| 6,049,743 A | 4/2000 | Baba |
| 6,210,162 B1 | 4/2001 | Chishti et al. |

(Continued)

FOREIGN PATENT DOCUMENTS

| EP | 1561433 A1 | 8/2005 |
|---|---|---|
| EP | 1662414 | 5/2006 |

(Continued)

OTHER PUBLICATIONS

Hideki, Aita et al., "Application of Three-dimensional Haptic Interface in Dentistry", Prosthodont Res Pract 2 : 88-93, 2003.*

(Continued)

*Primary Examiner* — Carlos Ortiz Rodriguez
(74) *Attorney, Agent, or Firm* — Choate Hall & Stewart LLP

(57) ABSTRACT

The invention provides a digital dentistry system that utilizes a haptic interface and features a computer-based design application configured to allow the intuitive construction of irregular, amorphous three-dimensional structures typically seen in dental restorations, utilizing, where appropriate, the design skills of a user. In certain embodiments, the system provides a comprehensive digital solution for dental labs in the business of creating dental restorations such as partial frameworks, crowns, copings, bridge frameworks, implants and the like, with a sense of touch provided by a haptic interface device.

57 Claims, 38 Drawing Sheets

U.S. PATENT DOCUMENTS

| | | | |
|---|---|---|---|
| 6,214,285 B1 | 4/2001 | Rubbert et al. |
| 6,217,325 B1 | 4/2001 | Chishti et al. |
| 6,227,850 B1 | 5/2001 | Chishti et al. |
| 6,227,851 B1 | 5/2001 | Chishti et al. |
| 6,250,918 B1 | 6/2001 | Sachdeva et al. |
| 6,299,440 B1 | 10/2001 | Phan et al. |
| 6,309,215 B1 | 10/2001 | Phan et al. |
| 6,315,553 B1 | 11/2001 | Sachdeva et al. |
| 6,318,994 B1 | 11/2001 | Chishti et al. |
| 6,350,120 B1 | 2/2002 | Sachdeva et al. |
| 6,355,048 B1 | 3/2002 | Hong et al. |
| 6,371,761 B1 | 4/2002 | Cheang et al. |
| 6,377,865 B1 | 4/2002 | Edelsbrunner et al. |
| D457,638 S | 5/2002 | Alstad et al. |
| 6,386,864 B1 | 5/2002 | Kuo |
| 6,386,878 B1 | 5/2002 | Pavlovskaia et al. |
| 6,390,812 B1 | 5/2002 | Chishti et al. |
| 6,394,801 B2 | 5/2002 | Chishti et al. |
| 6,398,548 B1 | 6/2002 | Muhammad et al. |
| 6,406,292 B1 | 6/2002 | Chishti et al. |
| 6,409,504 B1 | 6/2002 | Jones et al. |
| 6,421,048 B1 | 7/2002 | Shih et al. |
| 6,450,807 B1 | 9/2002 | Chishti et al. |
| 6,454,565 B2 | 9/2002 | Phan et al. |
| 6,457,972 B1 | 10/2002 | Chishti et al. |
| 6,463,344 B1 | 10/2002 | Pavloskaia et al. |
| 6,464,496 B1 | 10/2002 | Sachdeva et al. |
| 6,471,511 B1 | 10/2002 | Chishti et al. |
| 6,485,298 B2 | 11/2002 | Chishti et al. |
| 6,488,499 B1 | 12/2002 | Miller |
| 6,497,574 B1 | 12/2002 | Miller |
| 6,499,997 B2 | 12/2002 | Chishti et al. |
| 6,512,994 B1 | 1/2003 | Sachdeva |
| 6,514,074 B1 | 2/2003 | Chishti et al. |
| 6,524,101 B1 | 2/2003 | Phan et al. |
| 6,532,299 B1 | 3/2003 | Sachdeva et al. |
| 6,540,512 B1 | 4/2003 | Sachdeva et al. |
| 6,554,611 B2 | 4/2003 | Chishti et al. |
| 6,572,372 B1 | 6/2003 | Phan et al. |
| 6,573,998 B2 | 6/2003 | Cohen-Sabban |
| 6,579,095 B2 | 6/2003 | Marshall et al. |
| 6,582,227 B2 | 6/2003 | Phan et al. |
| 6,582,229 B1 | 6/2003 | Miller et al. |
| 6,602,070 B2 | 8/2003 | Miller et al. |
| 6,607,382 B1 | 8/2003 | Kuo et al. |
| 6,612,143 B1 | 9/2003 | Butscher et al. |
| 6,621,491 B1 | 9/2003 | Baumrind et al. |
| 6,626,666 B2 | 9/2003 | Chishti et al. |
| 6,629,840 B2 | 10/2003 | Chishti et al. |
| 6,632,089 B2 | 10/2003 | Rubbert et al. |
| 6,633,789 B1 | 10/2003 | Nikolskiy et al. |
| 6,665,570 B2 | 12/2003 | Pavloskaia et al. |
| 6,682,346 B2 | 1/2004 | Chishti et al. |
| 6,685,469 B2 | 2/2004 | Chishti et al. |
| 6,685,470 B2 | 2/2004 | Chishti et al. |
| 6,688,885 B1 | 2/2004 | Sachdeva et al. |
| 6,688,886 B2 | 2/2004 | Hughes et al. |
| 6,691,764 B2 | 2/2004 | Embert et al. |
| 6,699,037 B2 | 3/2004 | Chishti et al. |
| 6,705,861 B2 | 3/2004 | Chishti et al. |
| 6,705,863 B2 | 3/2004 | Phan et al. |
| 6,722,880 B2 | 4/2004 | Chishti et al. |
| 6,726,478 B1 | 4/2004 | Isiderio et al. |
| 6,728,423 B1 | 4/2004 | Rubbert et al. |
| 6,729,876 B2 | 5/2004 | Chishti et al. |
| 6,732,558 B2 | 5/2004 | Butscher et al. |
| 6,736,638 B1 | 5/2004 | Sachdeva et al. |
| 6,738,508 B1 | 5/2004 | Rubbert et al. |
| 6,744,914 B1 | 6/2004 | Rubbert et al. |
| 6,744,932 B1 | 6/2004 | Rubbert et al. |
| 6,755,064 B2 | 6/2004 | Butscher et al. |
| 6,761,560 B2 | 7/2004 | Miller |
| 6,767,208 B2 | 7/2004 | Kaza |
| 6,771,809 B1 | 8/2004 | Rubbert et al. |
| 6,783,360 B2 | 8/2004 | Chishti |
| 6,783,604 B2 | 8/2004 | Tricca |
| 6,786,721 B2 | 9/2004 | Chishti et al. |
| 6,790,035 B2 | 9/2004 | Tricca et al. |
| 6,802,713 B1 | 10/2004 | Chishti et al. |
| 6,814,574 B2 | 11/2004 | Abolfathi et al. |
| 6,830,450 B2 | 12/2004 | Knopp et al. |
| 6,851,949 B1 | 2/2005 | Rubbert et al. |
| 6,854,973 B2 | 2/2005 | Butcher et al. |
| 6,860,132 B2 | 3/2005 | Butscher et al. |
| 6,885,464 B1 | 4/2005 | Pfeiffer et al. |
| 6,887,078 B2 | 5/2005 | Perot |
| 6,905,337 B1 | 6/2005 | Sachdeva |
| 6,918,761 B2 | 7/2005 | Sachdeva et al. |
| 6,947,038 B1 | 9/2005 | Anh et al. |
| 6,948,931 B2 | 9/2005 | Chishti et al. |
| 6,948,936 B2 | 9/2005 | Miller et al. |
| 6,964,564 B2 | 11/2005 | Phan et al. |
| 6,971,873 B2 | 12/2005 | Sachdeva et al. |
| 6,976,627 B1 | 12/2005 | Culp et al. |
| 6,979,196 B2 | 12/2005 | Nikolskiy et al. |
| 7,003,472 B2 | 2/2006 | Sachdeva |
| 7,004,754 B2 | 2/2006 | Kaufmann et al. |
| 7,010,150 B1 | 3/2006 | Pfeiffer et al. |
| 7,013,191 B2 | 3/2006 | Rubbert et al. |
| 7,027,642 B2 | 4/2006 | Rubbert et al. |
| 7,029,275 B2 | 4/2006 | Rubbert et al. |
| 7,035,702 B2 | 4/2006 | Jelonek et al. |
| 7,037,108 B2 | 5/2006 | Chishti et al. |
| 7,037,111 B2 | 5/2006 | Miller |
| 7,040,896 B2 | 5/2006 | Pavlovskaia et al. |
| 7,056,115 B2 | 6/2006 | Phan et al. |
| 7,058,213 B2 | 6/2006 | Rubbert et al. |
| 7,059,850 B1 | 6/2006 | Phan et al. |
| 7,063,532 B1 | 6/2006 | Jones et al. |
| 7,063,533 B2 | 6/2006 | Phan et al. |
| 7,068,825 B2 | 6/2006 | Rubbert et al. |
| 7,068,836 B1 | 6/2006 | Rubbert et al. |
| 7,074,038 B1 | 7/2006 | Miller |
| 7,076,980 B2 | 7/2006 | Butscher et al. |
| 7,077,647 B2 | 7/2006 | Choi et al. |
| 7,080,979 B2 | 7/2006 | Rubbert et al. |
| 7,092,784 B1 | 8/2006 | Simkins |
| 7,108,508 B2 | 9/2006 | Hedge et al. |
| 7,110,594 B2 | 9/2006 | Jones et al. |
| 7,112,065 B2 | 9/2006 | Kopelman et al. |
| 7,121,825 B2 | 10/2006 | Chishti et al. |
| 7,123,767 B2 | 10/2006 | Jones et al. |
| 7,125,248 B2 | 10/2006 | Phan et al. |
| 7,133,042 B2 | 11/2006 | Anh et al. |
| 7,134,874 B2 | 11/2006 | Chishti et al. |
| 7,140,877 B2 | 11/2006 | Kaza |
| 7,156,655 B2 | 1/2007 | Sachdeva et al. |
| 7,156,661 B2 | 1/2007 | Choi et al. |
| 7,160,110 B2 | 1/2007 | Imgrund et al. |
| 7,167,584 B2 | 1/2007 | Guern |
| 7,172,417 B2 | 2/2007 | Sporbert et al. |
| 7,192,275 B2 | 3/2007 | Miller |
| 7,197,179 B2 | 3/2007 | Rubbert et al. |
| 7,200,642 B2 | 4/2007 | Hultgren et al. |
| 7,201,576 B2 | 4/2007 | Tricca et al. |
| 7,215,803 B2 | 5/2007 | Marshall |
| 7,215,810 B2 | 5/2007 | Kaufmann et al. |
| 7,220,122 B2 | 5/2007 | Chishti |
| 7,228,191 B2 | 6/2007 | Hofmeister et al. |
| 7,234,937 B2 | 6/2007 | Sachdeva et al. |
| 7,241,142 B2 | 7/2007 | Abolfathi et al. |
| 7,245,750 B2 | 7/2007 | Hultgren et al. |
| 7,245,977 B1 | 7/2007 | Simkins |
| 7,247,021 B2 | 7/2007 | Jones et al. |
| 7,252,509 B2 | 8/2007 | Sachdeva |
| 7,255,561 B2 | 8/2007 | Tricca et al. |
| 7,261,533 B2 | 8/2007 | Wrosz et al. |
| 7,273,367 B2 | 9/2007 | Hughes et al. |
| 7,283,891 B2 | 10/2007 | Butscher et al. |
| 7,293,988 B2 | 11/2007 | Wen |
| 7,296,996 B2 | 11/2007 | Sachdeva et al. |
| 7,305,110 B2 | 12/2007 | Rubbert et al. |
| 7,305,121 B2 | 12/2007 | Kaufmann et al. |
| 7,306,152 B2 | 12/2007 | Culp et al. |
| 7,309,230 B2 | 12/2007 | Wen |
| 7,320,592 B2 | 1/2008 | Chishti et al. |
| 7,326,051 B2 | 2/2008 | Miller |

| Patent No. | Date | Name |
|---|---|---|
| 7,331,783 B2 | 2/2008 | Chishti et al. |
| 7,335,024 B2 | 2/2008 | Wen |
| 7,347,686 B2 | 3/2008 | Marshall |
| 7,349,130 B2 | 3/2008 | Vadnais et al. |
| 7,354,270 B2 | 4/2008 | Abolfathi et al. |
| 7,357,634 B2 | 4/2008 | Knopp |
| 7,357,636 B2 | 4/2008 | Hedge et al. |
| 7,361,017 B2 | 4/2008 | Sachdeva et al. |
| 7,361,018 B2 | 4/2008 | Imgrund et al. |
| 7,361,020 B2 | 4/2008 | Abolfathi et al. |
| 7,373,286 B2 | 5/2008 | Nikolskiy et al. |
| 7,377,778 B2 | 5/2008 | Chishti et al. |
| 7,379,584 B2 | 5/2008 | Rubbert et al. |
| 7,383,198 B1 | 6/2008 | Sepe |
| 7,384,266 B2 | 6/2008 | Wen |
| 7,387,511 B2 | 6/2008 | Marshall |
| 7,422,430 B2 | 9/2008 | Sachdeva et al. |
| 7,428,481 B2 | 9/2008 | Nikolskiy et al. |
| 7,433,810 B2 | 10/2008 | Pavloskaia et al. |
| 7,435,083 B2 | 10/2008 | Chishti et al. |
| 7,435,084 B2 | 10/2008 | Liu et al. |
| 7,442,040 B2 | 10/2008 | Kuo |
| 7,442,041 B2 | 10/2008 | Imgrund et al. |
| 7,448,514 B2 | 11/2008 | Wen |
| 7,452,207 B2 | 11/2008 | Miller et al. |
| 7,458,812 B2 | 12/2008 | Sporbert et al. |
| 7,461,005 B2 | 12/2008 | Sachdeva |
| 7,463,942 B2 | 12/2008 | O'Brien et al. |
| 7,471,821 B2 | 12/2008 | Rubbert et al. |
| 7,472,789 B2 | 1/2009 | Wu et al. |
| 7,474,307 B2 | 1/2009 | Chishti et al. |
| 7,474,932 B2 | 1/2009 | Geng |
| 7,476,100 B2 | 1/2009 | Kuo |
| 7,481,121 B1 | 1/2009 | Cao |
| 7,481,647 B2 | 1/2009 | Sambu et al. |
| 7,530,811 B2 | 5/2009 | Kaufmann et al. |
| 7,543,511 B2 | 6/2009 | Kimura et al. |
| 7,553,157 B2 | 6/2009 | Abolfathi et al. |
| 7,572,121 B2 | 8/2009 | Wrosz et al. |
| 7,578,673 B2 | 8/2009 | Wen et al. |
| 7,578,674 B2 | 8/2009 | Chishti et al. |
| 7,580,846 B2 | 8/2009 | Chishti et al. |
| 7,585,172 B2 | 9/2009 | Rubbert et al. |
| 7,590,462 B2 | 9/2009 | Rubbert et al. |
| 7,600,999 B2 | 10/2009 | Knopp |
| 7,604,181 B2 | 10/2009 | Culp et al. |
| 7,609,875 B2 | 10/2009 | Liu et al. |
| 7,611,058 B2 | 11/2009 | Culp et al. |
| 7,637,740 B2 | 12/2009 | Knopp |
| 7,641,473 B2 | 1/2010 | Sporbert et al. |
| 7,641,828 B2 | 1/2010 | DeSimone et al. |
| 7,648,360 B2 | 1/2010 | Kuo |
| 7,658,610 B2 | 2/2010 | Knopp |
| 2002/0013636 A1 | 1/2002 | O'Brien et al. |
| 2002/0089500 A1 | 7/2002 | Jennings et al. |
| 2002/0110786 A1 | 8/2002 | Dillier |
| 2003/0207227 A1 | 11/2003 | Abolfathi |
| 2005/0089822 A1 | 4/2005 | Geng |
| 2005/0128211 A1 | 6/2005 | Berger et al. |
| 2006/0040236 A1 | 2/2006 | Schmitt |
| 2006/0105294 A1 | 5/2006 | Burger et al. |
| 2006/0115795 A1 | 6/2006 | Marshall et al. |
| 2006/0275736 A1 | 12/2006 | Wen et al. |
| 2007/0190481 A1 | 8/2007 | Schmitt |
| 2007/0190492 A1 | 8/2007 | Schmitt |

FOREIGN PATENT DOCUMENTS

| | | |
|---|---|---|
| EP | 1997453 | 12/2008 |
| WO | WO-2006009747 A1 | 1/2006 |
| WO | WO-2008066891 | 6/2008 |

OTHER PUBLICATIONS

Kim et al., "Haptic interaction and volume modeling techniques for realistic dental simulation", Springer-Verlag, Jan. 2006.*
International Search Report and Written Opinion for PCT/US2007/024576, dated May 20, 2008, 4 pages.
International Search Report and Written Opinion for PCT/US2009/031883, dated Jun. 8, 2009, 11 pages.

* cited by examiner

HAPTICALLY ENABLED DENTAL MODELING SYSTEM

RELATED APPLICATIONS

The instant application is a continuation-in-part of U.S. patent application Ser. No. 11/998,457, filed Nov. 28, 2007, which is an application claiming the benefit under 35 U.S.C. 119(e) of U.S. Provisional Patent Application No. 60/861,589, filed Nov. 28, 2006, the texts of which are incorporated by reference herein, in their entirety; the instant application is also an application claiming the benefit under 35 U.S.C. 119(e) of U.S. Provisional Patent Application No. 61/062,275, filed Jan. 23, 2008, the text of which is incorporated by reference herein, in its entirety.

FIELD OF THE INVENTION

This invention relates generally to systems and tools for dental restoration. More particularly, in certain embodiments, the invention relates to a computer-based design application configured to allow the intuitive construction by a user of irregular, amorphous three-dimensional structures typically seen in dental restorations.

BACKGROUND OF THE INVENTION

The U.S. dental restoration industry (crowns, bridges, partial and full dentures) is a very large market, currently generating more than $7 billion in revenue (over $20 billion worldwide). Despite its large size, the design and production of dental restorations is characterized mainly by low-tech, manual processes performed on a small scale by geographically dispersed and fragmented labs.

Traditional dental laboratory methods are labor-intensive, generations old, and require a great deal of manual dexterity and, for many assignments, an artistic skill. The traditional process by which a crown or bridge is fabricated (i.e., create wax replica, invest wax in stone, melt out wax, replace with molten metal, remove from stone, add porcelain or other materials) was first developed by the Egyptians over 3,000 years ago. Many labs have only very basic capital equipment, relying only on simple mixers, ovens and their years of training and skill in the design of dental restorations.

A number of digital dentistry manufacturers have introduced systems to help laboratories design restorations in a digital context in the hope of producing highly accurate restorations more rapidly and efficiently, improving the lab throughput, profitability and quality. Many vendors are vying for market share, but none of the currently available systems offer a solution that is easily adopted by dental lab technicians. Penetration is low, with the number of restorations made digitally still less than 10% of the total.

Some of the key hurdles to widespread adoption of digitized solutions in restorative dentistry are the difficulty that most technicians experience in utilizing traditional computer interfaces for mechanical design, and the lack of intuitive tools to modify digital models of restorations in ways that allow a technician to draw on their experience and expertise. The current industry offerings require technicians to develop proficiency in abstraction laden, complex design programs far different from their experience and training. Furthermore, these systems are ill-equipped to deal with the highly organic nature of designing dental prosthetics.

There is a need for a transparent, easy to use, and easy to learn digital dentistry system that dental professionals will embrace. The digital dentistry system must be able to generate highly organic shapes and allow the users to easily and intuitively modify these shapes, just like they do by hand on a wax model.

SUMMARY

Embodiments of the invention provide a digital dentistry system that utilizes a haptic interface and features a computer-based design application configured to allow the intuitive construction of irregular, amorphous three-dimensional structures typically seen in dental restorations. Other embodiments provide virtual tools for modifying a variety of three-dimensional virtual representations of a restoration automatically, semi-manually, or manually, allowing input and adjustment from a skilled technician.

In certain embodiments, the system provides a comprehensive digital solution for dental labs in the business of creating dental restorations such as partial frameworks, crowns, copings, bridge frameworks, implants and the like, with a sense of touch provided by a haptic interface device such as the SensAble PHANTOM™ haptic device manufactured by SensAble Technologies, Inc., of Woburn, Mass.

In certain embodiments, the dental lab system provides an integrated solution for dental restorations including partial frameworks, crowns, copings, bridge frameworks, implants and the like. For example, in one embodiment, the system includes an optical 3D scanner, 3D design software, haptic (force-feedback interface device), system integration software, networking and computer hardware, and, in some packaged configurations, a rapid prototyping (RP) device or milling machine for fabrication of dental restorations. In other configurations, the dental restorations may be fabricated at a production center and the restorations may be shipped to the dental labs for final fit and finish.

In general, in one aspect, the invention includes a system for building a virtual wax object corresponding to a three-dimensional dental restoration. The system includes a design application in communication with the user interface. The design application includes one or more virtual wax-up tools configured to build a virtual wax object corresponding to a three-dimensional dental restoration onto a virtual refractory model according to user input via the user interface.

In various embodiments, the virtual wax object is predominately voxel based, and has a boundary representation geometry near a margin line. The one or more virtual wax-up tools may include one or more members selected from the group consisting of a virtual mesh tool, a virtual ridge tool, a virtual clasp tool, a virtual finish line tool, and a virtual lingual collar tool. The one or more virtual wax-up tools may include a virtual mesh tool; the virtual mesh tool may build a three-dimensional patterned mesh portion of the virtual wax object within an arbitrary, user-identified region of a surface of the virtual refractory model with minimal distortion. The virtual mesh tool may split a user-defined closed loop curve fit to the surface of the virtual refractory model into four boundary curves within which a NURBS patch is fit and may further build a spacer volume of a user-defined thickness, along with the three-dimensional patterned mesh portion.

In various embodiments, the one or more virtual wax up tools includes a virtual ridge tool. The virtual ridge tool may build a long extruded wax pattern with a profile and end taper characteristic suitable for creation of clasps and finish lines around the mesh areas in a partial framework. The virtual ridge tool may accept as input one or more guide curves, one or more cross-sectional profiles, and one or more end taper parameters determined by the user. The one or more guide curves, one or more cross-sectional profiles, and one or more end taper parameters may be selected by the user from a system-wide preferences database. The user interface may be a haptic interface device configured to provide force feedback to a user and the virtual ridge tool may include one or more haptic aids delivered to the user via the haptic interface device to assist the user in creating and/or editing the one or more guide curves, the one or more cross-sectional profiles, or both. The one or more haptic aids may include a haptic snap corresponding to each of a plurality of points of a guide curve, facilitating selection of one or more points of the guide curve by the user for adjustment. The one or more haptic aids may include a two-dimensional restriction plane, facilitating selection and adjustment of profile points and/or handles of the one or more cross-sectional profiles.

In various embodiments, the one or more virtual wax up tools includes a virtual clasp tool. The virtual clasp tool may build a simple ring clasp, a J-shaped clasp, or a T-shaped clasp based on one or more user-selected guide curves, profiles, and parameters defining end taper conditions. The one or more virtual wax up tools may include a virtual finish line tool or a virtual lingual collar tool. The user interface may be a haptic interface device configured to provide force feedback to a user and the haptic interface device may include a stylus interface. The user interface may be a haptic interface device configured to provide force feedback to a user and the haptic interface device may have at least six degrees of freedom. The dental restoration may be a partial framework, crown and bridge, implant, veneer, night guard, bite splint, or orthodonture, for example.

The description of elements of the embodiments of other aspects of the invention can be applied to this aspect of the invention as well.

In general, in another aspect, the invention includes a method for designing a three-dimensional dental restoration. The method includes creating an initial 3D computer model from a scan of a dental stone made from an impression of a patient's mouth, or, alternatively, creating the initial 3D computer model from a direct scan of the patient's mouth, adding virtual block-out wax to the initial 3D computer model automatically, manually, or semi-automatically, and joining the initial 3D computer model and the added virtual block-out wax (e.g., via a union operation), thereby forming a virtual refractory model. The method further includes adding virtual design wax onto the virtual refractory model to define a final 3D computer model of the dental restoration and, optionally, manufacturing the three-dimensional dental restoration using the final 3D computer model of the dental restoration.

In various embodiments, the method further includes automatically identifying a user-adjustable margin line. The virtual relief wax is added, for example, to the initial 3D computer model in the forming of the virtual refractory model, either before or after the addition of the virtual block-out wax, or the virtual relief wax is added directly to the virtual refractory model, but in any case before the manufacturing step. The virtual relief wax may be added manually or automatically. The virtual design wax may correct one or more scanning errors in the scan of the dental stone and/or prevent one or more fit errors during the casting of the dental restoration The errors may be caused by bubbles, high frequencies, and/or hard corners in the dental stone. At least one step may be performed using a haptic interface device configured to provide force feedback to a user. The haptic interface device may include a stylus or at least six degrees of freedom. The method may further include automatically adding virtual block-out wax to the initial 3D computer model based at least in part on the geometry of the 3D computer model and a direction of insertion of the three-dimensional dental restoration. Adding virtual design wax on top of the virtual refractory model to define a final 3D computer model of the dental restoration may include using one or more virtual wax-up tools selected from the group consisting of a clone tool, a major connector tool, a mesh tool, a ridge tool, a clasp tool, a finish tool, and a lingual collar tool. The final 3D computer model may include a voxel-based representation and a boundary representation. The boundary representation may improve precision of an identified margin line and cement gap.

The description of elements of the embodiments of other aspects of the invention can be applied to this aspect of the invention as well.

In general, in another aspect, the invention includes an apparatus for preparing a virtual refractory model in the design of a three-dimensional dental restoration. The apparatus includes memory that stores code defining a set of instructions and a processor that executes said instructions. The processor thereby creates a model from a scan of a stone or a patient situation, adds virtual block-out wax to the model to fill in an undercut portion and/or a defective portion of the model, and updates the model to incorporate the added virtual block-out wax upon a user command, thereby preparing a virtual refractory model onto which a virtual wax object corresponding to the three-dimensional dental restoration can be built.

In various embodiments, the model is a multi-representational model including a voxel-based representation and a boundary representation. The processor may additionally execute instructions, before the step of adding virtual block-out wax, to modify the model by carving or smoothing bubble artifacts or by ditching the prepared teeth and/or to optionally add virtual relief wax to the scan of the dental stone and/or the model created from the scan of the dental stone to correct errors due to scanning and/or casting the dental stone. The relief wax may be added manually or automatically. The errors may be caused by bubbles, holes, high frequencies, and/or hard corners in the dental stone. The three-dimensional dental restoration may a partial framework, crown, coping, bridge framework, implant, veneer, night guard, bite splint, and/or orthodonture. The virtual refractory model may include a first volume component corresponding to the scan of the stone or the patient situation and a second, separate volume component corresponding to a volume of the virtual block-out wax added to the model; the processor may execute said instructions to further create a virtual wax object corresponding to the three-dimensional dental restoration. The virtual wax object may be built onto the virtual refractory model and may be a multi-representational model including a voxel-based representation and a boundary representation. The user command may include activation of a button.

In various embodiments, the processor executes said instructions to automatically identify and display the undercut portion of the model graphically on a graphical interface based at least in part on a user-selected insertion path, thereby distinguishing the undercut portion from a non-undercut portion of the model. The undercut portion may be displayed with contrasting colors based on degree of undercut. The processor may execute said instructions to display said model in real time as the user adds virtual block-out wax via the user interface; the reduction of the undercut portion may be displayed to the user in real time as the user adds virtual block-out wax. The processor may execute said instructions to automatically add virtual block-out wax to the undercut portion. The processor may execute the instructions to create a jagged understructure in the initial refractory model or to apply a set of preferences to the initial refractory model based on parameter(s) specified by a user. The parameter(s) may include or correspond to patient data and/or a material to be used in the dental restoration.

The description of elements of the embodiments of other aspects of the invention can be applied to this aspect of the invention as well.

In general, in another aspect, the invention includes a system for preparing a virtual refractory model in the design of a three-dimensional dental restoration. The system includes a user interface configured to receive input from a user and a design application in communication with the user interface. The design application is configured to create an initial virtual refractory model using scan data corresponding to a stone or a patient situation. The design application includes a virtual block-out wax tool configured to modify the initial refractory model by adding virtual block-out wax onto a user-defined region of the initial virtual refractory model to fill one or more holes and/or to smooth irregularities on the surface of the initial refractory model, and the design application is configured to update the virtual refractory model to include the added virtual block-out wax upon a user command.

In various embodiments, the design application is further configured to create a virtual wax object corresponding to the three-dimensional dental restoration based on user input via the user interface; the virtual wax object is built onto the updated virtual refractory model. The design application may fit a patch to a surface of the initial virtual refractory model within the user-defined region; said patch may loosely fit convex surface features while not fitting to concave features. The virtual block-out wax tool may be configured to add virtual block-out wax onto the user-defined region of the initial refractory model to compensate for a hole caused by an extraction. The three-dimensional dental restoration may be a partial framework and the virtual block-out wax tool may be configured to add virtual block-out wax onto the user-defined region of the initial refractory model to compensate for a mouth defect. The three-dimensional dental restoration may include a lingual bar and the virtual block-out wax tool may be configured to add virtual block-out wax onto the user-defined region of the initial virtual refractory model to compensate for a lower palate irregularity.

In various embodiments, the virtual block-out wax tool is configured to add virtual block-out wax onto the user-defined region of the initial virtual refractory model to compensate for an artifact of a stone from which the scan data used to create the initial virtual refractory model was obtained. The user interface may be a haptic interface device configured to provide force feedback to a user and the haptic interface device may include a stylus interface. The user interface may be a haptic interface device configured to provide force feedback to a user and the haptic interface device may have at least six degrees of freedom. The user interface may include a mouse and/or trackball. The design application may further include an incisal area reduction tool for creating a jagged understructure in the initial refractory model and/or a preferences tool for applying a set of preferences to the initial refractory model based on parameter(s) specified by a user. The parameter(s) may include or correspond to patient data and/or a material to be used in the dental restoration.

The description of elements of the embodiments of other aspects of the invention can be applied to this aspect of the invention as well.

In general, in another aspect, the invention includes a system for building a virtual wax object corresponding to a three-dimensional dental restoration. The system includes a user interface configured to receive input from a user and a design application in communication with the user interface. The design application may include a virtual wax-up tool configured to build a virtual wax object corresponding to a three-dimensional dental restoration by applying a layer of virtual wax onto a virtual refractory model according to user input via the user interface; the layer of virtual wax may be automatically offset from a surface of the refractory model by a user-specified thickness.

In various embodiments, the three-dimensional dental restoration is a partial framework. The user interface may be a haptic interface device configured to provide force feedback to a user; the virtual wax-up tool may be guided by the user along a surface of the virtual refractory model via the haptic interface device. The virtual wax-up tool may have a volume sampling shape that determines the bounds of an output layer of virtual wax, thereby ensuring continuity of the output layer. The volume sampling shape may be a sphere and may have diameter greater than the user-specified thickness of the applied virtual wax. The virtual refractory model may include voxel data used in modeling the layer of virtual wax. The user interface may be a haptic interface device configured to provide force feedback to a user; the haptic interface device may include a stylus, and the virtual wax-up tool may be configured to interactively paint a layer of virtual wax onto the virtual refractory model in real time according to movement of the stylus by the user.

In various embodiments, the virtual wax-up tool is configured to apply the layer of virtual wax within a region on the surface of the virtual refractory model; said region is identified by the user via the user interface. The layer of virtual wax may be applied within a region bounded by a closed-curve loop drawn on the surface of the virtual refractory model by the user via the user interface. The layer of virtual wax may be applied within a region painted onto the surface of the virtual refractory model by the user via the user interface. The design application may fit a NURBS patch to the region on the surface of the virtual refractory model, offset the NURBS patch to a specified distance, and convert the top surface of the patch to a voxel representation. The design application may fit the NURBS patch to the region by relaxing a two dimensional grid of points within the region to produce a desired smoothness. The design application may convert the top surface of the patch to a voxel representation by tessellating the patch to produce a polymesh representation and may convert the polymesh representation to the voxel representation.

In various embodiments, the user interface is a haptic interface device configured to provide force feedback to a user; the haptic interface device may include a stylus interface. The user interface may be a haptic interface device configured to provide force feedback to a user; the haptic interface device may have at least six degrees of freedom. The user interface may include a mouse and/or trackball.

The description of elements of the embodiments of other aspects of the invention can be applied to this aspect of the invention as well.

In general, in another aspect, the invention features a system for modifying a model of a three-dimensional dental restoration for use with a rapid-prototyping machine. The system includes a user interface configured to receive input from a user and a design application in communication with the user interface. The design application is configured to receive a model of a three-dimensional dental restoration comprising a margin line. The design application includes an edge thickness tool configured to increase a thickness of the model at the margin line to a selected minimum value according to one or more constraints of the rapid prototyping machine.

In various embodiments, the contraints(s) of the rapid-prototyping machine may include a resolution. The dental restoration may include a coping and/or a veneer. The increased thickness of the model at the margin line may include a shelf perpendicular to a surface of the model of the three-dimensional dental restoration. The minimum value may be approximately 0.2 mm.

The description of elements of the embodiments of other aspects of the invention can be applied to this aspect of the invention as well.

In general, in another aspect, the invention features a system for designing a three-dimensional dental restoration. The system includes a haptic interface device configured to provide force feedback to a user and receive input from the user, a graphical interface configured to provide graphical feedback to the user, and a design application in communication with the haptic interface device and the graphical interface. The design application includes a workflow module configured to display a dialog box to a user via the graphical interface in response to a user input, and the dialog box includes a stepwise list of instructions to guide the user through a prescribed workflow in designing a three-dimensional dental restoration using the haptic interface device, the graphical interface, and the design application.

In various embodiments, the workflow module is configured to display a sequence of dialog boxes to the user, wherein each dialog box in the sequence includes a stepwise list of instructions in performing a subtask of the prescribed workflow. The three-dimensional dental restoration may be a member selected from the group consisting of a partial, a partial framework, a bridge, a coping, a veneer, a multi-unit bridge, a prosthetic tooth, prosthetic teeth, a pontic, an implant, an implant abutment, and an implant bar. The dialog box may include one or more links for activating one or more corresponding functions in the prescribed workflow, which may include at least one function for performing a wax-like modeling task using the haptic interface device with force feedback. The haptic interface device may include a stylus interface. The dialog box may be a member selected from the group consisting of a modal dialog box, a non-modal dialog box, a window-modal dialog box, and an application modal dialog box.

In various embodiments, the system further includes a graphical user interface that includes a plurality of icons representing functions to be performed in the prescribed workflow and, optionally, one or more additional functions. The design application may be configured to display or highlight in the graphical user interface a particular set of icons corresponding to functions to be performed in a selected prescribed workflow and, optionally, to conceal or remove any icon that does not correspond to a function to be performed in the selected prescribed workflow. The workflow module may include an undo function that, upon activation by the user, cancels an action performed by the user in carrying out one or more steps of the prescribed workflow, negating any effect on the design of the three-dimensional dental restoration caused by the user in carrying out the one or more canceled steps, thereby allowing the user to repeat or omit the one or more canceled steps. The haptic interface device may have at least six degrees of freedom.

The description of elements of the embodiments of other aspects of the invention can be applied to this aspect of the invention as well.

In general, in another aspect, the invention includes a system for designing a three-dimensional dental restoration. The system includes a haptic interface device configured to provide force feedback to a user and receive input from the user, a graphical interface configured to provide graphical feedback to the user, and a design application in communication with the haptic interface device and the graphical interface. The design application may include a graphical user interface (GUI) that may include icons representing functions to be performed in designing a three-dimensional dental restoration using the haptic interface device, the graphical interface, and the design application; at least one of the functions may include default settings established prior to user selection.

In various embodiments, the default settings include dimensions or one or more wax patterns. The design application may be configured to display a dialog box upon activation of a function by a user; the dialog box may display the default settings corresponding to the user-activated function. The default settings may be set via a lab-wide case management system and made available as input for the design application or may be set via a web service and made available as input for the design application.

The icons may represent tools corresponding to functions that can be performed in a plurality of workflows, and the icons may be arranged in the GUI such that icons representing tools prescribed for use in a particular workflow are in spatial proximity. The icons representing tools for designing a partial framework, coping, and/or a bridge may be grouped together. The icons representing drawing tools and/or wax-like modeling tools may be grouped together. The three-dimensional dental restorations may include a plurality of members selected from the group consisting of a partial, a partial framework, a bridge, a coping, a veneer, a multi-unit bridge, a prosthetic tooth, prosthetic teeth, a pontic, an implant, an implant abutment, and an implant bar. The design application may be configured to display or highlight in the GUI a particular set of icons corresponding to functions to be performed in a user-selected workflow and, optionally, to conceal or remove any icon that does not correspond to a function to be performed in the user-selected workflow. The design application may include an undo function that, upon activation by the user, cancels an action performed by the user in carrying out one or more steps of a prescribed workflow, negating any effect on the design of the three-dimensional dental restoration caused by the user in carrying out the one or more canceled steps, thereby allowing the user to repeat or omit the one or more canceled steps.

The description of elements of the embodiments of other aspects of the invention can be applied to this aspect of the invention as well.

In general, in another aspect, the invention includes a system for extracting a margin line in the design of a three-dimensional dental restoration. The system includes a haptic interface device configured to provide haptic feedback to a user and receive haptic input from the user, a graphical interface configured to provide graphical feedback to the user, and a design application in communication with the user interface. The design application is configured to create a model from a scan of a stone or a patient situation; the design application includes a margin line detection module configured to identify a margin line for the model. The margin line detection module optionally uses haptic input from the user in identifying the margin line.

In various embodiments, the margin line detection module is configured to automatically determine an initial margin line from the model such that the initial margin line is adjusted by the user via the user interface or is accepted by the user without adjustment. The stone may be modified (e.g., ditched) prior to scanning to accentuate the margin line for automatic detection. The margin line detection module may be configured to identify the margin line using a curvature-based mechanism and/or two-dimensional contour detection mechanism. The margin line detection module may be configured to identify the margin line following user selection via the user interface of a strip of geometry on which the margin line resides using an algorithm to detect a closed loop representing the margin line. The strip of geometry is paint-selected by the user using the haptic interface device. The design application in communication with the haptic interface device may provide force feedback to the user to constrain the haptic interface device to the surface of the model during paint selection of the strip of geometry by the user.

In various embodiments, the margin line detection module uses a view-apparent silhouette finding algorithm to detect the closed loop representing the margin line. The haptic interface device may include a stylus interface. The haptic interface device has at least six degrees of freedom. The user interface may include a mouse and/or trackball.

The description of elements of the embodiments of other aspects of the invention can be applied to this aspect of the invention as well.

In general, in another aspect, the invention includes a system for placing a support feature on a three-dimensional model of a dental restoration. The system includes a user interface designed to receive input from a user and a design application in communication with the user interface. The design application is configured to analyze characteristics of the model and determine placement points for the support feature.

In various embodiments, the dental restoration may be a partial framework, crown, coping, bridge framework, implant, veneer, nightguard, bite splint, and/or orthodonture. The support feature may be a sprue and/or a support bar. The design application may be further configured to automatically place the support feature on the three-dimensional model. The design application may include a dialog box querying the user to remove the placed support feature and/or a template for grouping commands, the template comprising steps for analyzing the three-dimensional model and for determining a placement of the support feature.

The description of elements of the embodiments of other aspects of the invention can be applied to this aspect of the invention as well.

In general, in another aspect, the invention includes a system for building a voxel-based representation of a three-dimensional dental restoration. The system includes a user interface configured to receive input from a user and a design application in communication with the user interface. The design application is configured to create a model from a scan of a stone or a patient situation includes a bonding gap module configured to create a voxel-based representation of a three-dimensional dental restoration allowing for a bonding gap between the voxel-based representation and the model. In various embodiments, a bonding gap offset may be specified by the user.

The description of elements of the embodiments of other aspects of the invention can be applied to this aspect of the invention as well.

In general, in another aspect, the invention

BRIEF DESCRIPTION OF THE DRAWINGS

The objects and features of various aspects and embodiments of the invention can be better understood with reference to the schematic drawings described below, and the claims. The drawings are not necessarily to scale, emphasis instead generally being placed on illustrating the principles of the invention. In the drawings, like reference characters generally refer to the same parts throughout the different views. In the following description, various embodiments of the present invention are described with reference to the following drawings, in which:

FIG. 18 illustrates a screen capture of a dialog box for lingual collar options in accordance with one embodiment of the invention;

FIG. 19 illustrates a screen capture of a dialog box for coping settings in accordance with one embodiment of the invention;

DETAILED DESCRIPTION

Figure 1:
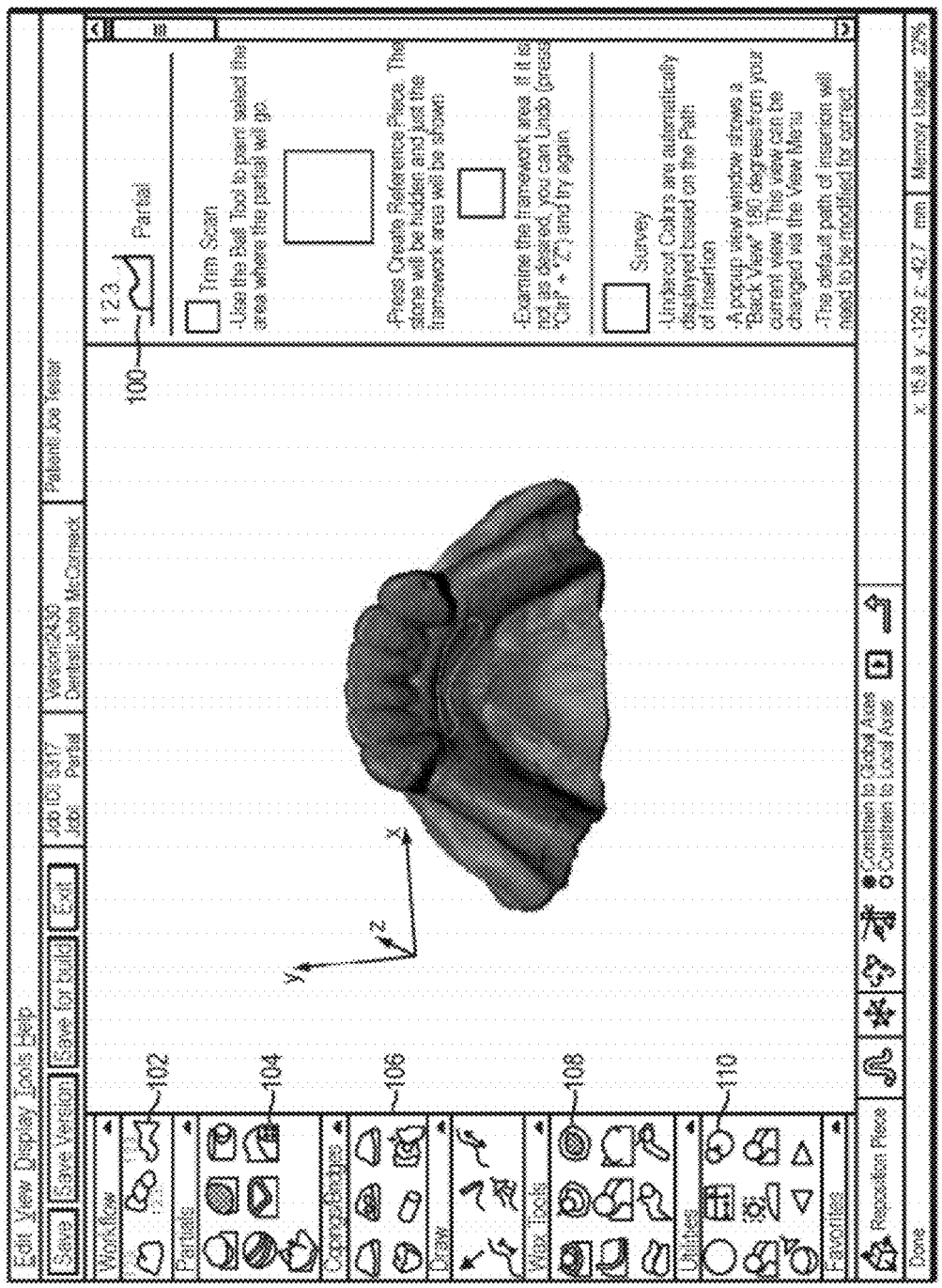
FIG. 1 illustrates a screen capture of a workflow wizard in accordance with one embodiment of the invention.

Throughout the description, where processes, systems, methods, and apparatus are described as having, including, or comprising specific steps and/or components, it is contemplated that, additionally, there are processes, systems, methods, and apparatus according to the present invention that consist essentially of, or consist of, the recited steps and/or components. Furthermore, it is understand the descriptions of elements of a system, method, or apparatus are interchangeably applicable to all corresponding systems, methods, and apparatus.

It should be understood that the order of steps or order for performing certain actions is immaterial so long as the invention remains operable. Moreover, two or more steps or actions may be conducted simultaneously.

Embodiments of the invention may be used with methods and systems embodied in the following patents and/or applications, the disclosures of which are hereby incorporated by reference in their entirety: pending U.S. patent application Ser. No. 11/998,457, titled, "Systems for Haptic Design of Dental Restorations," by Steingart et al.; pending U.S. patent application Ser. No. 11/998,877, titled, "Systems for Hybrid Geometric/Volumetric Representation of 3D Objects," by Faken et al.; U.S. Pat. No. 7,149,596, titled, "Apparatus and Methods for Modifying a Model of an Object to Enforce Compliance with a Manufacturing Constraint," by Berger et al.; U.S. Pat. No. 6,958,752, titled, "Systems and Methods for Three-Dimensional Modeling," by Jennings, Jr. et al.; U.S. Pat. No. 6,867,770, titled, "Systems and Methods for Voxel Warping," by Payne; U.S. Pat. No. 6,421,048, titled, "Systems and Methods for Interacting With Virtual Objects in A Haptic Virtual Reality Environment," by Shih et al.; and U.S. Pat. No. 6,111,577, titled, "Method and Apparatus for Determining Forces to be Applied to a User Through a Haptic Interface," by Zilles et al.

The headers below are provided for ease of reading and are not meant to limit the description of elements of the invention.

Definitions

As used herein, the following terms are generally understood to have the following meanings:

Anatomical copings or crowns—a crown that fits a prepared tooth and features the full occlusional surface—e.g., the external surface of the tooth that meshes with the corresponding tooth on the opposite jaw;

Abutment—a coping-like structure in a bridge framework that fits on a prepared tooth; Blocking out—application of wax to a stone to fix undercuts so that a dental restoration can be inserted successfully;

Bridge framework—the interior structure of a bridge restoration that typically includes one or more abutments and optionally one or more pontics. The abutments and pontics are joined by physical structures called connectors;

Clasp—spring-like metal retention features in a partial framework that attach to existing teeth;

Connector—the physical structure that joins adjacent abutments and pontics in a bridge framework;

Coping—the interior structure of a crown that fits precisely on a prepared tooth. Typically copings serve as an understructure and are finished with porcelain;

Impression—a negative record of the patient's mouth taken at the dentist's office;

Lingual collar—an optional lip or ridge at the bottom of a coping or an abutment that serves as a structural support for the porcelain that will be built up on top of the coping or abutment;

Major Connector—the part of a partial framework for the upper jaw that touches the palate;

Margin line—the line where a coping meets a prepared tooth;

Mesh area—a mesh-like structure in the partial framework that accepts an acrylic dental restoration;

Occlusional surface—the actual exterior surface of a tooth or a dental restoration;

Partial framework—a removable metal framework with clasps that attach to existing teeth, featuring mesh areas for supporting artificial teeth;

Path of insertion—the direction in which a partial, coping or bridge will be inserted into the mouth of the patient;

Pontic—the interior structure of a tooth restoration for a missing tooth in a bridge;

Preparation line—see margin line;

Refractory model—in partial framework design, this refers to a copy of a blocked out stone where wax was used to fix undercuts. The refractory model is typically made in investment material;

Spue—a metal post that may connect an implant to a patient's jaw bone;

Stone—a positive model of the patient's mouth geometry, typically made of a plaster material. A stone can be made from an impression or it can be copied from another stone using a silicone molding process;

Survey—the process of investigating the scanned stone of a patient requiring a partial restoration, and determining the optimal path of insertion for the partial restoration;

Undercuts—overhanging areas in the patient's geometry that may cause a dental restoration to fail to insert, or not be removable once inserted.

In certain embodiments, the dental lab system includes the following modules: Case Management Module—A patient case-management system is integrated into the system to keep track of information on a per-job basis; Scan Module—A mechanism to convert a physical representation of the patient's mouth geometry into a digital format. The scan module may be operated with a 6DOF input device with force feedback, such as the PHANTOM haptic device; Design Module—A software system designed for dental professionals, allowing them to quickly and easily create dental restorations with a sense of touch using a device like the PHANTOM haptic device; and Build Module—A mechanism to generate a physical restoration from the output of the design module. The mechanism may involve an RP based lost wax investment casting process, a milled wax pattern process, an RP to metal part process, or a milled ceramic, composite, or metal part process, for example.

Details about these modules are disclosed herein and in co-pending U.S. patent application Ser. No. 11/998,457, filed Nov. 28, 2007, the text of which is incorporated herein by reference in its entirety. Embodiments of the Design Module are described in detail in this document.

Design Module

The Design Module within the illustrative dental lab system described herein includes a software system that provides ease of use and transparent user interface for dental professionals. In certain embodiments, the software system includes the following: Workflow wizards—The workflow wizard is a widget that introduces the user to each step in a workflow by providing a short text description as well as a link to the tool involved; Workflow oriented organization of tools in the GUI—Tools are grouped according to their relevance to each supported workflow, including partials, crown and bridge, implants and others. User can elect to only see tools relevant to the workflow at hand; System wide preferences—Frequently dental labs have specific know-how that enables them to make dental restorations repeatably. The system provides tools to enable preferences for dimensions, virtual wax patterns, etc. to be enforced on a lab-wide basis, so the same results can be achieved regardless of the actual technician who is doing the design; Virtual refractory model and block-out—In the traditional process, partial framework designers must add wax to a stone to block out undercuts, and then make a copy of this stone with investment materials before they can start waxing up the partial design. The system provides the concept of a "virtual refractory model" where the original, unmodified stone is scanned, and software tools are provided to apply virtual "block-out" wax. This can be done manually, as with the Filler Tools described herein, or through a Virtual Survey process, in which a "path of insertion" is chosen with the aid of a color-mapped undercut visualizer, and blocked-out automatically. A similar provision is available for crown and bridge workflows as well; Virtual wax-up tools—The illustrative system provides a variety of virtual wax up tools that work with a 6DOF (six degree of freedom) input device with haptic feedback, with a stylus interface, that allow users to add and remove wax, smooth transitions and perform other wax like modeling tasks by hand with a sense of touch; Ilaptic widgets—The illustrative system provides a variety of haptic widgets to help provide a transparent and easy-to-use interface; Workflow specific tools—The illustrative system provides specific feature sets for the design of partial frameworks, crowns, copings and bridges and other future workflows.

There are a few existing CAD/CAM systems that address copings and bridge frameworks. None of these are able to support the digital creation of partial frameworks, nor are they haptically-enabled.

The following paragraphs outline components of a Design Module of an illustrative embodiment of the invention.

1. Workflow Wizards

The illustrative Design Module introduces the idea of a workflow wizard. The workflow wizard is a widget that introduces the user to each step in a workflow by providing a short text description as well as a link to the tool involved.

In one embodiment, the workflow wizard may be implemented like a modal dialog box, much like the Windows Installation wizards. Each step is clearly defined, and the user is led through the tools in a predetermined fashion. When they are done with each step, they may click a "Next" button to proceed to the next step. This embodiment is best for well defined workflows that do not typically deviate from the standard path.

In a second embodiment, the workflow wizard may be implemented as a set of modified help files (which can be implemented in a mark up language such as html or xml) with links to the relevant tools. The user can click on the headings of the text to move around in the workflow, and the corresponding tools and objects will be activated. By clicking sequentially through the tasks, the user can finish a design from beginning to end. Each step/section of the workflow wizard should outline what to do in this step of the workflow, with clearly indicated links which activate the right tool or perform the right function or macro.

FIG. 1 illustrates this modified help file approach, where the Workflow Wizard for Partial Frameworks 100 is on the right hand side of the screen.

In this second embodiment, the wizards are designed to be loose and optional on purpose. Novice users or users doing a repeatable workflow may elect to follow the wizards in their creation of dental restoration designs. Advanced users may elect to forego the guidance provided in the wizards and access dental design tools directly as necessary. The user can close the wizard at any time without affecting their work.

In certain embodiments, the user may elect to construct their own workflow wizard to support the workflow that best fit their needs.

An example of the loose type of wizard may take the user through the following steps for a partial workflow: (1) Survey Tool: choose path of insertion and fix draft; (2) Draw Curve: sketch out the clasps, mesh areas, major connectors, and other major features; (3) Filler: fill or smooth out any surface defects or scan artifacts; (4) Mesh: create mesh areas with an optional offset, with tissue stops; (5) Major Connector: create the major connector; (6) Finish Line: create finish lines for mesh areas; (7) Clasp: generate clasps with software aided tapers and other design features; (8) Clone: use a paint-like interface to add virtual wax to connect major areas of the partial framework with each other; (9) Smudge: versatile virtual wax up tool to smooth transitions; and (10) Smooth area: versatile virtual wax up tool to smooth transitions. These steps are just one example of a partial workflow, and the wizard may represent different tools or a different sequence of tools.

In some cases the wizard may allow for a higher level structure. For example the overall bridge construction has three distinct phases: abutments, pontics and connectors each one of these phases could have its own sub wizard. The top level bridge wizard may present an overview of what stage you're at, a higher level navigation display. This can be text based or it can involve use of graphics to illustrate the current step in the process.

For the second embodiment, the user can always access any tool by utilizing the graphical user interface (GUI) directly. The user can at any time continue using the wizard and click on Wizard links to get back to the last step the wizard guided them to.

2. Workflow-Oriented Organization of Tools

In one embodiment, the GUI may be designed to group tools related to a particular workflow in close physical proximity, such that the user may be able to quickly find a tool relevant for that workflow.

For example, one possible grouping of tools by workflow is summarized below. Please note that this is just an example; many other groupings are possible, and tools may be added or subtracted from each workflow. The icons representing these functional virtual tools are pictured at the left in the GUI of FIG. 1, and are listed within each group from left to right and from top to bottom: partial framework tools (102): Survey, Mesh/Riser, Major Connector, Clone, Clasp, Finish Line, and Filler; coping and bridge tools (104): Margin Line, Coping Survey (Fix Undercuts), Generate Coping/Abutment Tool, Pontic, Connector, and Combine (Generate Bridge Framework); draw (106): Select, Draw Curve on Virtual Refractory Model, Split, Join, and Show/Hide Curves; wax tools (108): Smudge, Smooth, Smooth Area, Ridge, Emboss Area, Tug, Add Wax, Toothpaste, and Pipe; utilities (110): Trim Scan, Measure Wax, Add to Refractory, Select Wax with Ball, Select Lump of Wax, Mask, Show Paint Colors, Activate Previous Piece, and Activate Next Piece.

Descriptions of the function of these virtual tools is described in more detail herein. Regarding the Wax tools 108, Smudge adds material or removes it, depending on the haptic force applied by the user (e.g., adds when "pulling" from inside the model, removes when "smudging" from the outside). Smooth Area seeks to lower high points and raise low points in a selected area. Smooth interactively lowers high points and raises low points based on the amount of haptic force is applied by the user, while Smooth area does not use a haptic interaction to determine how much to smooth. Tug deforms the surface of the (virtual) wax based on haptic interaction with the user. The user chooses a point to start the tug, and based on the tool size and haptic interaction, the wax is "tugged" to deform it. Toothpaste adds a stream of wax to the model (similar to squeezing a tube of toothpaste), according to the user's haptic input. Pipe adds a cylinder of clay along a three-dimensional curve specified by the user.

Regarding the Utilities 110, Select Wax with Ball uses a ball-shaped virtual tool to select an area of wax for input to another operation. Select Lump of Wax selects all wax contiguous with the point touched by the user. If there are multiple disjoint pieces of wax in the scene, only that wax connected to the point touched by the user will be selected. Mask specifies an area of wax that is to be protected from modification by other tools (e.g., Smooth and Smudge). The Parting Line Colors/Draft Angle Colors tool shows or hides color on the wax which display where undercuts would occur based on the current path of insertion (pull direction). The display may be multi-color to show the amount of undercut in a given area. Measure Wax shows the thickness of wax in several modes. It can interactively display the thickness of wax on the refractory model, or the distance between two points selected on the wax. In addition, the Measure Wax tool can color the wax based on a minimum and maximum thickness, for example, showing blue where wax is thinner than the minimum distance, and red where the wax is thicker than the maximum.

Figure 2:
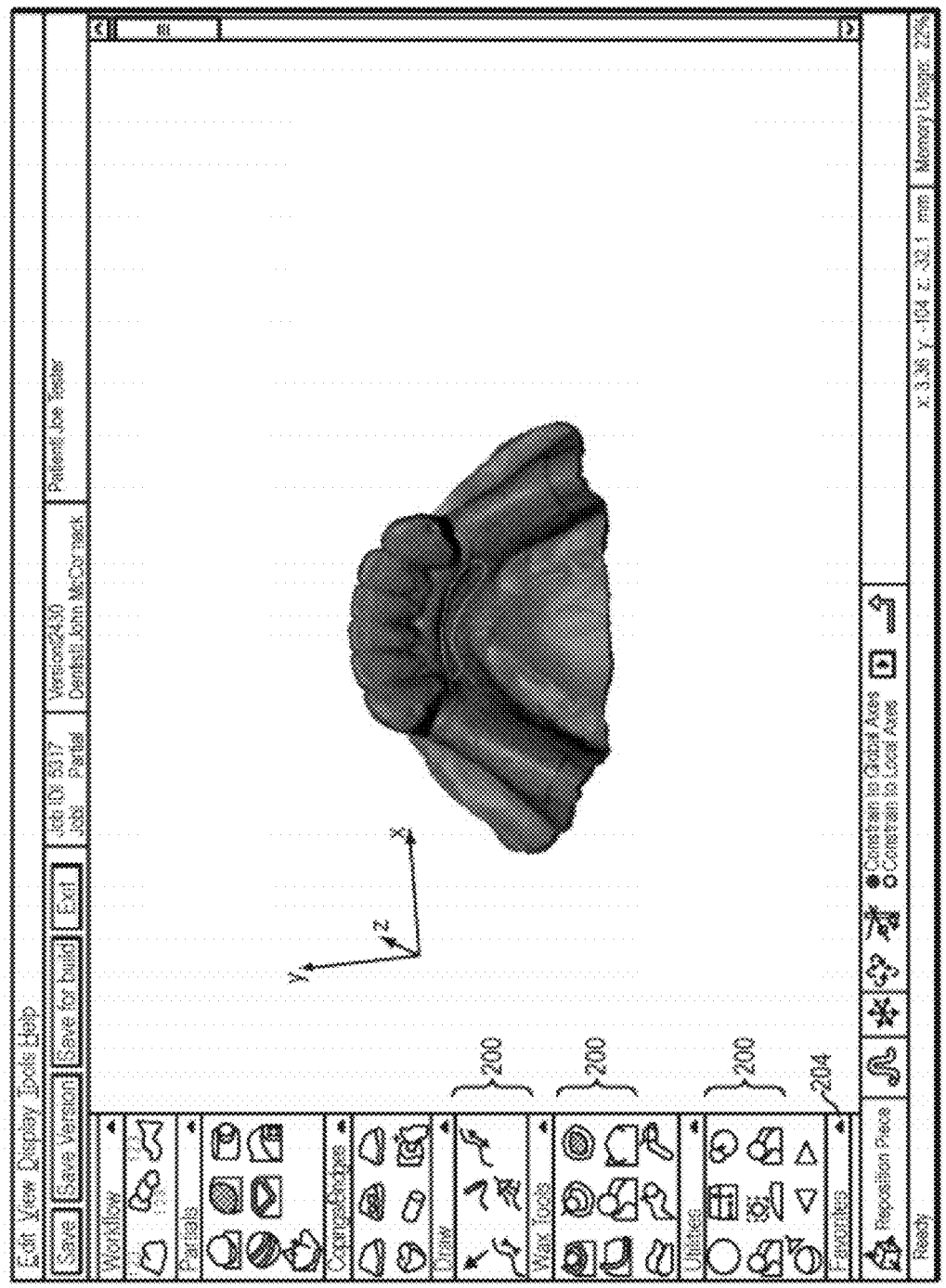
FIG. 2 illustrates a screen capture of groups of palettes in accordance with one embodiment of the invention.

One possible way to group tools together is by placing them in separate palettes 200 as illustrated in FIG. 2.

Users can also generate their own "Favorites" tool set 204, where they define the tools they find the most useful in an order of their choosing. Similarly, a user may generate a programmable workflow macro, or template, to group common steps together. The steps may be, for example, uses of tools, commands, or operations, or other user input. The user may then execute the programmed workflow macro to execute the series of steps as one action instead of executing the steps individually.

Tools that are specific to one workflow do not need to be visible while working on other workflows. In one embodiment, the workflow selected by the user during the Job Information Entry phase is used to control the visibility of tools during the design phase. For example, a job designated to be a partials framework will drive the GUI of the Design Module to show only generic tools (draw tools, wax up tools and utilities) and the partials tools, but not the coping and bridge tools, and vice-versa.

2.1 Structure Placement Workflows

Macros or templates may be used to define the general position of sprue and/or support bar placement, based on anatomical and/or design landmarks. The sprues may be automatically placed on a plastic or wax model for casting based on characteristics of the model (e.g. plastic/wax thickness and/or the distance to certain extremities, such as clasps). The method may automatically determine the optimal placement points for the sprues based on design rules, thereby yielding cast models with minimal voids, short casts, and other casting defects. Placement of sprues may apply to many dental restorations, including partial frameworks, crown/bridge substructures, and overstructures. This same technique may be used to automatically place support bars to prevent distortion and warping of the printed pieces.

2.2 Automated Incisal Area Design

The design of a front tooth may be automated to include a jaggy saw-tooth pattern. The design of aesthetically good-looking anterior teeth requires designing not only the full-anatomy exterior of the tooth, but also some of the underlying structures. For example, at the incisal area, the underlying tooth may appear to have a jagged understructure with a more translucent overstructure at the incisal edge. In one embodiment, the design of a reduced incisal area is automated, thereby eliminating the need for stones or diamond grinding instruments to create the jagged understructure. This method may save time and create more natural looking anterior teeth as part of the initial design process.

3. System Wide Preferences

In most dental labs, there is a body of knowledge and experience that they use to build dental restorations with a repeatable process, and resulting in a consistently high quality of output. Typically, this includes specific choices on wax patterns they purchase from vendors, specific knowledge about typical feature sizes (e.g. the thickness and taper characteristics of clasps and the thickness of connectors and meshes, for example). This is a way to ensure consistency across operators.

To support lab-wide tolerances and design parameters, we provide a mechanism by which key preferences for all key parameters in the design phase are defined at the Case Management application level during the setup phase. The lab owner is therefore able to impose their standard methodology on all users in the lab. The preferences are reflected in the Design Module as default settings for each feature, often in the form of dimensions, wax pattern choices and the like. Users can change these settings to accommodate specific user scenarios, but the default will be consistent across all users.

Figure 3A:
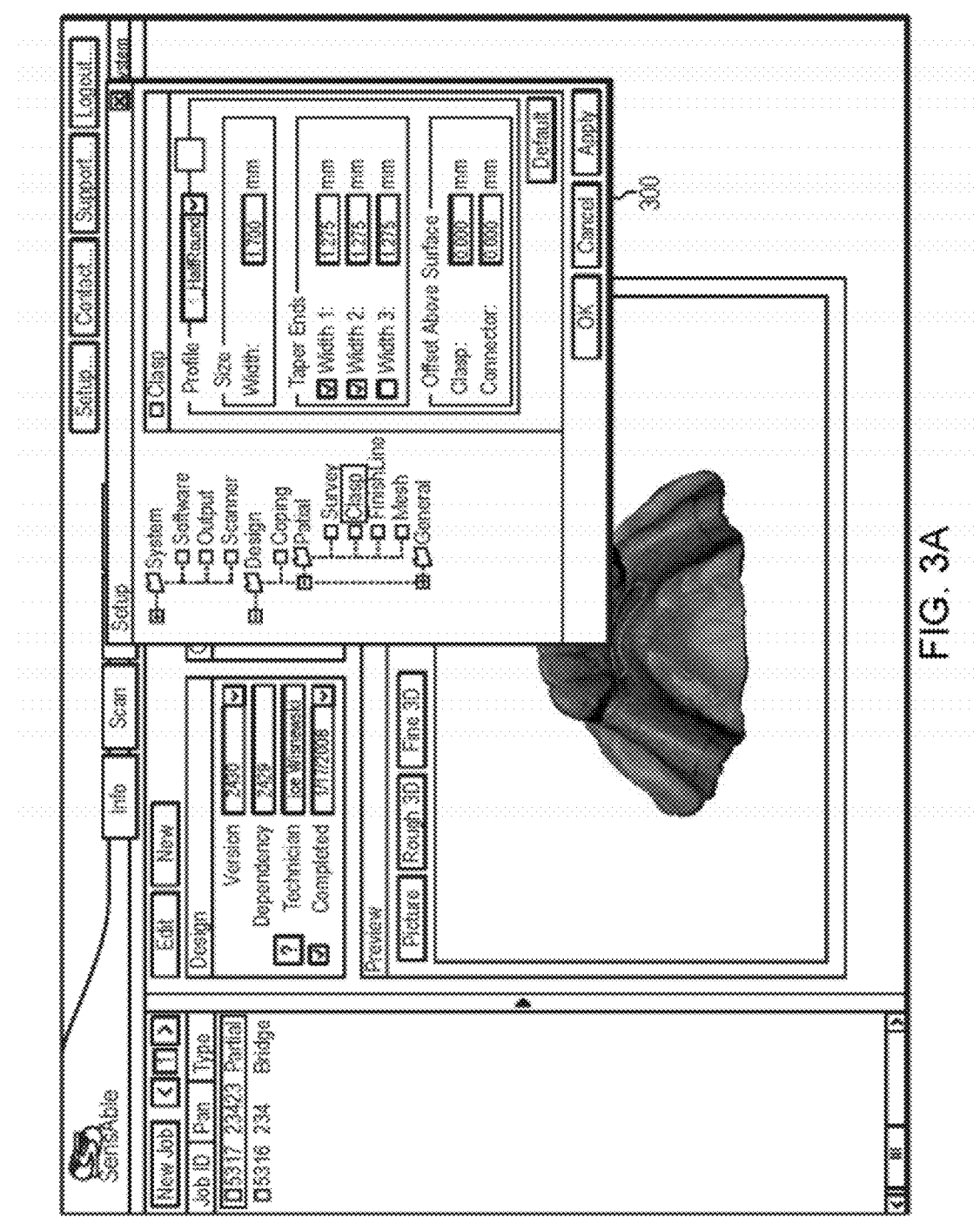
FIGS. 3a-3b illustrate screen captures of setup preferences in accordance with embodiments of the invention.
Figure 3B:
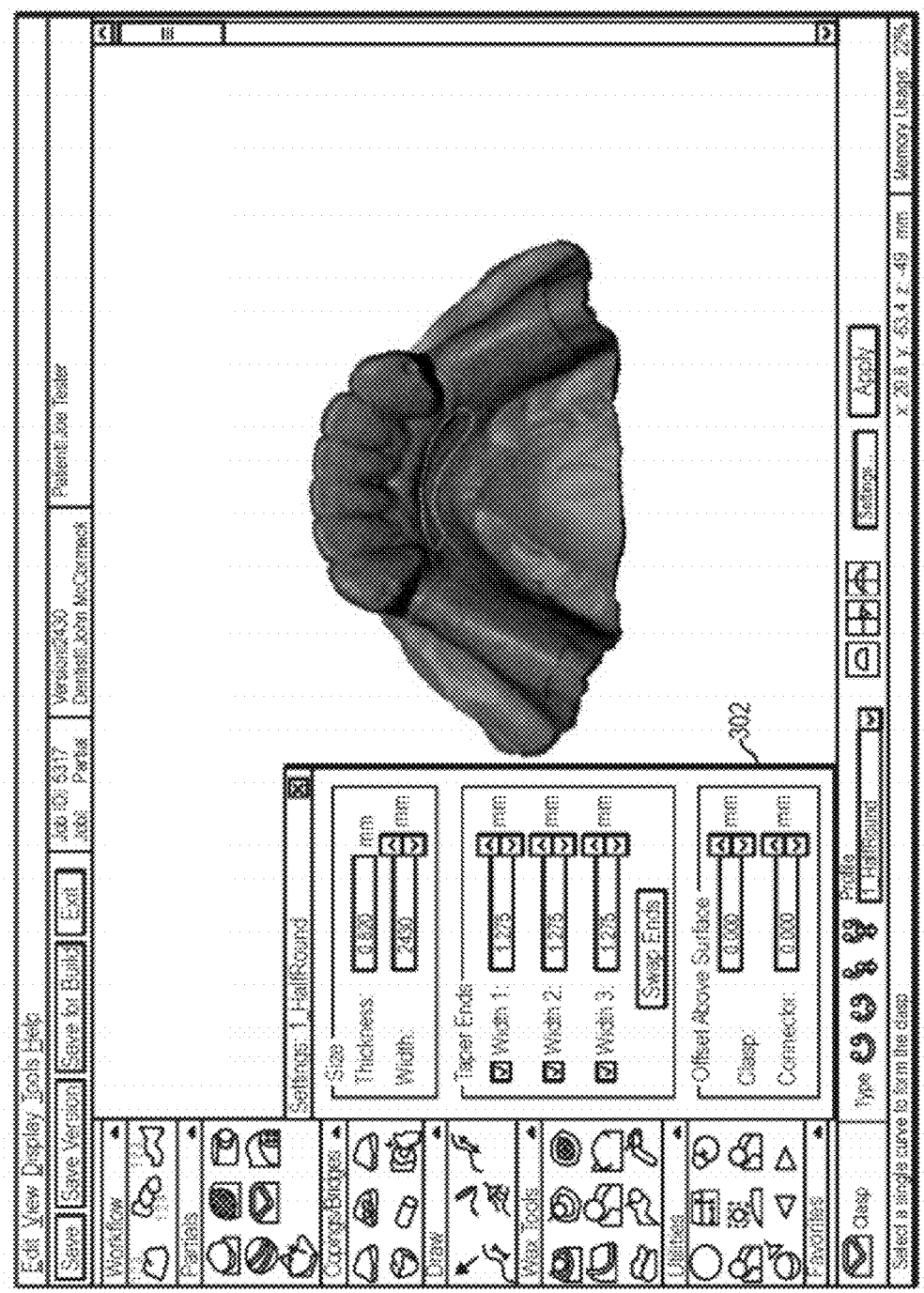

FIG. 3a is a screenshot of the type of preferences that can be set at a lab-wide level through the Setup dialog 300, and FIG. 3b is an example of a feature that derives its default key dimensions from the lab-wide preferences; shown here in the "Settings: 1_Half Round" dialog 302.

4. Virtual refractory or stone and virtual block-out

In a traditional Dental Lab workflow for creating partial frameworks, a "refractory model" is generated by pouring a plaster stone from the impression material, blocking it out with wax to correct for undercuts and other issues, and then making a copy of this blocked out stone with plaster investment material. The resulting product is called the "refractory model", and is the basis for all subsequent hand waxing to create a partial framework. This copy is made via silicone mold which runs the risk of distorting the geometry of the new refractory model unintentionally.

The illustrative system described herein introduces the concept of a "virtual refractory" that eliminates this time consuming and imprecise step. Rather than blocking out undercuts using real wax, the original stone is scanned, and the software can be used to set a direction of insertion and then fix all undercuts automatically based on that direction. The technology behind our implementation of this "block out" step is based on the mechanism taught in U.S. Pat. No. 7,149, 596, (Berger et al), issued on Dec. 12, 2006, which is incorporated by reference herein.

Furthermore, the STL mesh files created in the scanning process are quite large and are monolithic. For further processing in Dental systems, it is common to separate the mesh into smaller segments (corresponding to individual teeth) as required. In one example, this can be accomplished manually, by having the user select a range of triangles on the mesh, by paint or planar selection, and then creating a segment based on this manual input.

Automatic segmentation requires a set of input horizontal x and y positions (in millimeters) corresponding to the centers of the teeth to be segmented. These positions are specified by the scanning device and are input by the user during the scanning process. Using this input, the system calculates the vertical z positions at each x,y by ray casting downwards in the −z direction to find a z intersection point with the mesh. The resulting xyz points are then used as seed points to do "flood fill" selections of the mesh triangles. In a flood fill, all adjacent connected triangles from a starting point become selected in an iterative process. The selection propagation is limited by a lower cutoff plane at a specified distance (measured in the −z direction down from the seedpoint) and a cutoff number of polygons, which prevents excessive selection, flooding, in the x and y directions. Each selection area represents a tooth, which is then made into a separate meshed scan segment.

Visualization techniques, such as applying a color map to the undercuts as viewed from a particular pull direction, can be employed to help the user find the best path of insertion for the dental restoration. This presents a significant productivity improvement over the traditional effort undertaken in the Dental Lab.

Figure 4A:
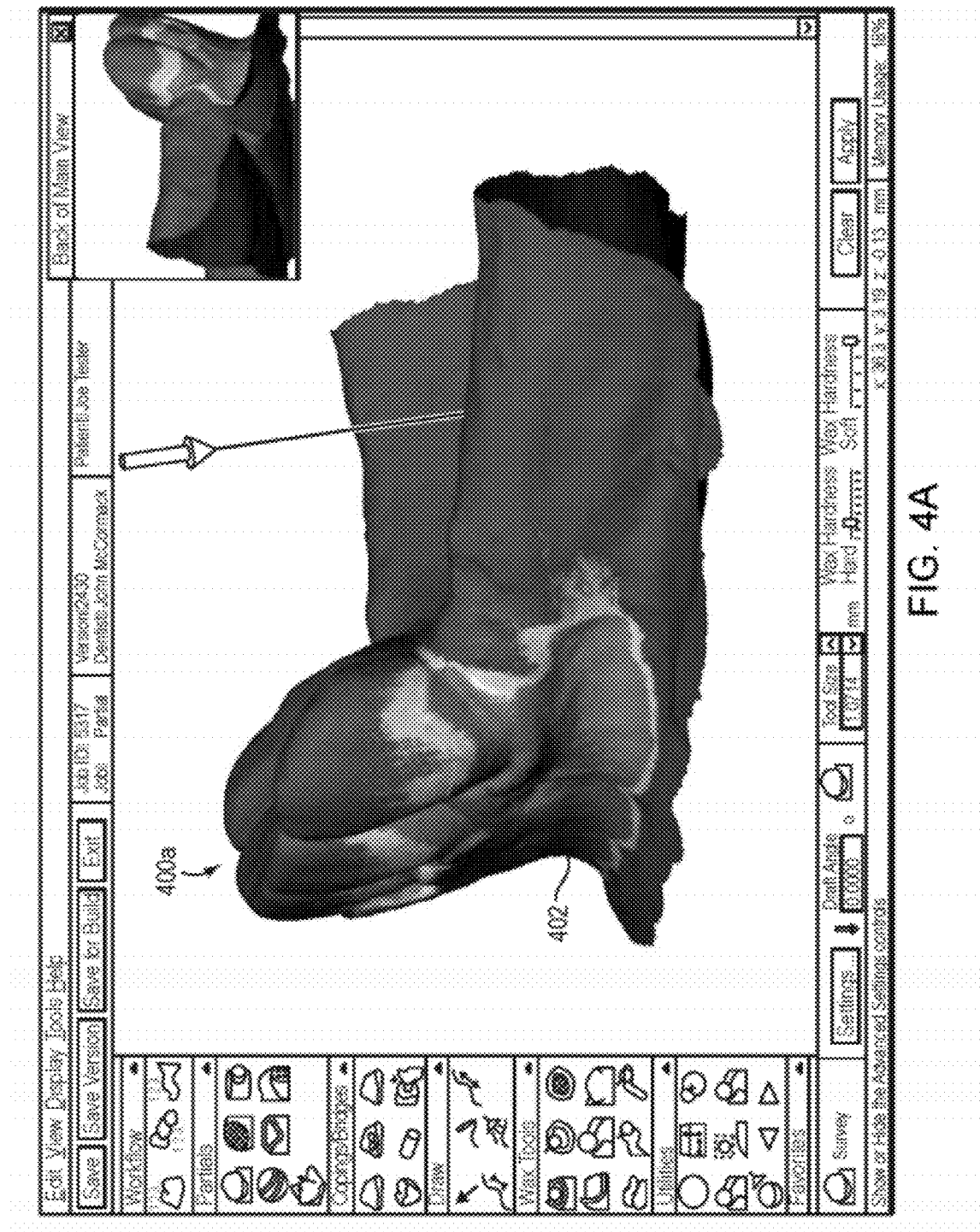
FIGS. 4a-4b illustrate screen captures of a scan model in accordance with embodiments of the invention.
Figure 4B:
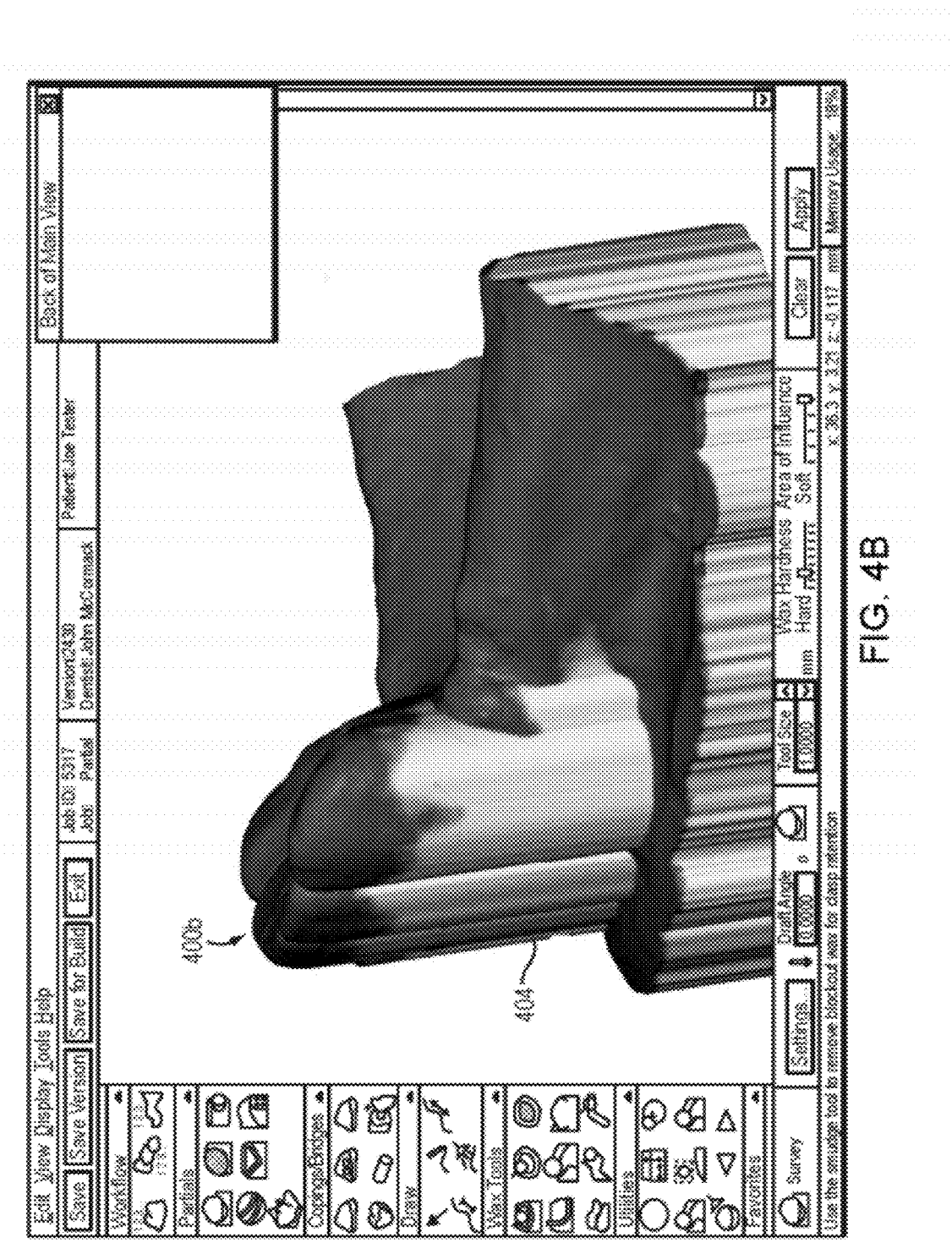

FIG. 4a illustrates the use of a source "scan model" 400a to indicate the undercuts 402. In one embodiment, a color map may be used to indicate the undercuts 402. FIG. 4b illustrates the same model with undercuts automatically filled in with virtual block-out wax 404 to form the "virtual refractory" model 404b.

When creating a coping or bridge framework using the traditional workflow, there is usually no refractory model step, but there are still undercuts which are typically filled in by hand. Again, this process is imprecise and prone to human error.

The virtual refractory model described in this disclosure may be extended to crown, coping and bridge framework workflows. The scanned model may be assessed by the end user; a path of insertion may be selected with aid from a variety of visualization techniques such as color coding the amount of undercut. Furthermore the undercuts may then be fixed automatically based on the path of insertion.

Figure 5A:
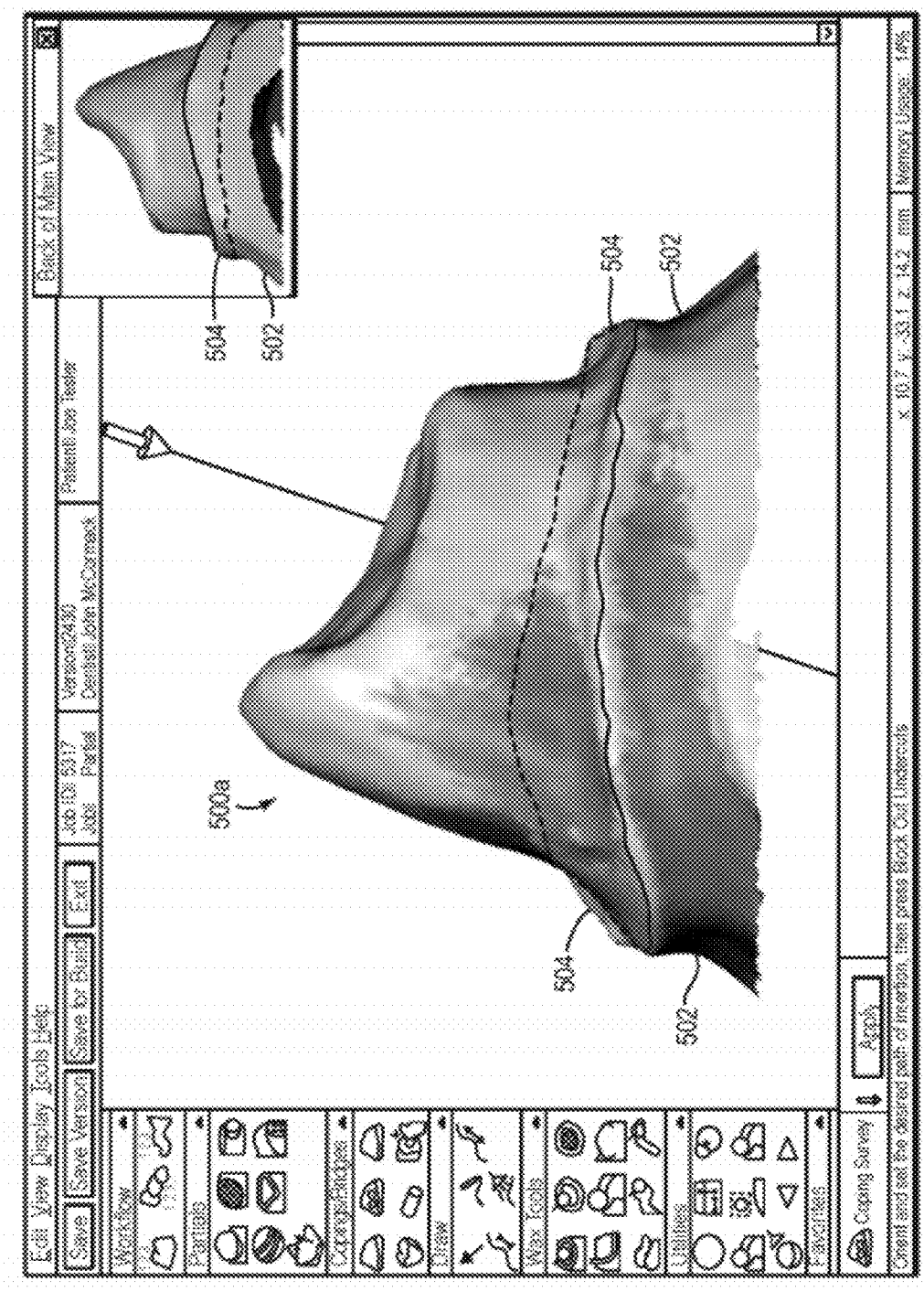
FIGS. 5a-5b illustrate screen captures of a coping scan in accordance with embodiments of the invention.
Figure 5B:
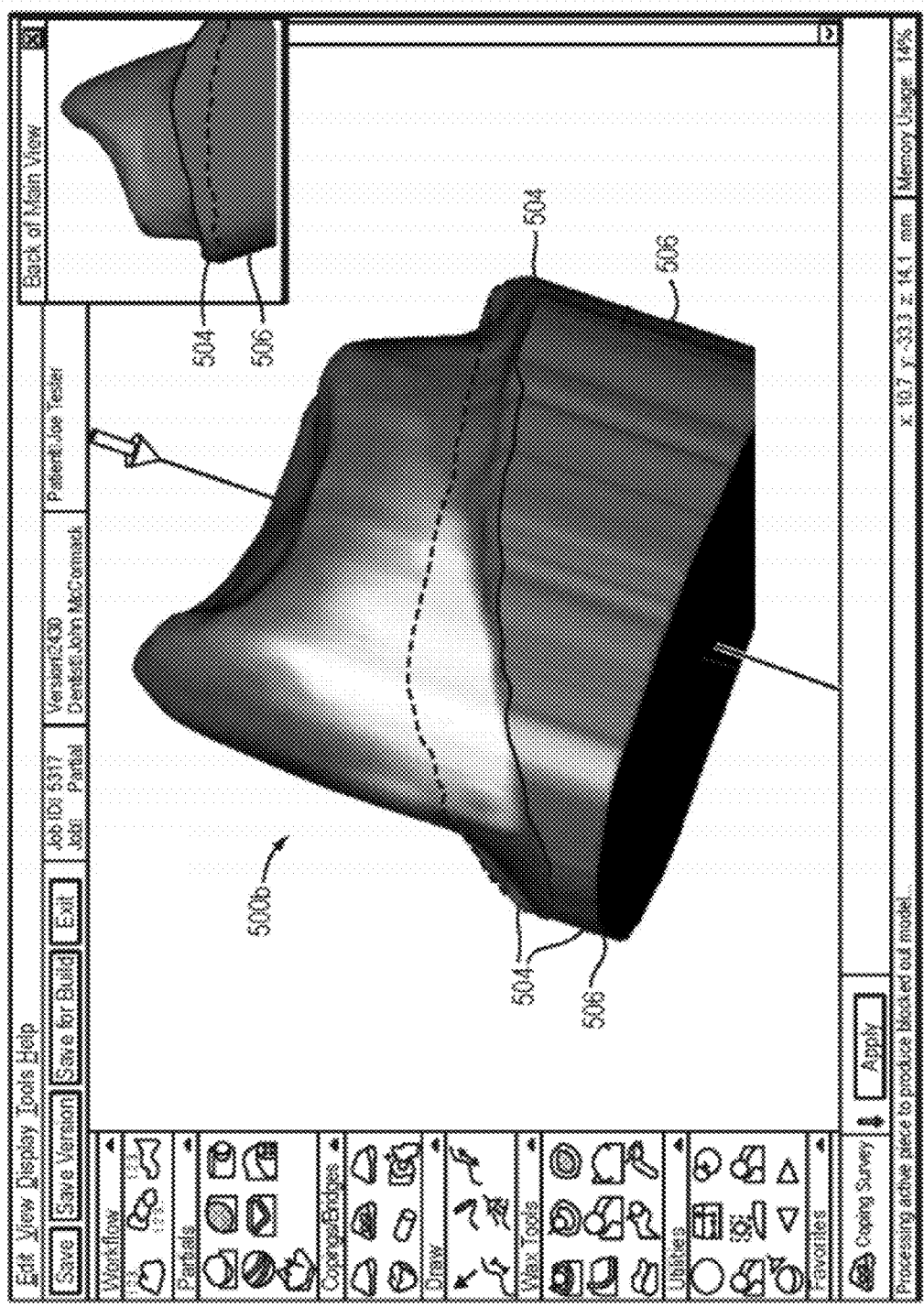

FIGS. 5a and 5b illustrate a coping scan 500a, 500b before and after undercuts are automatically filled in with virtual wax, respectively. In FIG. 5a, undercuts 502 are shown in areas below a line 504. These areas are filled in with virtual wax 506 in scan 500b of FIG. 5b.

In one embodiment, the virtual refractory model is stored as two separate volume components. One volume component represents the scanned patient data and the other volume component represents the algorithmic and user generated "block-out" contents. The union of these two volumes forms the "virtual refractory model".

Subsequent design work for a dental restoration created by the user is stored in a "virtual wax" object volume, which is maintained as a composite of the refractory volume and design wax. At the end of the workflow, a volumetric boolean subtraction may be performed to remove the virtual refractory volume from the virtual wax volume. The result is a manufacturable virtual wax part which accurately fits the patient scan data and accounts for block-out to satisfy the desired path of insertion and user-defined smoothing.

Additionally, a bridge framework may be composed from multiple separate parts, each with their respective scan, block-out and wax volumes. These parts may be combined in a component-wise fashion with volumetric union operations to produce a contiguous whole, from which the virtual refractory volume may be subtracted to yield a manufacturable virtual wax bridge part.

4.1 Virtual Relief Wax

Figure 6:
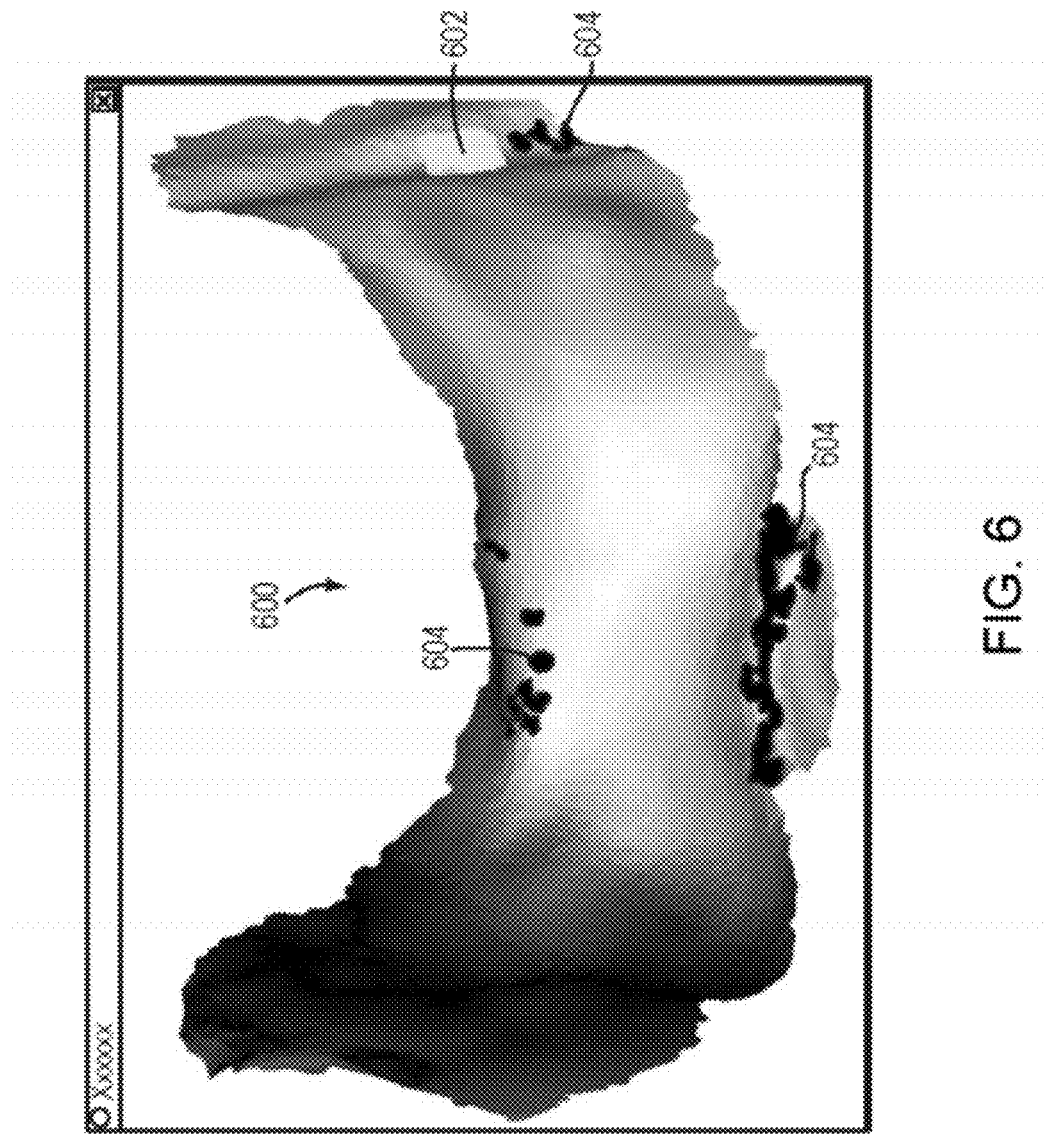
FIG. 6 illustrates a screen capture of a dental restoration in accordance with one embodiment of the invention.

Automatic, semi-automatic, or manual addition of relief wax before a dental restoration is manufactured may optimize the fit of the restoration in areas where, e.g., there are high frequencies or hard corners in the stone or patient situation. A designer using traditional restoration methods may add relief wax manually to a stone and/or a model created from a scan of the stone based on his or her experience and knowledge of the fit for the prosthetic. Embodiments of the present invention also include methods for automatically determining areas of the model that may require virtual relief wax and automatically applying the virtual relief wax so that the finished cast model fits properly, with minimal manual user grinding and finishing of the final cast model. The virtual relief wax may be automatically, manually, or semi-manually applied to areas of the stone and/or model where holes have formed from, for example, bubbles caused by a patient's saliva. FIG. 6 illustrates, in one embodiment, a model 600 of a dental restoration. Relief wax 602 has been added to some areas, and the method has automatically determined that relief wax may be beneficial in other areas 604.

5. Virtual Wax Up Tools

In the physical world, the user is accustomed to a wax-up process, where wax is added and then sculpted away to create the desired features for a dental restoration. The illustrative Design Module described herein provides a class of tools referred to herein as virtual wax up tools that recreate much of the touch and feel of hand waxing. The virtual wax up tools include:

5.1 The Clone Tool—Interactive Wax Addition at a Constant Thickness

Figure 7:
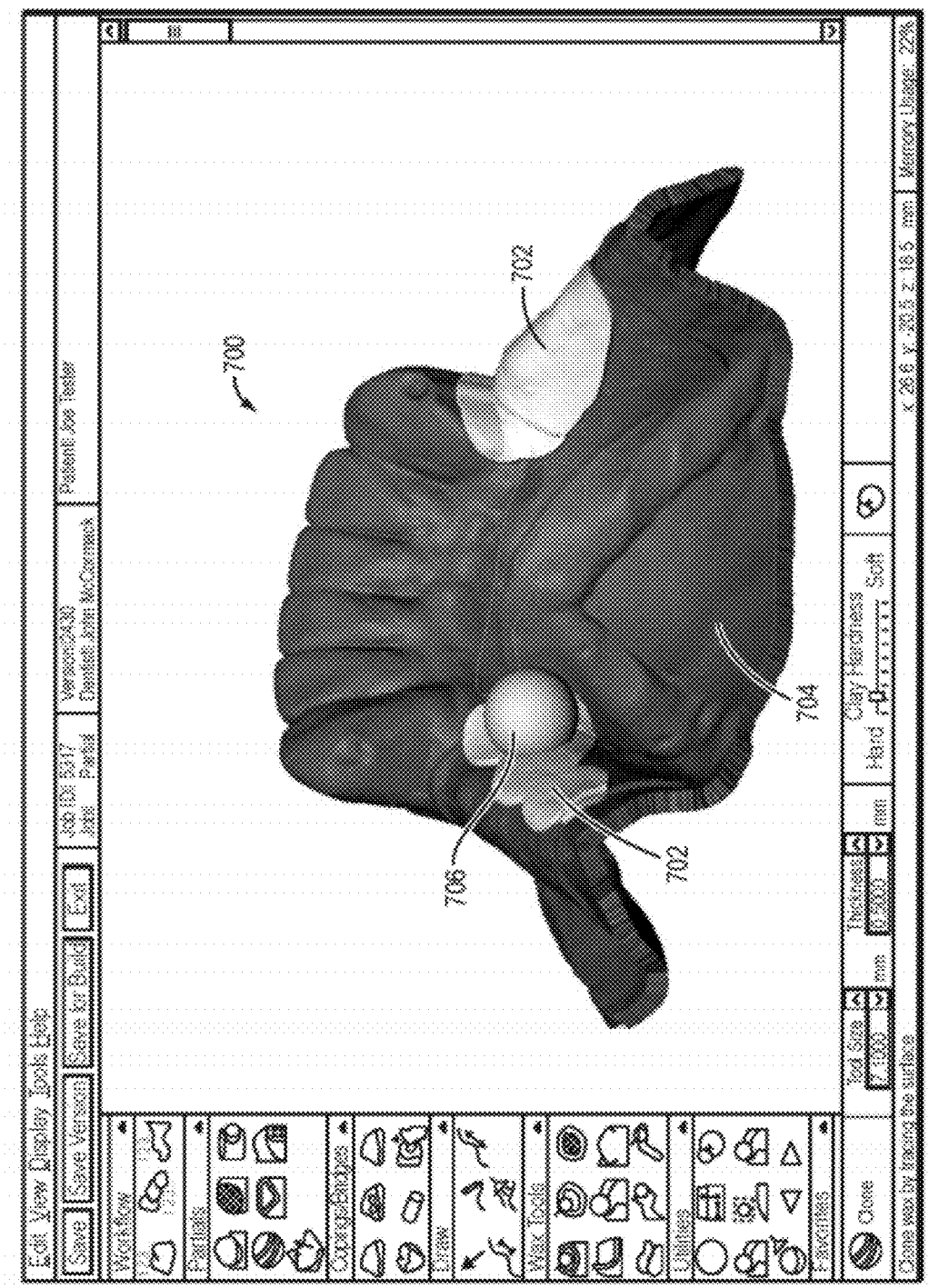
FIG. 7 illustrates a screen capture of a clone tool operation in accordance with one embodiment of the invention.

The Clone tool is a tool created primarily for making partial frameworks, but can be used for other workflows as well. FIG. 7 illustrates a clone tool operation for a sequence of copy instructions. The interaction involves touching and feeling the virtual model 700 with the haptic device. Moving back and forth on the model 700 while depressing the stylus will paint on a layer 702 of wax that is automatically offset from the surface 704 of the refractory model 700 to a user specified thickness. This results in an interactive tool that mimics the effect of laying down a sheet of wax on the refractory model. The improvement to standard tools is that the thickness can be explicitly controlled and does not rely on the user's "eye". Note that the diameter of the ball-shaped brush 706 may be larger than the thickness of the applied wax 702, which may be specified as a numerical parameter.

The clone tool is implemented within the volumetric tool operation framework in FreeForm from U.S. Pat. No. 6,867,770 (Payne), issued Mar. 15, 2005, the text of which is incorporated by reference herein in its entirety. It is an interactive operation which is guided by a 3D position trajectory along the isosurface of a reference volume R (the refractory model). The trajectory of the clone operation is produced from a surface contact point algorithm taught by U.S. Pat. Nos. 6,421,048 (Shih et al), issued Jul. 16, 2002, and 6,111,577 (Zilles et al), issued Aug. 29, 2000 (the texts of which are incorporated by reference herein in their entirety) based on a user tracing the reference volume surface with a haptic interface device. The output of the clone operation is generated in a coincident object volume V. The clone operation is processed as a sequence of local volume copies from R which are transformed and unioned into V.

Note that for the purposes of this disclosure that the 3D position trajectory along the refractory model, R, may be generated by non-haptic means as well; i.e., from mouse input or automatically from a separate computer program.

Figure 8:
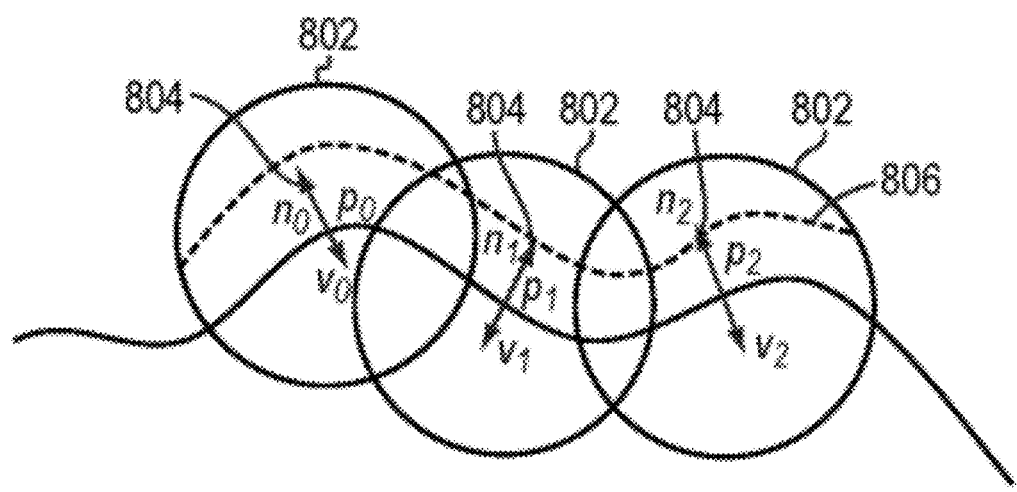
FIG. 8 illustrates clone volume operations in accordance with one embodiment of the invention.

The clone tool operation is processed by decomposing the input 3D trajectory into a sequence of line segments, as illustrated in FIG. 8. Each line segment is described by a start position, $p_0 \in \Re^3$ and an end position $p_1 \in \Re^3$ in volume coordinates. The line segment is used for sweeping a volume sampling shape S which determines the bounds of the cloned output. The swept nature of this processing ensures continuity of the output volume. In the preferred implementation, this volume sampling shape is a sphere, which is described by a radius $r \in \Re$, and centered about the position trajectory. A surface normal $\hat{n} = -\nabla R(p_0)$ is sampled based on the negative gradient of the reference volume at the start position $p_0$ of each segment and used for the entirety of the segment-wise operation. Additionally, in the preferred implementation, a thickness for the clone $\delta \in \Re$ is provided in voxel coordinates. The thickness and normal provide a local offset vector $v = -\delta\hat{n}$ for cloning voxel data from the reference volume to the object volume. At each output object volume location $q \in V$ inside the sampling shape S, a clone sample may be obtained from the reference volume and composited into the object volume via the expression $V(q) = \max(V(q), R(q+v))$.

In FIG. 8, three discrete clone volume operations 802 are depicted, each with their own clone offset vectors 804. The dotted line 806 represents the surface of the output object volume, which is obtained as a local offset of the reference volume. This process of producing the object volume from local offset copies of the reference volume approximates a volume offset, but without the memory and computational overhead of maintaining a distance field or distance query data structure.

5.2. The Major Connector Tool—Applying a Constant Layer of Wax to a Marked Area on the Model The purpose of the Major Connector Tool is to allow the user to apply a constant layer of wax to the model in a batch operation. Technicians today apply a pre-formed layer of wax and press it down to the refractory model. The goal is to mimic this operation digitally so that technicians will have a deep understanding of the needed steps while providing the ability to output a file for computer-controlled machining or rapid prototyping.

Figure 9A:
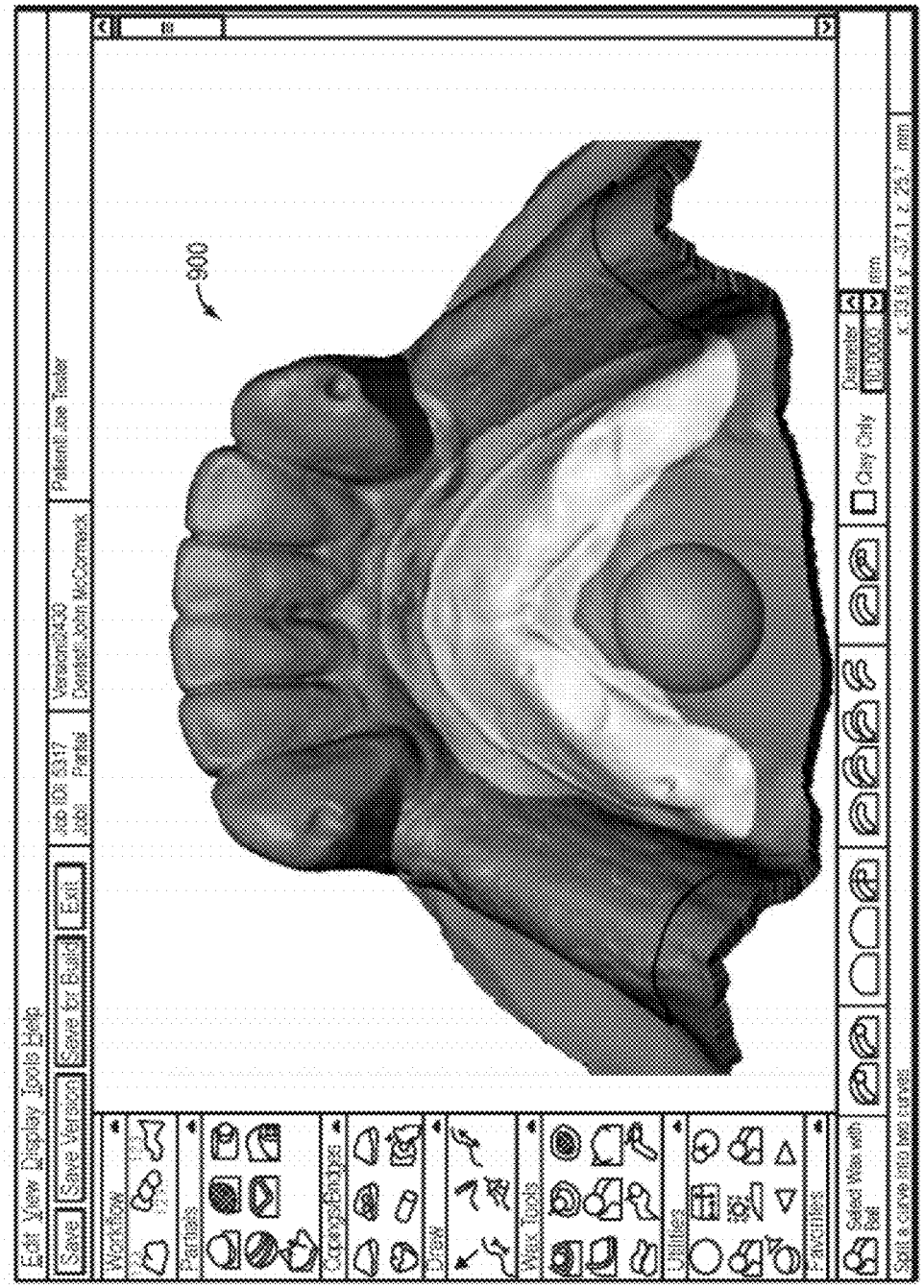
FIGS. 9a-9c illustrate screen captures of a design model in accordance with embodiments of the invention.
Figure 9B:
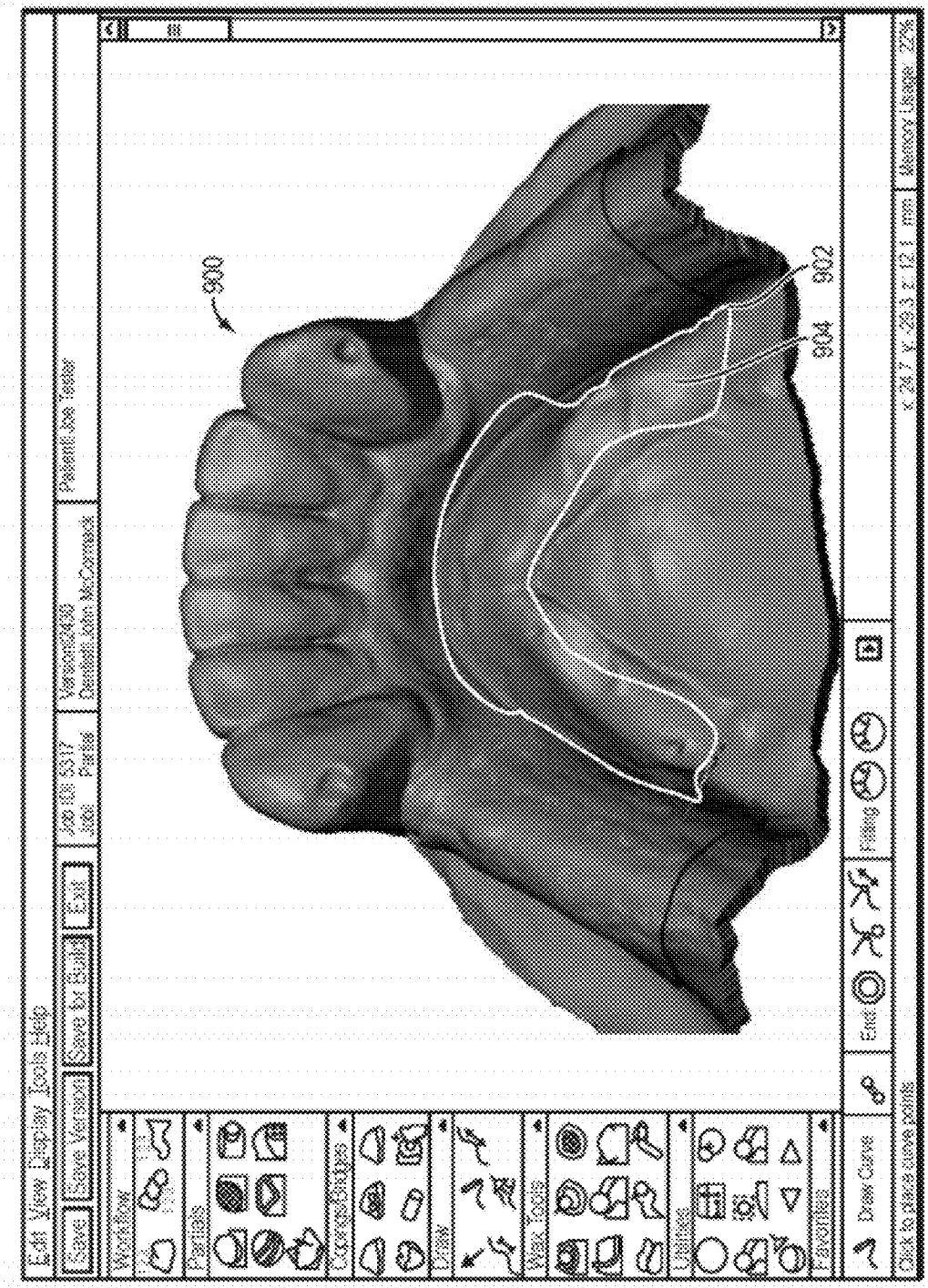
Figure 9C:
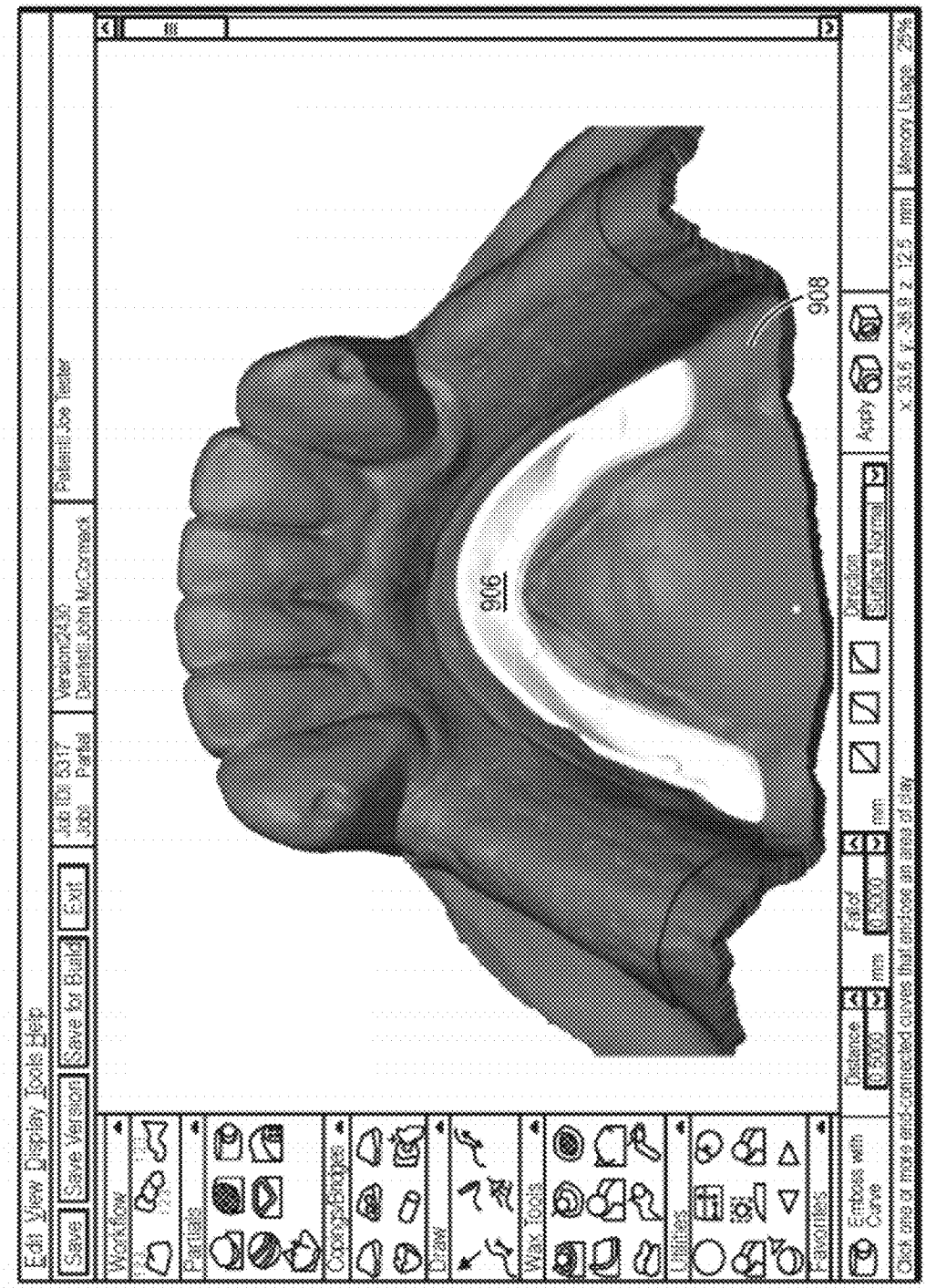

In the illustrative Design Module, shown in FIGS. 9a-9c, the user can mark the area on the refractory model 900 with either a paint-like paradigm or by drawing a closed-curve loop 902 to enclose an area 904 on the model 900. Once the boundary 902 is marked, a NURBS patch may be fit loosely to the underlying model. The NURBS patch is then offset to a specified distance, and the top surface of this patch converted back to a voxel representation by tessellating into a polymesh representation, and then converting to voxels from the polymesh representation. Automatic smoothing of the boundary is achieved by applying an area of influence algorithm to smooth the polygons near the boundary into the underlying voxel model.

The NURBS-to-voxels mechanism is taught in U.S. Pat. No. 6,958,752 (Jennings et al), issued Oct. 25, 2005, the text of which is incorporated by reference herein in its entirety.

The Major Connector feature computes a thickened layer 906 of virtual wax based on the surface 908 of the refractory model 900 and a closed loop boundary curve 904. One way of obtaining this thickened layer is by using a "surface normal emboss" of the triangulated refractory model surface within the closed loop region. However, the resulting embossed surface replicates all of the irregular details of the original refractory model geometry, whereas it is desired to have a smooth top surface for the Major Connector. In addition, the processing of a triangulated surface emboss for high resolution data can be both memory and computation intensive, particularly for a large surface area. Therefore, an alternate approach used by Major Connector is to fit a NURBS patch to approximate the surface of the refractory model and then thicken the patch, which offers both desirable smoothness characteristics and is more efficient for processing. Fitting of a NURBS patch to volume data is used by several features in FreeForm, including Emboss With Wrapped Image, which is taught by the co-pending US patent 20050128211 (Berger et al).

A technique for fitting of a smooth NURBS patch to approximate a densely sampled surface was originally developed by Krishnamurthy (Krishnamurthy et al) for application to dense polygonal meshes. These techniques were later adapted in the SensAble FreeForm software for fitting NURBS patches to the isosurface of a dense voxel volume. The fitting algorithm is performed in two stages. First, a regular sampling of the isosurface is obtained by fitting and relaxing a 2D grid of points within a bounded region. The points are iteratively relaxed using virtual spring forces which constrain the points to be evenly spaced and to follow smooth iso-contours parallel and perpendicular to the patch boundaries. After every iteration of the relaxation, the points are refit to the isosurface by projection along the volume gradient. Once the grid points have been sufficiently relaxed and fit to the isosurface, the points may be approximated using a least squares gridded data fitting algorithm. The number of grid points and related number of control points in the patch surface controls the amount of detail sampled from the isosurface and represented by the patch. This may be determined by a heuristic or controlled by the user to obtain a sufficiently smooth fit to the refractory model surface.

The Major Connector is computed by tessellating the NURBS patch and then computing a "surface normal emboss" from a copy of the tessellated patch. These two surfaces form the top and bottom surfaces of the Major Connector. The boundaries of these surfaces are connected with a strip of triangles to produce a closed triangulated boundary surface. This closed boundary surface is then rasterized into a temporary voxel volume and then unioned with the object volume.

FIGS. 9a and 9b illustrate two ways to mark the area to be smoothed, and FIG. 9c illustrates a layer 902 of virtual wax applied within the defined area.

5.3 The Filler Tool—Smoothing Surface Artifacts in a Marked Area on the Model

The purpose of the Filler tool is to address distinct customer requirements for manually adding "block-out" wax to the virtual refractory when creating a partial framework or other dental restoration by, for example following the following steps. 1. Filling out a hole caused by an extraction. Sometimes patients undergo extractions and then impressions are made for the purposes of ordering a restoration before the extraction holes are healed completely and filled with tissue. The resulting stones will have deep dimples on the extraction site, which over time will become filled with tissue as the mouth heals. 2. Smoothing out defects in the mouth of patients who may have sustained damage over the years from smoking. Smokers may have multiple dimples in their palate that must not be reflected by the underside of a partial framework. 3. Preparing a smooth surface to interface with the lingual bar. The lingual bar for lower partials needs to have a smooth surface rather than reflect every bump and texture on the lower palate. 4. Smoothing the surface of a plaster stone which may include artifacts generated in the process of pouring the stone copies.

The way that Dental Lab technicians address these issues today is to use some hot wax to smooth over the stone itself. The wax drips into crevices and holes, and forms a nice smooth surface on top. This waxed up model is then used to recast a new plaster refractory model. Subsequent wax up tasks to design a dental restoration are then performed on this "touched up" stone.

An advantage of the haptically enabled dental modeling system described herein is that digital wax can be added to an initial digital refractory model in a very simple and controlled manner. This modified model can then be instantly turned into a new refractory model on demand.

To mimic the processes outlined above, a virtual Filler tool allows the user to mark an area to be smoothed by a multitude of ways, such as by the following steps. 1. Paint to select an area by touching the model with the haptic device and painting on its surface by depressing a button while moving the haptic device up and down. 2. Paint through a 2D operation such as with a mouse. 3. Draw a closed-curve loop to mark an area of the model to be smoothed.

To implement (3), the Filler tool smooths the refractory model surface within a region defined by a closed-curve loop. The smoothing is achieved by replacing a region of the refractory model surface with a patch, which has been fit with a specialized objective. The refractory model surface is modified by splitting the surface using the boundary curve loop and replacing the interior region with a tessellated NURBS patch surface. This modified surface may be committed to the refractory model volume representation through the rasterization techniques taught in U.S. Pat. No. 6,958,752 (Jennings, Jr. et al), issued Oct. 25, 2005, the text of which is incorporated by reference herein in its entirety.

Figure 10:
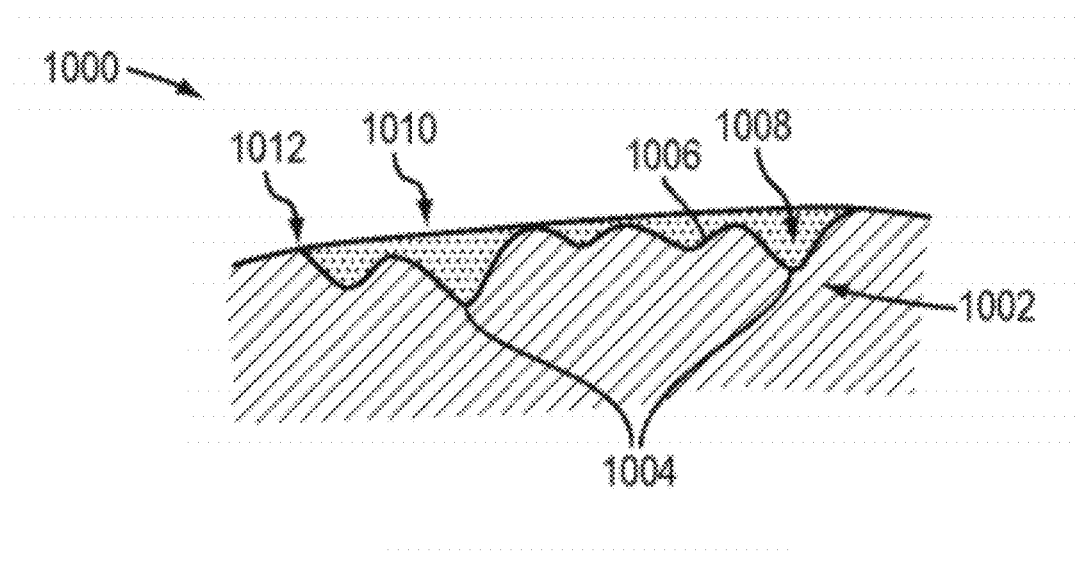
FIG. 10 illustrates a cross-section fit of a filler tool in accordance with one embodiment of the invention.

The process for fitting the NURBS patch to the refractory model surface optimizes a specialized objective to loosely fit to the convex surface features while not fitting to the concave surface features. An illustrative example 1000 of a cross-section fit of the filler tool shown in FIG. 10. A refractory model 1002 contains defects 1004 on a top surface 1006. The filler adds clay 1008 to create a smooth top 1010, including feathered or blended edges 1012.

This approach is implemented as a variation of the patch fitting method described by Major Connector in Section 5.2. The fitting is dependent on establishing a regular sampling of the surface to be approximated using a 2D grid of points. The points are initially relaxed to be evenly spaced to uniformly represent the shape and details of the identified region of refractory model surface. Each point is ranked based on local curvature and only points with concave curvature in one or both dimensions are considered. A smoothing process is then used to iteratively modify these concave points of the 2D grid. At each iteration, the point which contributes the most concave curvature in at least one dimension is modified and moved to a new position based on a weighted average of the neighboring points. Points at the boundary are not allowed to be modified. The limit of this smoothing process results in a completely smooth surface which only interpolates the boundary surface points. However, a user may control both the density of the grid and amount of smoothing through a slider to achieve the desired balance of fit to the refractory while eliminating concave defects.

Figure 11A:
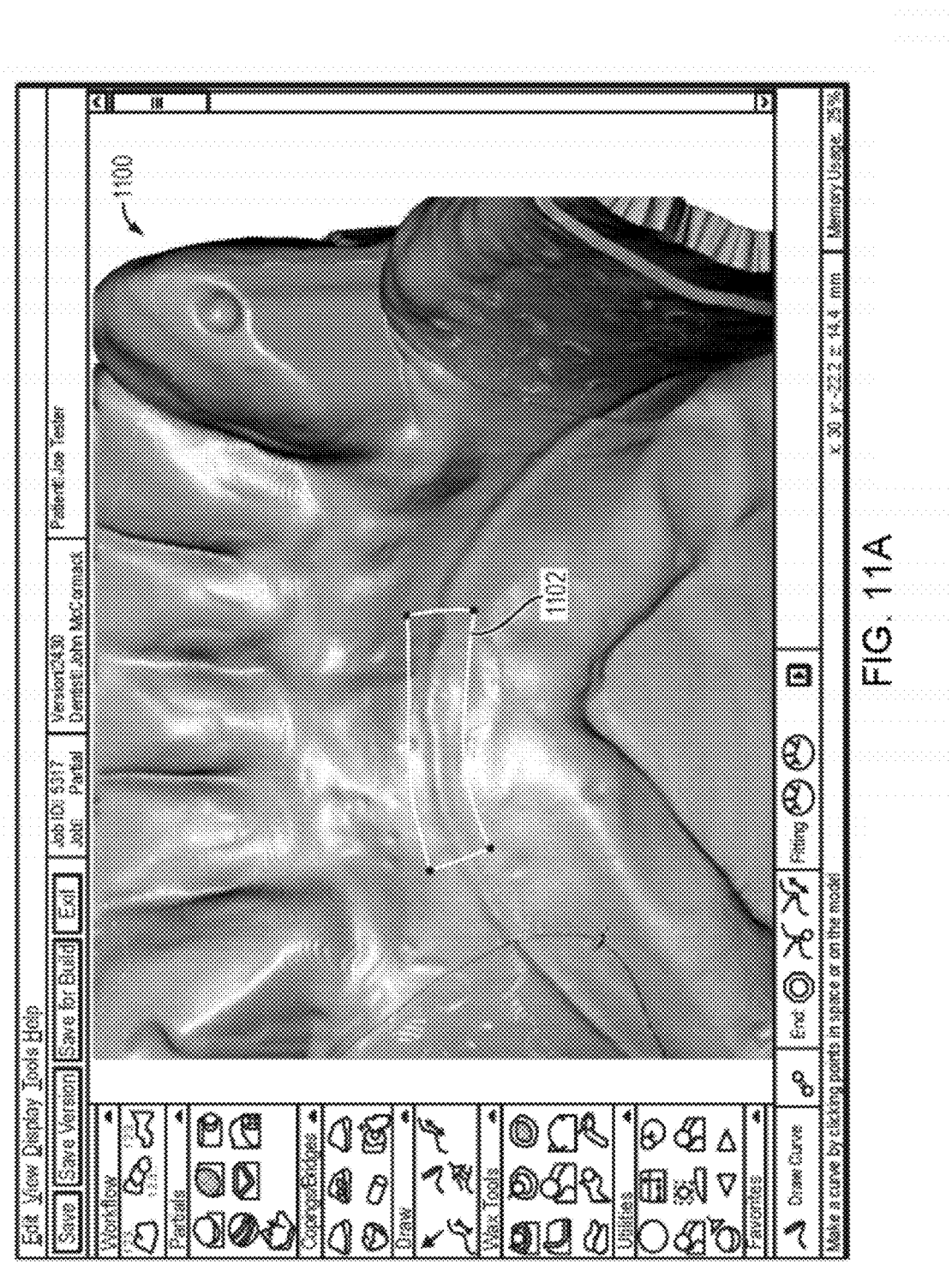
FIGS. 11a-11b illustrate screen captures of a surface of a refractory model in accordance with embodiments of the invention.
Figure 11B:
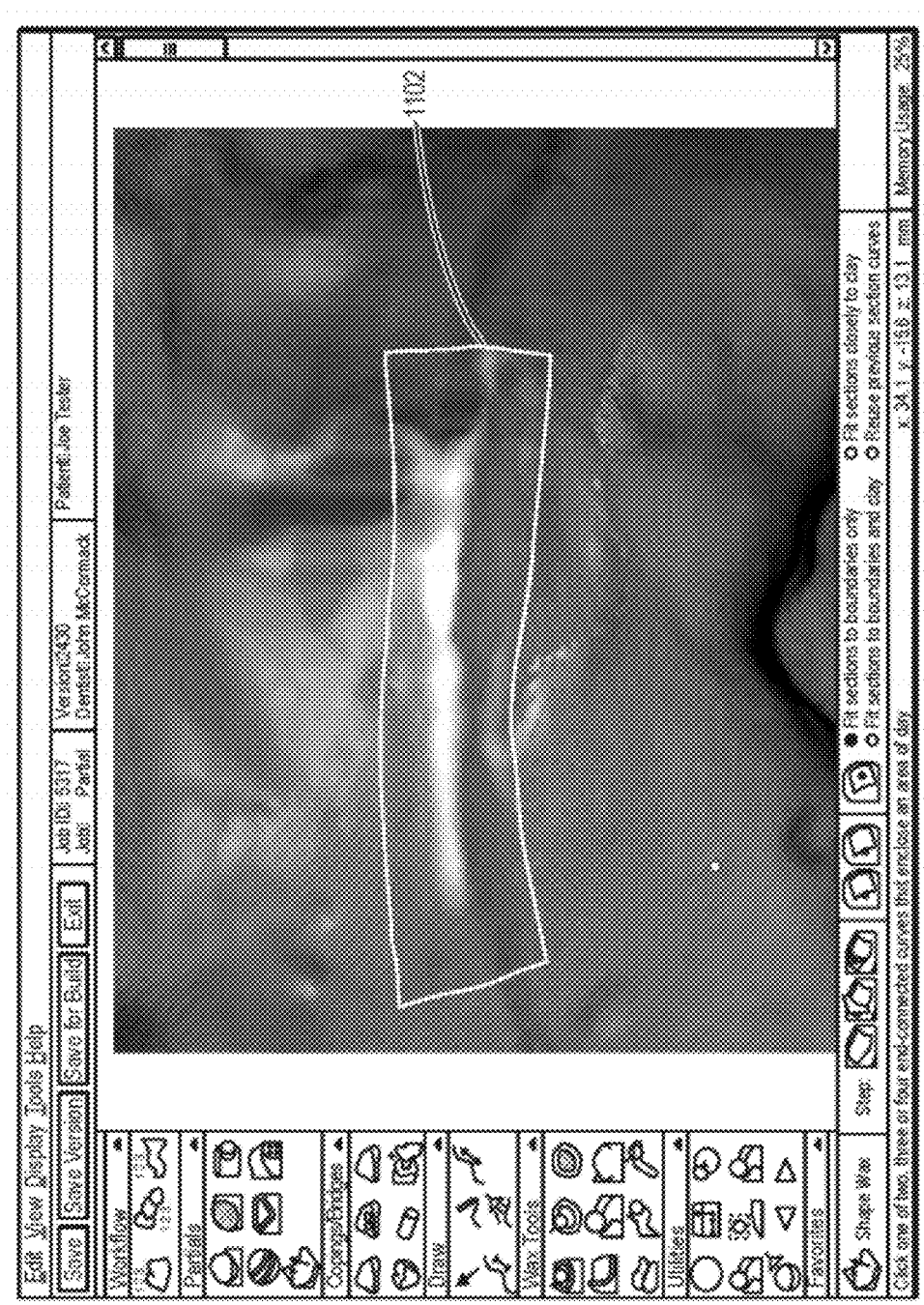

FIG. 11a illustrates the surface of the refractory model 1100 before the smoothing operation is applied. The close-up in FIG. 11b includes an area 1102 which has been smoothed out as described above.

Figure 12A:
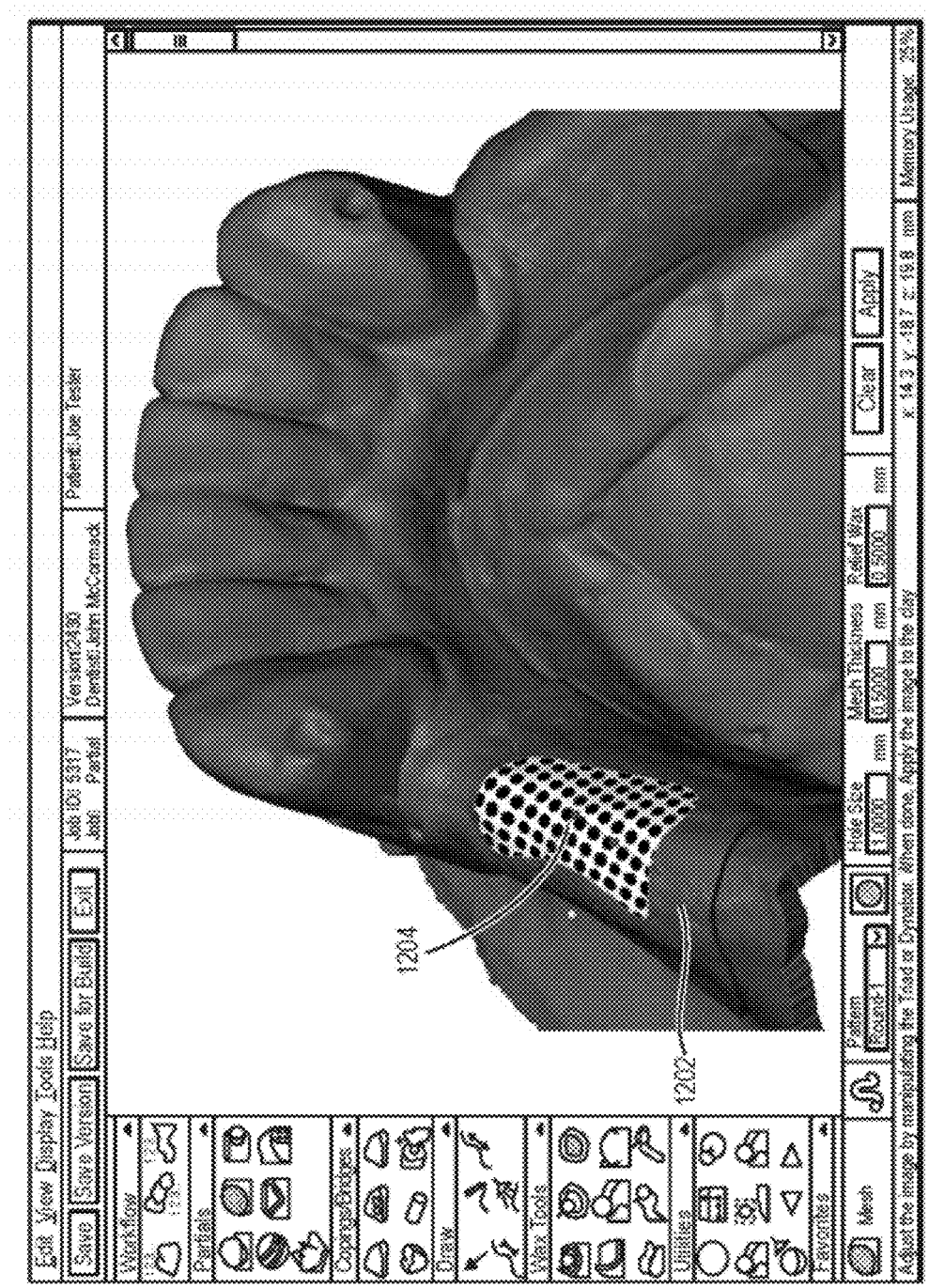
FIGS. 12a-12b illustrate screen captures of mesh and wax relief areas in accordance with embodiments of the invention.
Figure 12B:
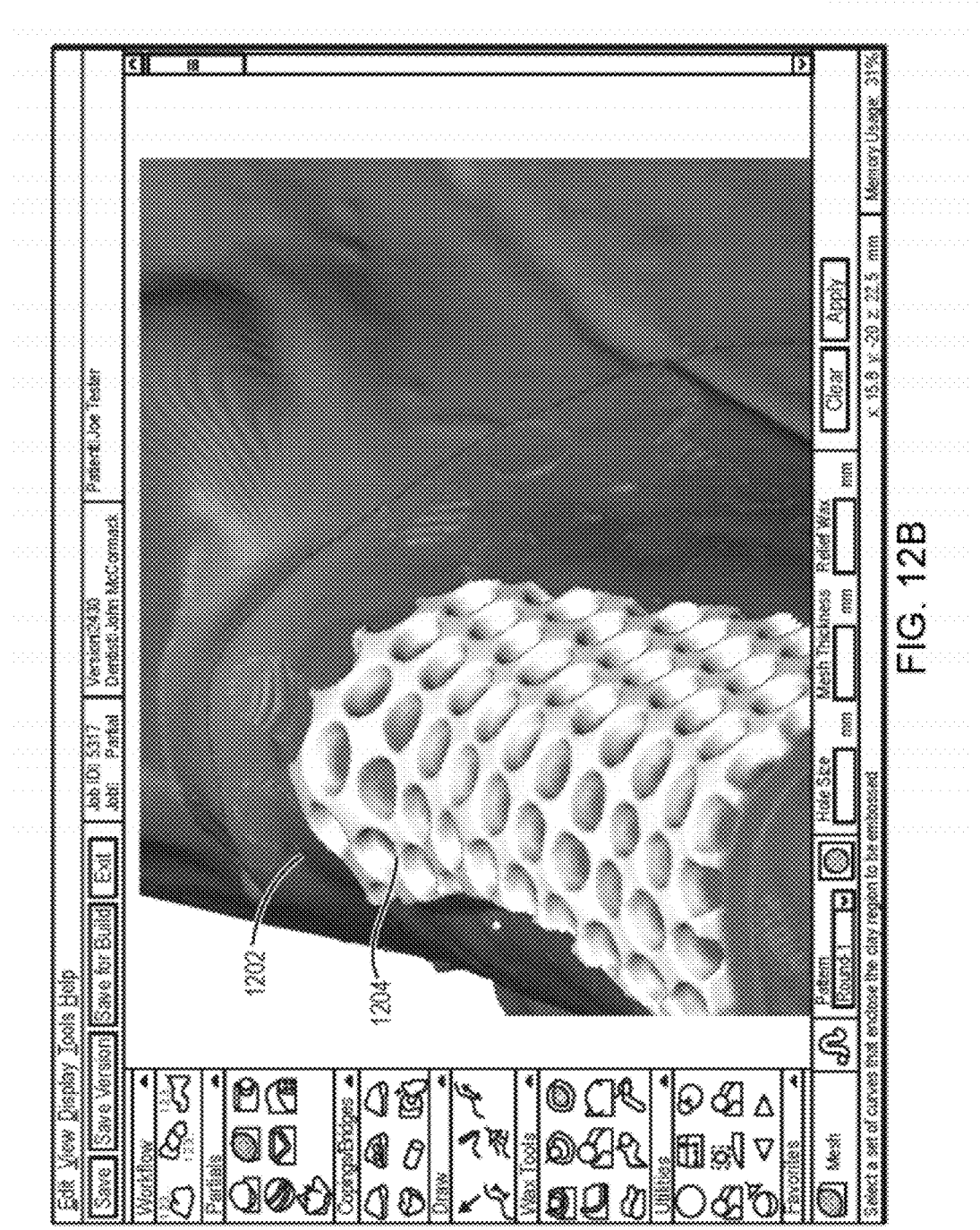

5.4 The Mesh Tool—Applying Virtual Wax Patterns to Create a Mesh Area for a Partial Restoration This tool provides a streamlined way of producing mesh and relief wax areas for a removable partial framework modeling workflow, as illustrated in FIGS. 12a and 12b. A "relief wax area" 1202 is a raised area on the refractory model which ensures that the replacement teeth on the partial framework float somewhat above the patient's gingiva. A mesh 1204 is the portion of the partial framework which will hold the replacement teeth, and consists of a patterned circular or square-holed mesh which captures the epoxy when the replacement teeth are glued into the partial framework.

The relief wax area 1202 is necessary only in creating the mesh 1204, so our invention combines the creation of both items into one workflow and saves the user some repetitive-seeming steps.

For example, in one embodiment, the following five steps are performed to digitally design the mesh portion of a partial framework: 1. Take a selected, user-drawn curve loop as input. 2. User may set parameters for the relief wax and mesh including the thickness of the relief wax, and a mesh offset from the relief wax edge (since the mesh area is inset from the relief wax area). 3. By default, the most often used mesh is retrieved from system-wide preferences. The user may also choose from a list of other standard mesh patterns, or may furthermore customize the current mesh pattern by modifying the thickness, hole size, frequency, shape and other similar parameters. 4. A preview of the mesh pattern appears, as illustrated in FIG. 12a. The hole sizes are as specified by the user via numeric controls. User then adjusts the mesh pattern preview using a haptic (e.g., 3D) or 2D widget (e.g., haptic or non-haptic mouse or trackball) that allows the user to freely rotate and resize the pattern. 5. When completed, the Mesh Tool creates both an offset "relief wax" to add to the refractory model with the correct height (see FIG. 12b); as well as adding the new Mesh to the existing wax representing the partial framework.

In implementing step (4), it is noted that the mechanism for applying a mesh pattern to the area defined by a closed-curve loop without distortion is based on co-pending U.S. Patent Application No. 2005/0128211 (Berger et al), published Jun. 16, 2005, the text of which is incorporated by reference herein in its entirety.

The mesh tool implementation extends on the existing Emboss With Wrapped Image facility (EWWI). The operation uses a closed-loop curve fit to the surface of the object volume as input. The curve is automatically split into four patch boundary curves and then a NURBS patch is fit to the interior of this region. The surface of the object volume is split by these boundary curves and the interior region is replaced with a tessellation of the patch surface. The EWWI processing taught by co-pending U.S. Patent Application No. 2005/0128211 (Berger et al) provides a conformal UV mapping within the NURBS patch surface for tiling a texture pattern without distortion. The mesh tool performs additional processing based on this patch, UV mapping, and tessellation to produce a spacer (relief wax) volume of a desired thickness, $\delta_s$, and a patterned mesh volume with a thickness $\delta_m$.

The spacer (relief wax) volume is generated by offsetting the tessellated patch surface by $\delta_s$ along an average surface normal. Tessellation points along the boundary are not offset. The bottom surface of the spacer volume is obtained from the clipped interior region from the object volume splitting. These tessellated surfaces are combined and rasterized to produce a voxel volume spacer which is added to the digital refractory volume.

The patterned mesh volume is produced as a variation of the "EWWI emboss" processing. First, the tessellated patch surface is offset along an average surface normal by $\delta_s$. The offset is attenuated for tessellation points near the patch boundary based on a linear ramp falloff function. This ensures that the boundary of the patterned mesh volume is slightly inset from the boundary of the spacer (relief wax) volume. Each vertex is additionally offset along its respective surface normal by $\delta_m$ while being modulated by the emboss texture pattern. The "emboss" is also attenuated for tessellation points near the patch boundary based on a step function with a linear ramp. The falloff function further ensures that the boundary of the patterned mesh is sufficiently inset from the boundary of the spacer (relief wax). Further, it is assumed that the boundary of this embossed and offset tessellated surface has not been moved and thus the object volume surface may still be evaluated as a solid. This tessellated surface is rasterized to produce a modified object volume, based on the techniques taught in U.S. Pat. No. 6,958,752 (Jennings, Jr. et al), issued Oct. 25, 2005, the text of which is incorporated by reference herein in its entirety.

Finally, when the refractory volume is later subtracted from the waxed object volume, the patterned mesh volume will be free floating with the desired spacer distance $\delta_s$ underneath and the desired mesh thickness $\delta_m$.

5.5 Ridge Family of Tools—a Series of Dental Sweep/Loft Like Tools

In partial framework and coping/bridge framework workflows, there are many physical features on the restorations that are based on long, extruded wax patterns. For example, a variety of vendors like CMP and Bego sell standard wax patterns with a variety of profiles and end taper characteristics suitable for the creation of clasps and finish lines around the mesh areas in a partial framework. For copings and bridge frameworks, the lingual collar is often fashioned free-form from wax, but the shape of the collar still resembles an extrusion of a varying cross section that is laid on the surface of the wax coping.

In the illustrative Design Module described herein, it is possible to achieve this class of features by using a family of virtual tools labeled herein as "Ridge". The Ridge family of tools accepts one or more guide curves; and one or more cross sectional profiles and additional end taper parameters which can be retrieved from a system-wide preferences database. These inputs are used in order to create a swept or lofted profile along the guide curve with optionally tapered ends on one or both sides.

The internal mechanism to support this is based on the use of temporary NURBS patches which describe the lofted shape and are updated interactively as the user edits the guide curves, changes the size or orientation of the profiles, edits the shape of each lofted profile, or changes the parameters that define the taper conditions at the endpoints. Once the user accepts the preview, the same mechanism that powers the Connector and Filler tools (see above) is used to first tessellate the NURBS patches, and then convert the resulting polymesh to virtual wax.

Figure 13:
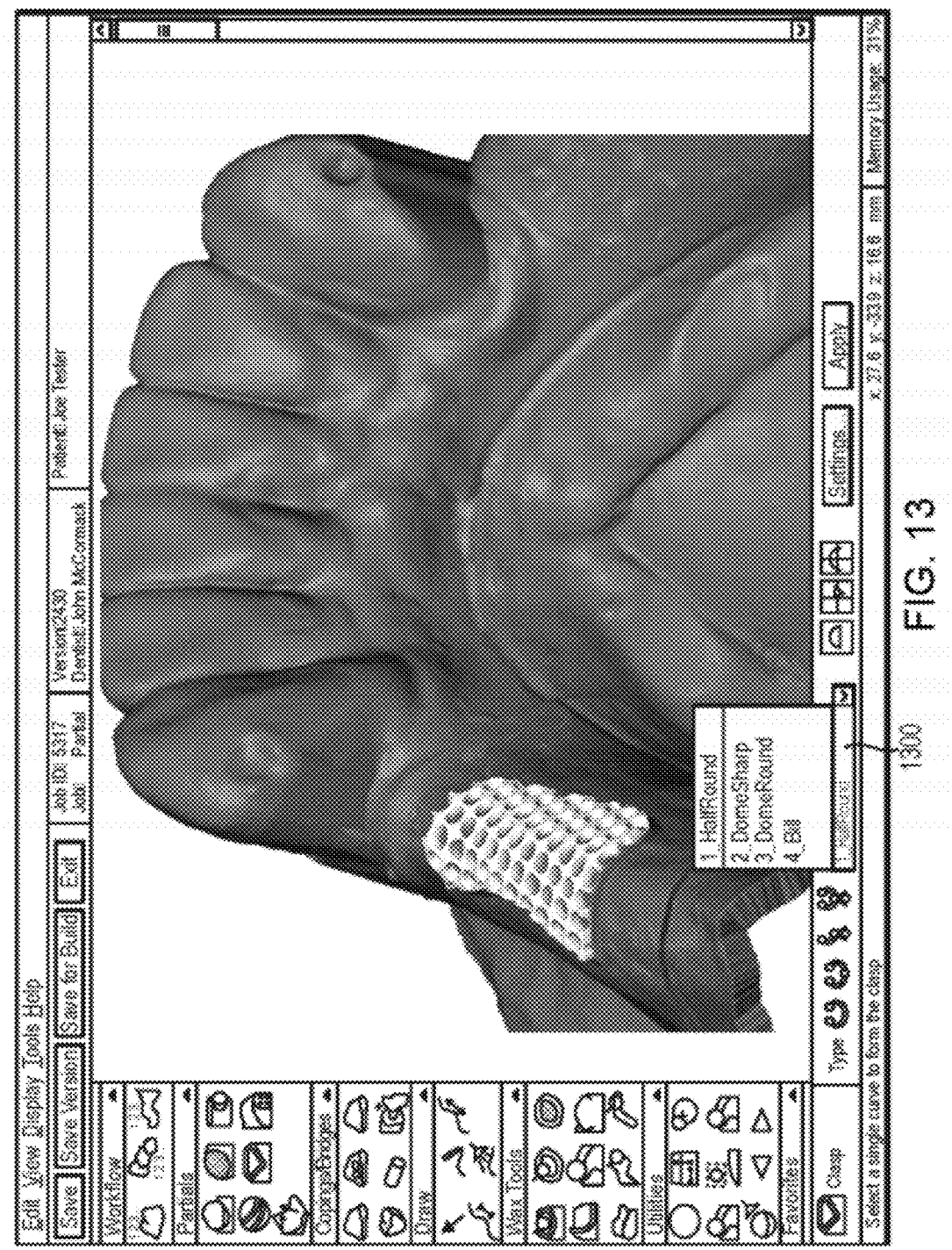
FIG. 13 illustrates a screen capture of a dropdown list in accordance with one embodiment of the invention.

FIG. 13: The dropdown list 1300 at the bottom of the screen illustrates typical cross sectional profiles (e.g., HalfRound or Domesharp) used for different types of Ridge-based tools, including: Ring clasps, J-clasps, T-clasps, Finish lines, strengthening bars for major connectors, and lingual collars for copings and bridges.

Figure 14:
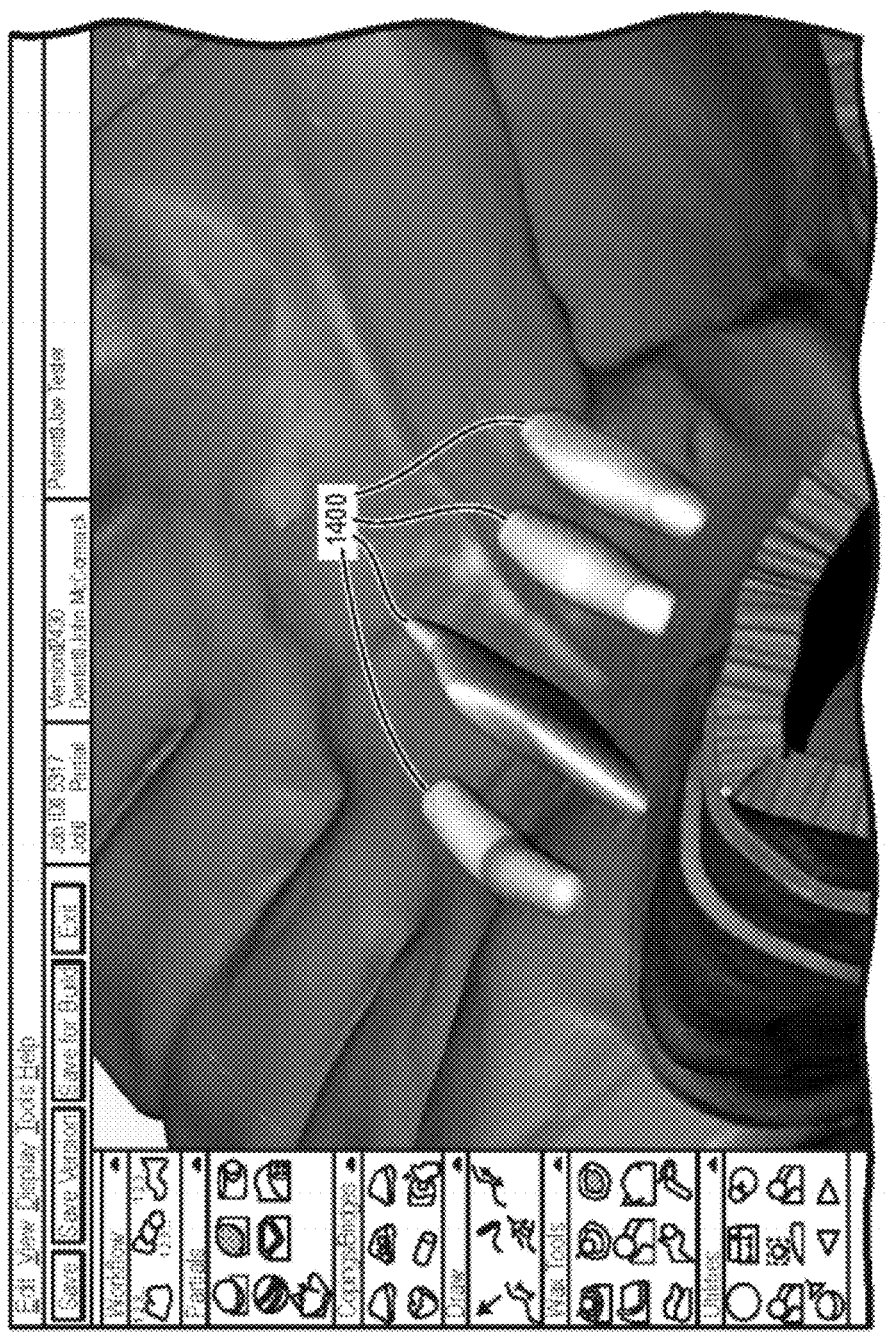
FIG. 14 illustrates a screen capture of a virtual wax output in accordance with one embodiment of the invention.

FIG. 14 illustrates the virtual wax output 1400 using these different profiles.

Haptic aids are used to assist the user in the creation and editing of the guide curves and of the cross section profiles.

Guide curves are drawn by touching points on the surface of the virtual refractory model. Between these edit points, a curve is fit to the surface, following the contour. Once created, the guide curve can be altered by dragging the edit points to new positions on the surface, or by adding or removing points. When the edit points are changed, the curve is automatically refitted to the surface. To aid in edit point selection, each point has a "haptic snap", a small force that attracts and locks the haptic device to the point when it is in close proximity.

Profiles are edited by manipulating a series of joined lines and curves on a two-dimensional plane. The haptic device is restricted in motion to x and y and gives the physical sensation of touching a flat plane. As with the guide curve edit points, haptic snaps assist in the selection and movement of the profile points, as well as the manipulation of handles to control the curve tangent direction at those points.

Figure 15:
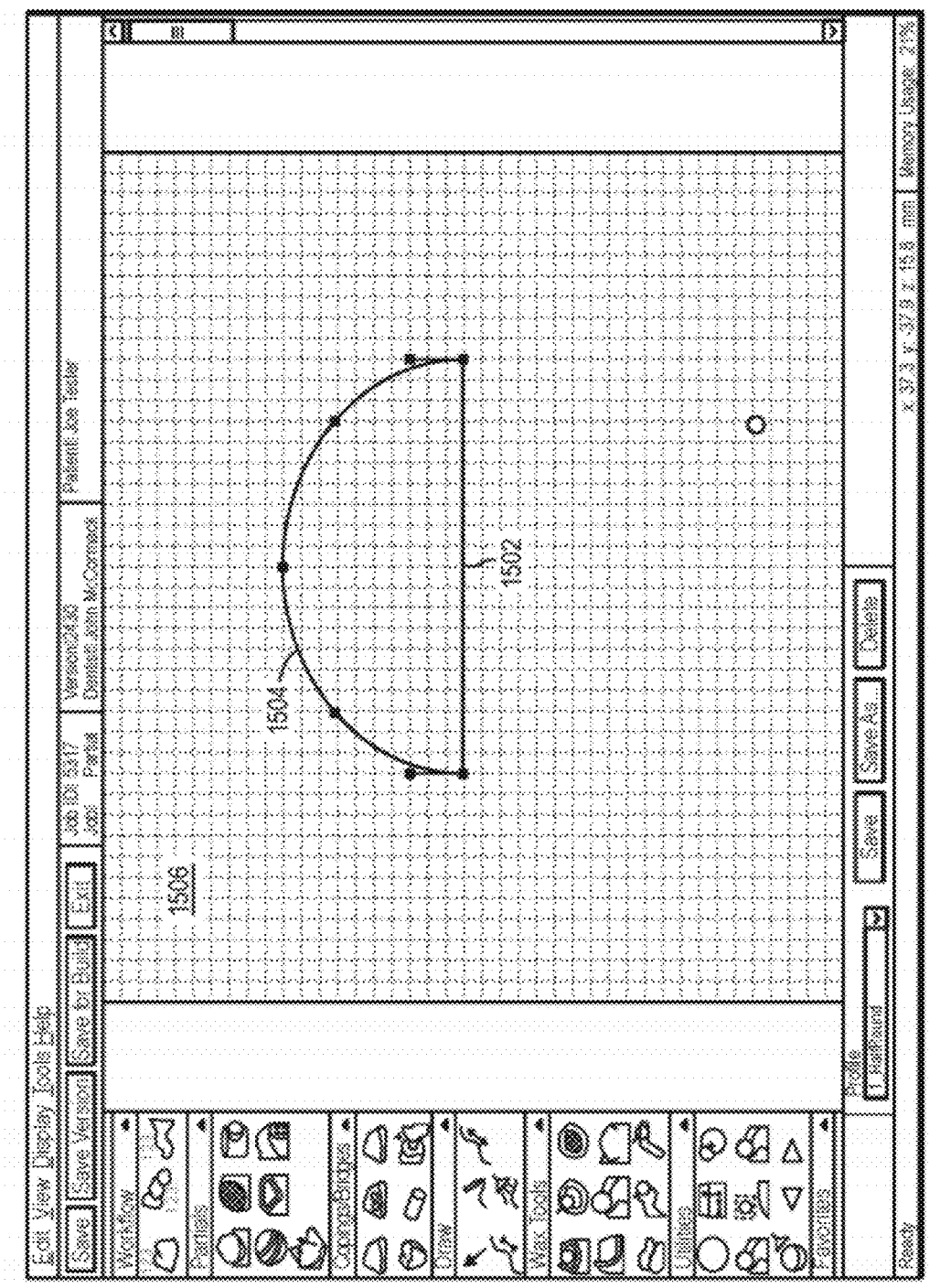
FIG. 15 illustrates a screen capture of a ridge tool in accordance with one embodiment of the invention.

FIG. 15 shows the screen used to edit a profile for the Ridge tools, illustrating a line 1502 and a curve 1504 on a two-dimensional plane 1506. Further haptic controls are provided to adjust the alignment and size of the profile as it is swept along the guide curve. A rotation widget locks the movement of the haptic device in a circular track, allowing the normal orientation of the profile around the axis of the guide curve to be set. A scale widget locks the movement of the haptic device to a linear track, allowing either the width or the height of the profile to be set.

In particular, there are several workflow-specific interactions that are particularly useful to the partial framework designer.

5.5.1 The Clasp Tool

Like all of the illustrative Ridge-based tools described herein, the clasp tool accepts one or more guide curves, two profiles and parameters that define the end taper conditions. The guide curves are entered by the user by clicking to draw a curve on the surface of the virtual refractory model. The profiles are retrieved from system wide preferences and can also be edited by the user for customization.

The taper of a profile along the guide curve can be specified as an End Width of the swept profile, which can be larger or smaller then the corresponding Start Width. The guide curve Width scales linearly from the start to the end. The Height (Thickness) of the profile is scaled in proportion to the Width. Taper can be set uniquely for each component of a clasp. To round off the end of the resulting tapered shape, an end cap is added. This is created by rotating the profile into the surface around the endpoint.

The types of clasps that are supported include Simple Ring clasps, J-shaped clasps, and T-shaped clasps. Simple Ring clasps are attached to the major connector on one end, and are tapered on the other end. The Clasp Tool accepts a single guide curve as input for this type of clasp. There is one single set of taper parameters for this clasp type. J-shaped clasps have 2 legs. The base leg is attached to the major connector. The other end of the base leg is slightly tapered. This distal end is then attached to one short leg with a sharp transition. There are two single set of taper parameters for this clasp type. T-shaped clasps have 3 legs. The base leg is attached to the major connector. The other end of the base leg is slightly tapered. This distal end is then attached to two short legs each of which are tapered more aggressively than the base leg. The Clasp tool accepts 2 or 3 curves as input for this type of clasp, depending on whether the user has drawn the short legs as one or two curves. There is one single set of taper parameters for this clasp type.

The Clasps generally require guide curves which reside on the virtual refractory model. The resulting lofted geometry can rest against the refractory model, or be offset from it at the option of the user.

Figure 16:
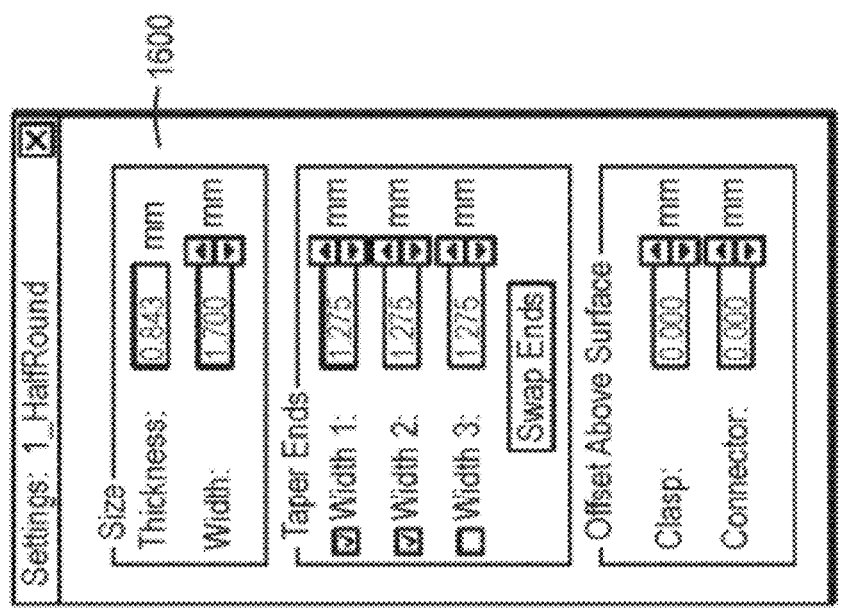
FIG. 16 illustrates a screen capture of a dialog box for clasp parameters in accordance with one embodiment of the invention.

FIG. 16 is a dialog box 1600 illustrating typical parameters defining each type of clasp.

5.5.2 The Finish Line Tool

The purpose of the Finish Line tool is to provide a boundary to the geometry generated by the Mesh tool when creating a partial framework. Typically, the finish line uses a triangular shaped profile, and the resulting lofted shape is generated such that the profiles are swept freely along the guide curve without having the orientation of the swept profile being affected by the surface normals of the refractory model underneath.

Figure 17:
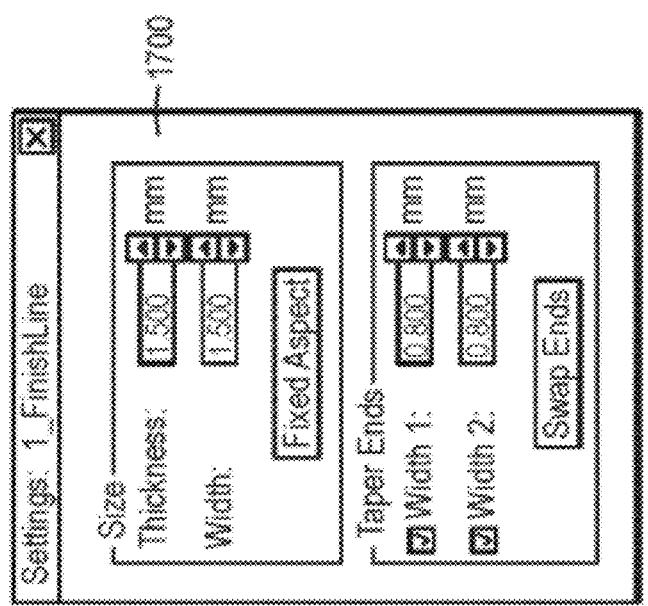
FIG. 17 illustrates a screen capture of a dialog box for finish line parameters in accordance with one embodiment of the invention.

FIG. 17 is a Dialog 1700 illustrating typical parameters that define each type of finish line.

5.5.3 The Lingual Collar Tool

The Lingual Collar tool is used when creating copings and bridge frameworks. The purpose of a lingual collar on a metal coping is to provide structural support for the porcelain that will be built up on top of the metal coping. In general, a coping may have no lingual collar, a partial lingual collar, or a full lingual collar.

Figures 18, 19:
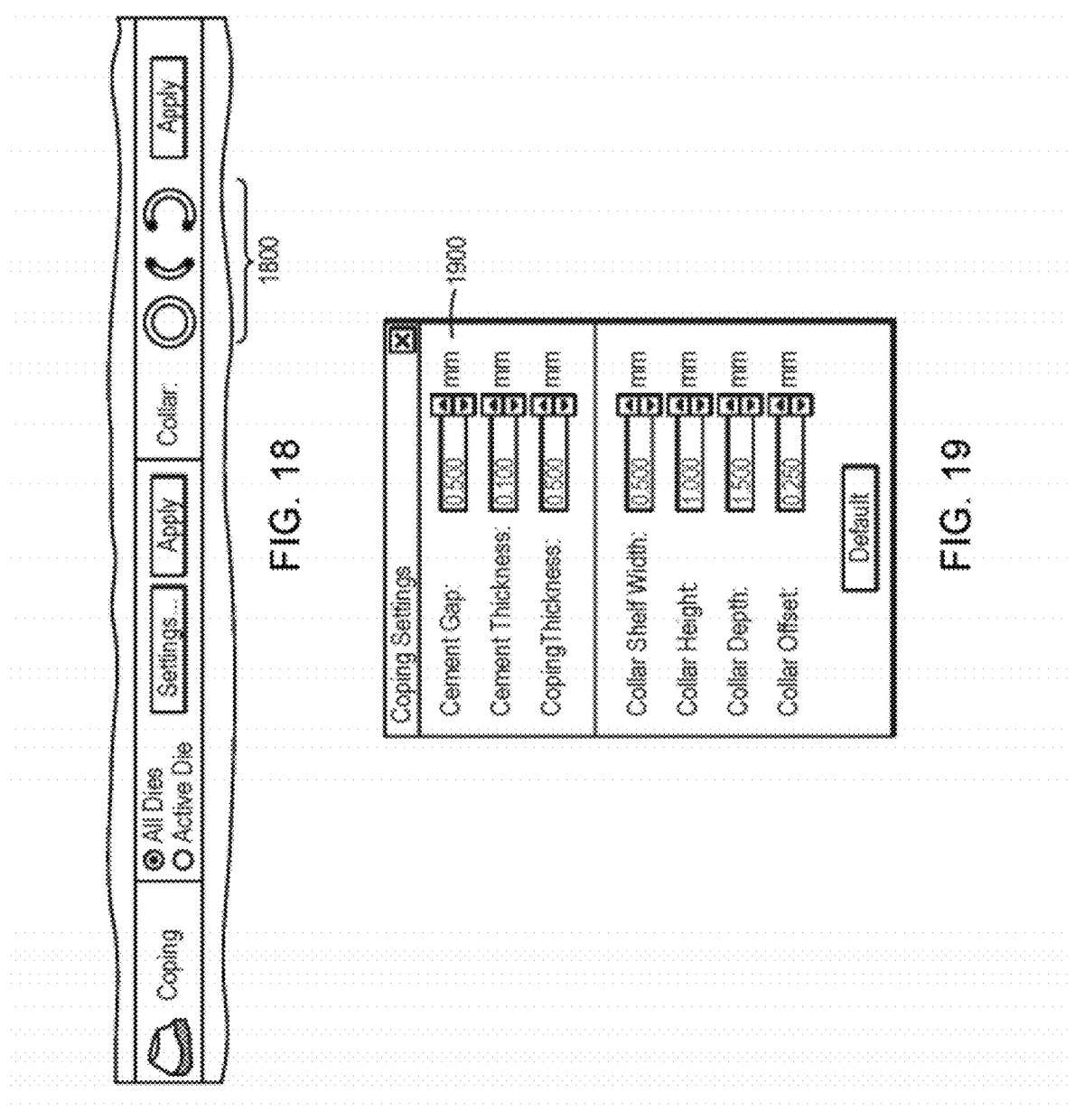

FIG. 18 illustrates these three lingual collar options 1800 for a coping in an illustrative user interface.

For a coping, the lingual collar is always defined such that it blends smoothly into the margin line. For a bridge framework, the lingual collar may be designed to flow smoothly into the connector. The lingual collar is therefore defined by at least one guide curve which governs the bottom of the collar. Optionally, an additional guide curve may be provided to indicate the top of the lingual collar. The cross section of the lingual collar follows a standard shape which may be customized by user-entered parameters. The ends of a partial lingual collar blends down to meet the bottom guide curve, but ends abruptly along the bottom guide curve to form a step.

FIG. 19 shows a Coping Settings Dialog 1900 illustrating the parameters required to define a lingual collar.

5.6 Haptically assisted automatic margin line extraction for copings and bridges For copings and bridge frameworks, the most important feature that must be defined first is the Margin Line, which is a closed loop that follows the preparation line on the prepared tooth.

Generally, the incoming scan represents a "ditched" model, indicating that the plaster stone has been modified by hand to accentuate the preparation line for use by the software application. In this event, the margin line would be clearly detectable. However, in some cases the ditching may be rough or incomplete, in which case the margin line must be intuited manually by inspection.

5.6.1 Possible Inputs to the Margin Line

In one embodiment, where a ditched model is available, the entire scan may be used for a scoped feature line detection algorithm, that may either use a curvature-based mechanism or a 2D Contour detection mechanism based on a path of insertion, knowledge of the dental anatomy, or some other mechanism to derive the margin line from the scan data.

In another embodiment, the user may use the haptic device to paint-select a small strip of geometry on which the margin line resides. This simplified, non-anatomical, geometry is then used by an algorithm to detect a closed loop that represents the margin line.

In a third embodiment, the user may use the haptic device to draw the final margin line. One way to do this is to click points on the margin line while touching the scan model to enter sample points. A NURBS curve may then be fit through the clicked points using a least squares fit mechanism to closely represent the geometry on the scanned model. Fitting a curve tightly to a tolerance may be iterative and can take a long time. Various tricks may be used to improve the interactivity of this step, including using a loosely fit curve during the initial definition state for a coarse fit, and doing a fine fit as a batch process before exiting the margin line definition phase.

5.6.2 Approaches for Automatic Margin Line Detection

In one embodiment, the margin line may be determined by a view-apparent silhouette finding algorithm. Given a path of insertion and a well-ditched model, and a model that is segmented close to the preparation line, the entire margin line should be visible as the silhouette line. A standard silhouette detection algorithm may be applied to the 2D view of this model to find the margin line.

In another embodiment, using a loop of geometry as input, the margin line may be determined by taking sorted cross sections of the model at a number of sample angles with planes that pass through the line joining the centers of gravity of the two polyline loops that define the top and the bottom of the loop of polymesh geometry. The silhouette point of the cross section is identified for each plane, and these points represent sample points on the model that can then be used as input to a NURBS curve fit algorithm to generate a closely fit curve. Alternatively the polyline joining these silhouette points may be used as is as the margin line. Alternatively, a NURBS curve may be generated then projected back to the initial model to find a polyline that lies on the facets of the scanned model.

5.6.3 Illustrative Technique for Determining the Margin Line

An illustrative technique for determining the Margin Line begins with the user manually "swiping" the desired 3D region of interest using the haptic device, and then algorithmically determining the margin line through analysis of the resulting surface curvature.

The user feels the Margin Line with the haptic device and the input through the haptic device generates a band on the refractory model isosurface containing the Margin Line. Based on the skill of the user, the band will be of varying widths around the true Margin Line in the scanned data.

Because of the shape of the surfaces in this anatomy, and the ability of the system to haptically constrain the swiping (e.g., paint-selecting) tool to the desired region, the system provides an effective way in which to specify the band containing the Margin Line.

To automatically detect and extract the Margin Line, an implementation of the "two-loop" method described in Section 5.6.2 is performed.

With the "swiped band" of polygons containing the Margin Line, a reference vector, called the Centroid Axis and a specified origin are created and stored. This is based on the centroid of the boundaries of the top of the band and the bottom of the band. The origin, called the centroid is the midpoint of the centroid of the boundaries of the top of the band and the bottom of the band. The Centroid Axis is obtained by taking the difference vector of the centroid of the top of the band and the centroid of the bottom of the band. The Z Axis is another potential Centroid Axis. A weighted decision algorithm on this pair of vectors is used to define the normal to the band. This axis is called beta.

With beta, a set of planes is generated. These planes are evenly parameterized around the Centroid Axis. This set of planes is used to sample the band to improve the subsequent selection of an improved centroid and Centroid Axis.

Figure 20A:
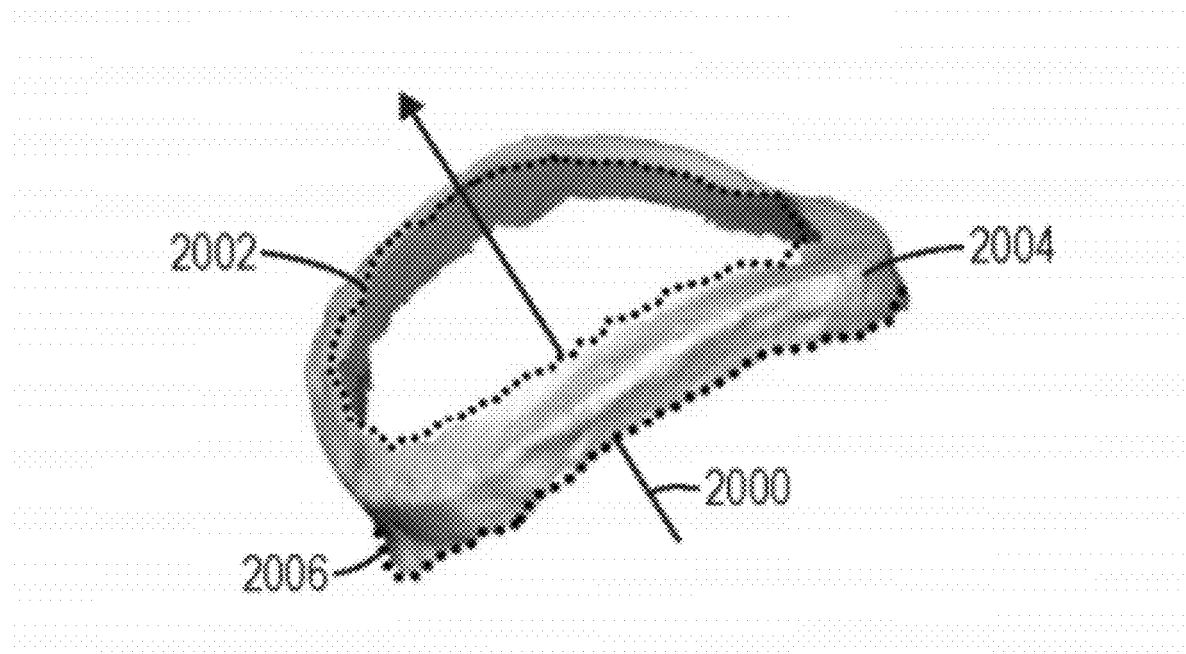
FIGS. 20a-20d illustrate screen captures of margin line generation in accordance with embodiments of the invention.

In FIG. 20a, the Centroid Axis 2000 is shown with the top 2002 of the band 2004 and the bottom 2006 of the band 2004 marked with dotted lines.

With the evenly spaced set of planes, the intersection of each plane with the isosurface is generated. For each plane, the edges intersecting a particular plane form a polyline and are ordered by their connectivity as edges on triangles on the surface. With this ordering, the middle vertex or vertex pair, together with a band about these points is identified and collected. A new top and bottom polyline is created by this set of top and bottom middle vertices. A new centroid is created by taking the centroid of the mid point of the returned middle vertices for each plane; this curve is called the "Provisional Margin Line" (PML). A new Centroid Axis is created from the new top and bottom band of middle vertices.

With the new centroidal axis and centroid, the band is sampled with a larger collection of planes. The band is deliberately over-sampled. The number and spacing of the planes is determined by the number and variation of the edges in the top and bottom loop from the original loops generated before the PML construction, and the top and bottom loops generated for the PML.

Each plane is intersected with the band and the Provisional Margin Line; call this point the PML point. The intersection points of the plane with the band are ordered as before by their positions on the surface.

For both the z Axis and the Centroid axis, a local centroid is calculated by taking the projection of the difference of the PML point and the centroid along the z Axis and the Centroid axis. Local frames are created using these points as origins. With these points, the geometric properties of the ordered intersection points is calculated. These include concavity relative to the local frames.

Also, variation of the normal tangent plane to the surface at the points in the intersection polyline is approximated. Multiple techniques are used to create this approximation. These include approximation of the polyline by a NURBS curve and extracting the resulting geometric information of the curve, in particular the Frenet frame at the points in the polyline. Additionally, the variation of the chordal deviation of the polyline is analyzed.

Figure 20B:
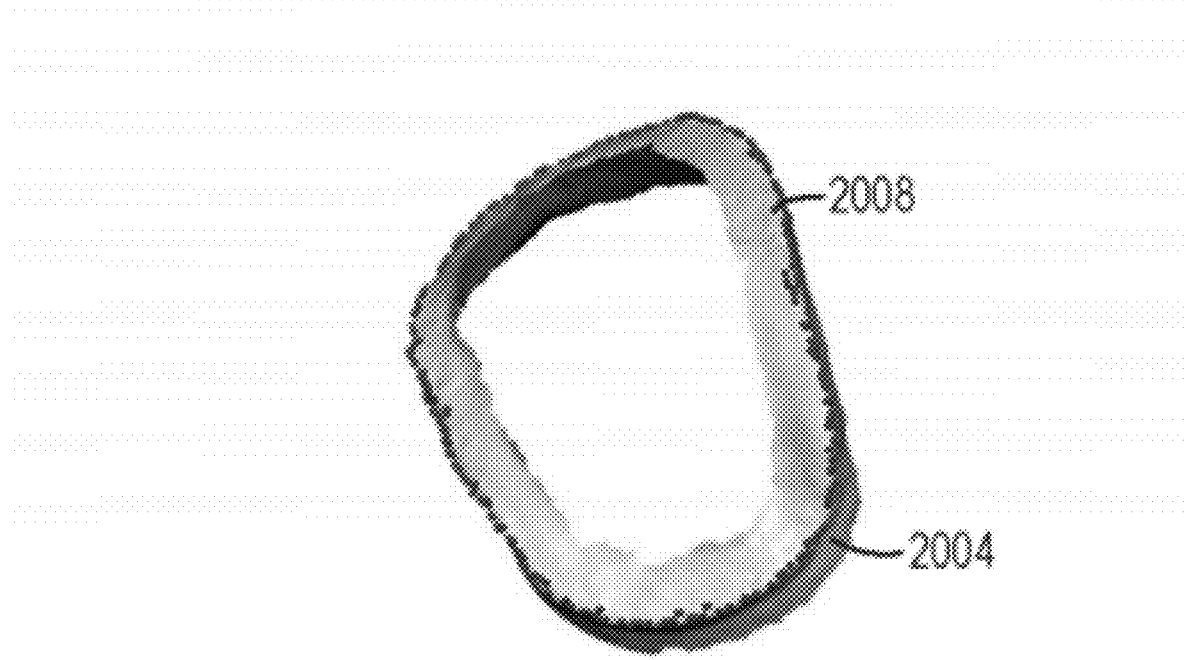

A weighted decision algorithm uses the geometric information collected to select the best and appropriate point amongst the intersection points 2008 generated by intersecting a plane with the band 2004, as shown in FIG. 20b.

Figure 20C:
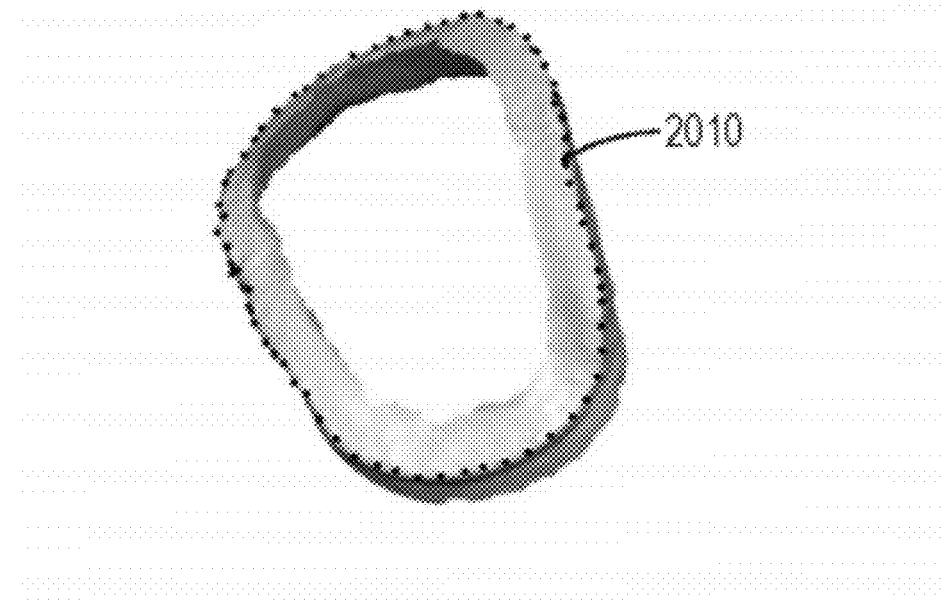

The sampled points 2008 are reduced to a smaller number by a weighted importance sampling of the local density and variance of the points on the polyline algorithm, as shown by the smaller number of points 2010 in FIG. 20c.

Figure 20D:
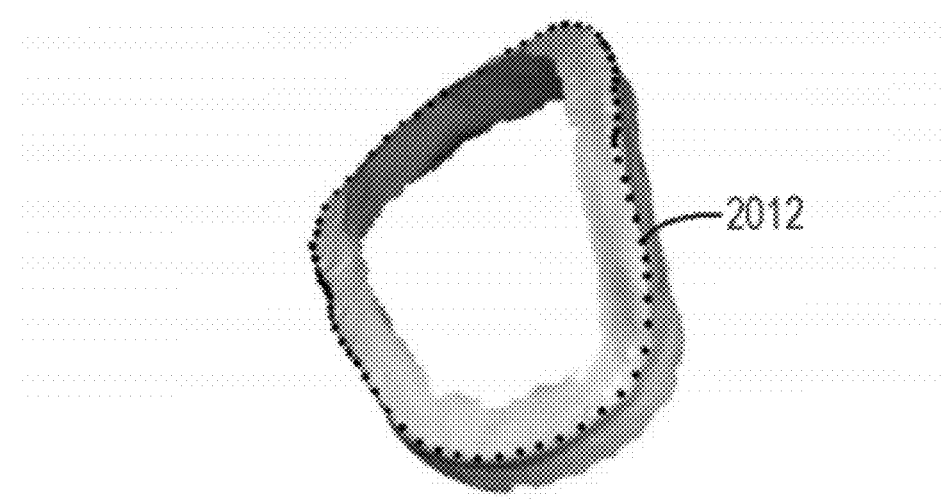

Then, this new smaller set of points 2010 is refined through smoothing the curve by a weighted importance sampling of the polyline and a NURBS knot insertion. The result of these operations is the Margin Line 2012, shown in FIG. 20d.

Once defined, the margin line may also be edited by the user. The haptic device may be attracted to the clicked edit points on the curve using haptic gravity wells. The user may then click a button and drag to move the points, and/or add or remove points to the curve to change the shape of the curve. Other parameters governing fit of the curve may also be modified, including the number of control points, the tolerance of the fit, whether the knot vector is evenly spaced or adaptively determined, etc.

6. Haptic Interaction Tools

Haptic guides and constraints are invaluable as productivity enhancement aids. Haptic guides and constraints such as line and plane constraints may be employed. In addition, dental-specific haptic-graphic widgets are introduced herein to facilitate an intuitive and transparent user interface for dental applications. This includes:

6.1 Choosing the Path of Insertion Using a Virtual Haptic Trackball.

For most all restorations, it is necessary to select a path of insertion, namely the direction in which the restoration will be inserted into the mouth of the patient. For partials, dental professionals often use a device called the "Ney™ Surveyor", which is essentially a desktop device with a movable platform. The vertical direction is the intended path of insertion. The user places the plaster cast of the patient's mouth on the platform, and then rotates the platform slightly while looking at the cast from the side. Once the user finds a path of insertion that minimizes undercuts, a tool with a graphite tip is used to mark the height of contour for further processing.

Figure 21:
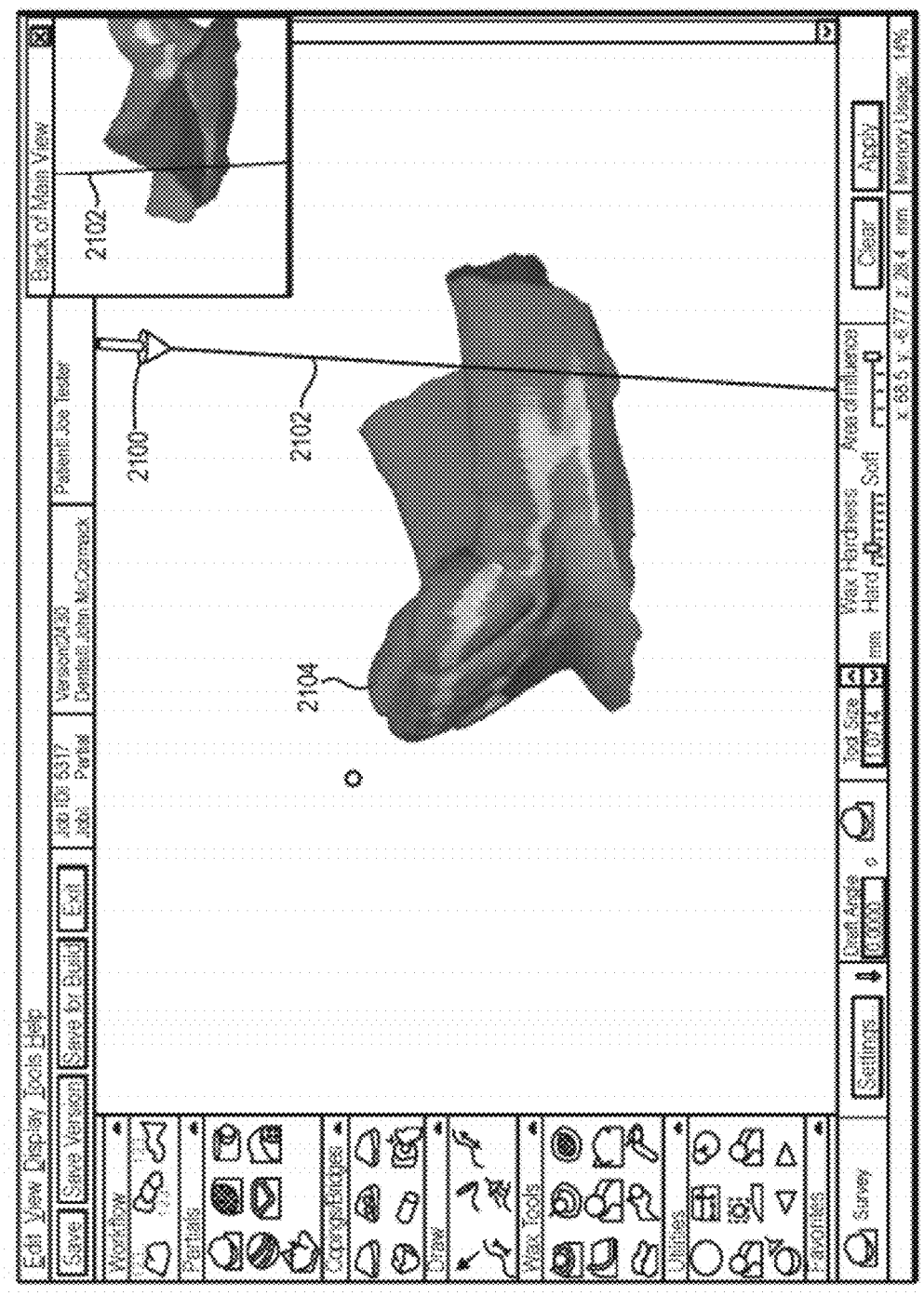
FIG. 21 illustrates a screen capture of a path of insertion in accordance with one embodiment of the invention.

In the illustrative system described herein, an analog for the Ney Surveyor is provided by a haptic Survey tool. In FIG. 21, the path of insertion is indicated with a white arrow 2100 and line 2102. This path defaults to the z-axis of the scan direction. To change the path of insertion with the haptic device, the user first touches a point either on the scanned model of the plaster cast or in the space surrounding it, defining a radius from the center of the model, and then drags in a spherical motion. In this mode, the haptic device movement is constrained to a spherical shell that gives the physical sensation of a Virtual Haptic Trackball, allowing precise rotation of the model on all axes. As the model is rotated, the path of insertion stays fixed with respect to the view, but changes with respect to the model. The resulting effect is much like the behavior of the Ney Surveyor.

Note that this Virtual Haptic Trackball interface can be applied generally to precisely specifying the 3D rotation of any computer model and is not limited to this particular context.

Further note that the described "Virtual Dental Surveying" system can also be accomplished with 2D input such as from a mouse or tablet input.

A similar interaction is used in choosing the path of insertion for copings and bridges. In this type of workflow, the dental professionals often prefer to look straight down the path of insertion so that the margin line for the copings or abutments are clearly visible. However, the haptic interaction remains the same—the user first touches a point and then moves the haptic device to effect a rotation of the model about its center using the Virtual Haptic Trackball technique.

FIG. 21 illustrates the rotation widget in action for choosing the insertion path for a partial framework 2104.

6.2 Translation, Rotation and Scale Widgets for Pontic Placement.

To create a bridge framework restoration, missing teeth are replaced by pontics, and adjacent copings and pontics are joined by connectors. In the physical world, dental professionals use standard wax pontics and melted wax to make these connectors by hand.

In the illustrative system described herein, a library of virtual pontics and connectors are provided, whose shape is based on the particular tooth involved. Furthermore, a haptic widget is provided that allows the user to move and reorient individual pontics or connectors by touching them, depressing a button, and dragging them in either x-y-z translation mode, rotation mode, or free 6 degree of freedom (DOF) mode.

Figure 22A:
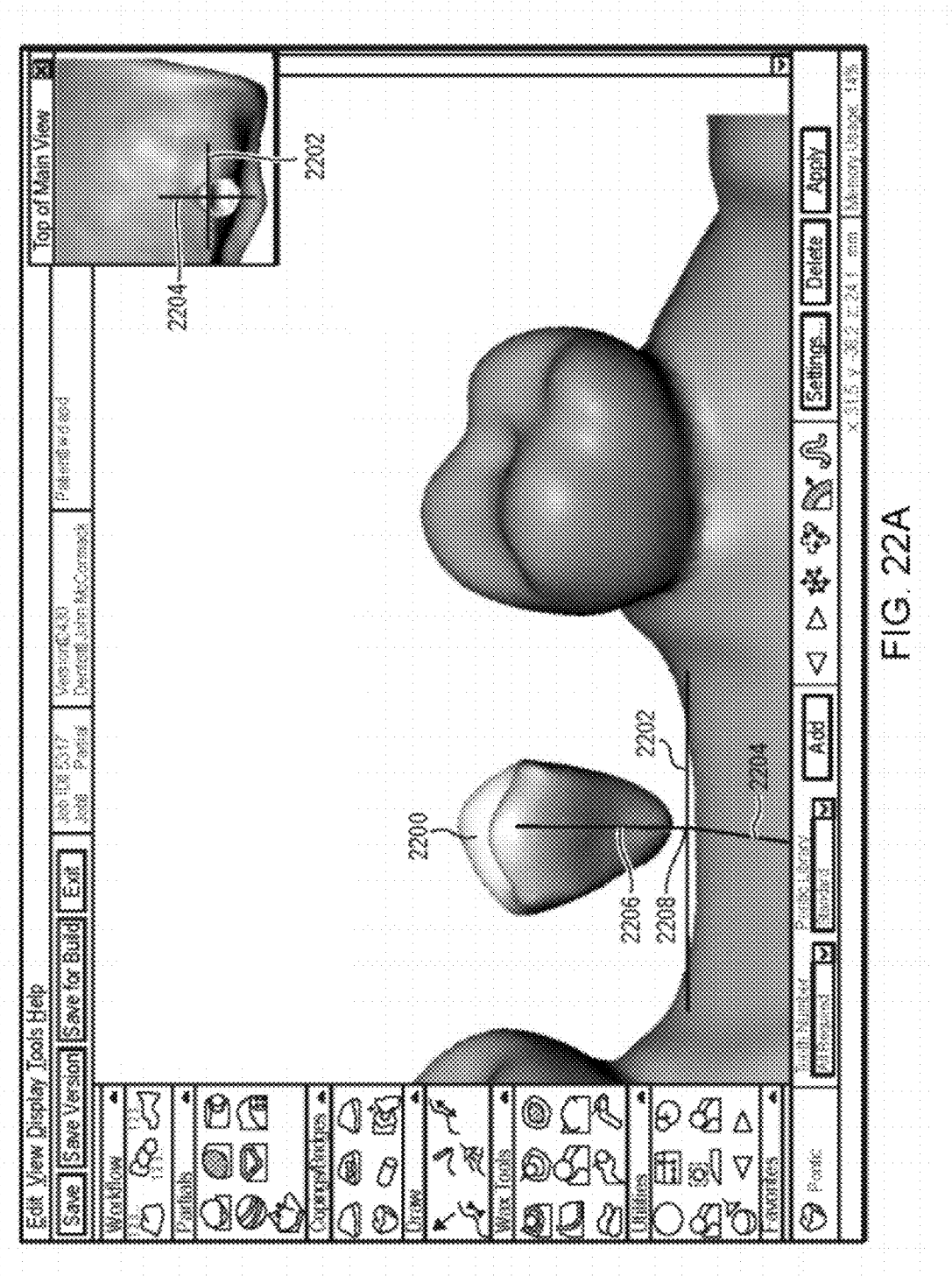
FIGS. 22a-22b illustrate screen captures of a rotational widget in accordance with embodiments of the invention.

FIG. 22a illustrates the translation/rotation widget being applied to a pontic 2200. An x-axis 2202, y-axis 2204, and z-axis 2206 show the local x-y-z coordinate system and the crossing point 2208 shows the local origin for rotations.

Additionally, the placed pontic 2200 and connector pieces may need to be resized or stretched. The illustrative system provides a haptic widget in which the user touches the piece and then begins dragging. Depending on the location where the piece is touched and the direction in which the user moves, the piece can be scaled non-uniformly in one of its three local x-y-z coordinate directions.

When the piece is touched, the direction of scaling is chosen based on the surface normal vector. Whichever major local axis the normal is closest to in alignment, becomes the scaling axis. As the haptic device is moved, it is locked to a linear track along the scaling axis. For finer scaling control, a Nudge modifier slows down the scaling action relative to the haptic device movement.

Figure 22B:
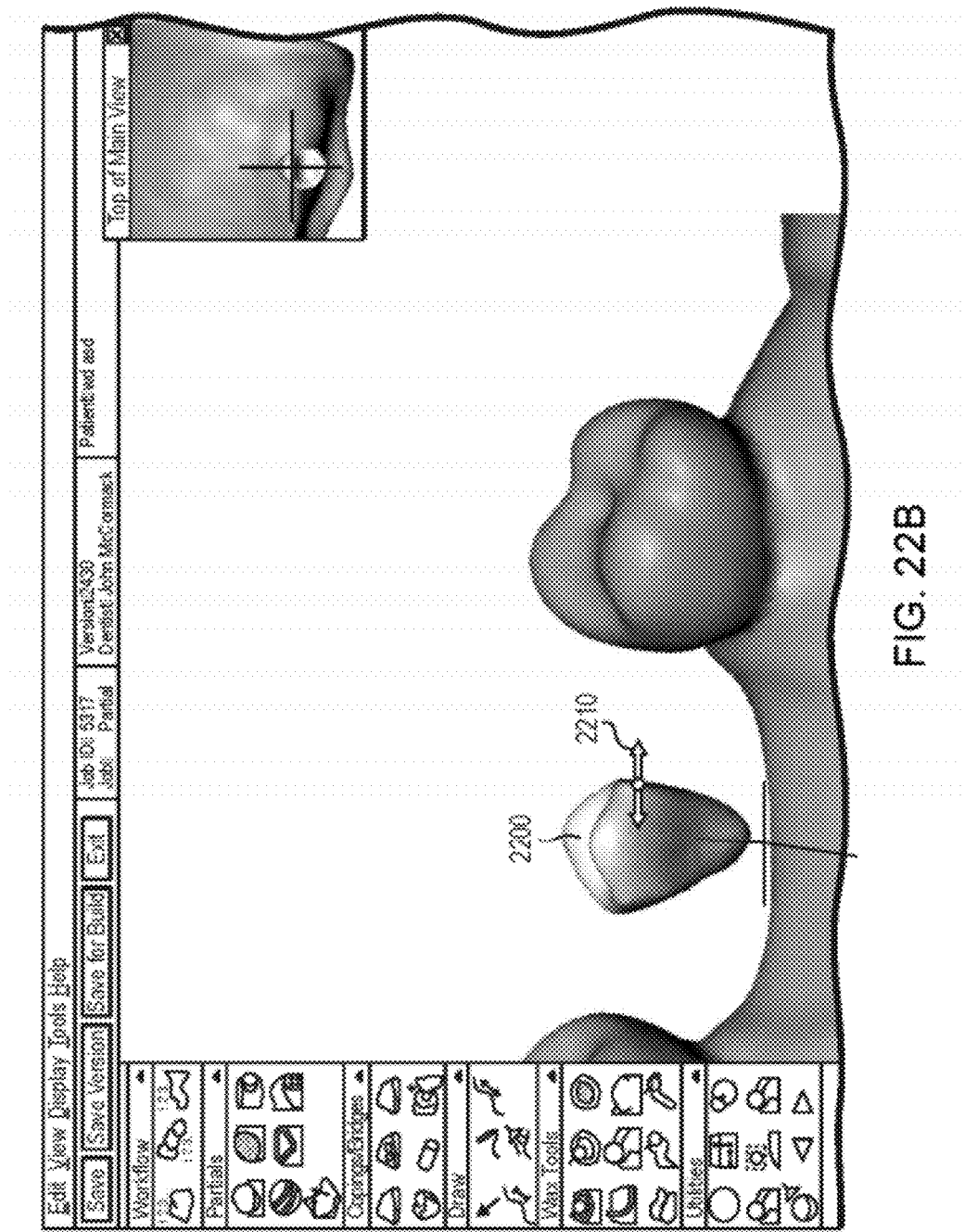

FIG. 22b illustrates the scale widget being applied to a pontic 2200. In this case, the piece was touched on a side facing the X direction, so the arrows 2210 are drawn parallel to the x-axis 2202.

6.3 Haptic Guides

Haptics may be used in checking surgical guides, for example, in the alignment of implants and bars, to help set drilling angle,s and/or to produce guide fixtures for use in surgical fixtures.

Embodiments of the current invention describe systems and methods for enhancing execution of dental procedures by coterminously constructing either a guide fixture or a surgical plan with a patient-specific prosthetic. This guide fixture or surgical plan may serve as instructions for a dentist to optimize the final placement of the prosthetic in the patient. A haptic interface may then be utilized to confirm the alignment of the guide between the patient situation and the designed prosthetic. Additionally, the haptic interface may be utilized to directly confirm the match between the patient situation and the designed prosthetic. In much the same way that a dentist tests the fit of a partial framework or crown by pushing the prosthetic with his fingers and feeling the resulting motion, a haptic interface may be programmed to provide this interaction in a virtual setting.

Furthermore, if a surgical plan, such as the drill path for an implant, is produced along with the patient-specific implant, the surgical plan may be implemented directly with a haptic guide wherein the dentist's hand is lead directly by his instruments to drill along the correct path. One embodiment for this invention is to modify a typical dentist's drill to include either actuators (such as motors) or brakes to limit the extent of the drill movement at each joint; encoders or other position sensor so that the location of the drill tip is known in 3D space (let's call this modified drill the 6-DOF Haptic Drill); and a patient registration step wherein the 3D relationship between the drill, patient and surgical plan is defined.

Patient registration may be accomplished by touching landmark points available in the surgical plan with the drill in the patient situation; by the explicit introduction of fiducial points affixed to the patient that are available in the surgical plan; or through a "real-time" method wherein a sensor near the end of the drill and matching software is utilized to derive the correspondence between the sensor data and the surgical plan to be performed.

This haptic-guide concept may be broadened by removing the requirement for a designed prosthetic component. In the case of implant surgery, the dentist's skill in choosing an off-the-shelf implant in conjunction with executing the proper surgical plan to optimize the use of available bone tissue within the jaw is of the most importance. In this case, the 6-DOF Haptic Drill may, through a "form at rest" control strategy, help the implant surgeon execute the necessary drilling by haptically enforcing the alignment of the drill orientation along a specific path and by providing information for the depth of penetration of the drill tip.

The "form at rest" control strategy has been developed using a haptic device-such as the Premium 6-DOF haptic device manufactured by SensAble, where, conceptually, the drill tip is located at the haptic interface point—and is a combination of gravity compensation and maintaining the user's handle orientation when the device is released. General free-space motion is allowed until a preprogrammed constraint, haptic wall or other guide path is approached.

Haptic guides may be used for tooth preparation, implants, and other dental surgical procedures. These guides may take two forms: a guide fixture to be placed into the patient's mouth before a procedure is undertaken, or as a haptic guide in which a typical dentist's drill is modified to include (1) actuators and/or brakes to limit the extent of the drill movement, (2) encoders or other position sensor so that the location of the drill tip is known in 3D space, and/or (3) a patient registration step wherein the 3D relationship between the drill and patient is defined. Patient registration may occur in real-time by using a sensor near the end of the drill and matching software that can derive the correspondence between the sensor data and the procedure plan to be performed.

Haptic guides may also be used for bite registration. Many good-fitting dental restorations, such as for crown/bridge, require methods to provide for proper occlusion, where teeth on the maxillary and mandible jaw meet. Haptic guides for bite registration may permit a lab technician to model crown/bridge restorations while feeling the antagonist. For example, the lab technician may use a tool to deform a cusp on the tooth that he or she is designing, while feeling the antagonist, thereby placing the cusp to contact at the opposing fossae or other user-defined contact point. This method may provide an extremely intuitive and fast interface for such design.

Voxels and/or haptic feedback may also be used for dynamic bite articulation. Many dental restorations are designed and tested using a physical bite articulator, where the upper and lower jaw may interact with one another allowing the lab tech to provide designs with proper occlusion or fit. Using haptics, a user may manipulate the lower jaw against the upper jaw to physically feel the virtual fit, in a fashion that mimics a physical model and articulator.

In addition, sensors may be used to measure a patient's physical articulation and/or jaw movement. These sensors may measure the movements and also the timing and forces as the patient clenches his or her teeth together. This information may then be used to automatically modify the restoration design to account for dynamic articulation. For example, in crown and bridge, "freeway" is extra space that is provided in the tooth design to allow for natural chewing, protrusive, excursive and other movements. Using dynamic bite articulation with voxel and/or haptics, the lab tech may design a crown or bridge that fits into the patient's mouth, the first time, with minimal grinding and adjustment by the dentist.

7. Multiple-Representations to Balance Accuracy Versus Scalability

The voxel based 3D representation used for enabling the virtual refractory and virtual wax modeling paradigm has inherent strengths and weaknesses. The strengths include the ability to readily emulate real-world modeling processes through the use of volumetric union, intersection, and subtraction booleans as well as blending and deformation operations. However, unlike a real-world material, a voxel representation has an inherent spatial resolution limit, which affects both the minimum feature size and the precision of the surface location. The memory and processing requirements typically increase exponentially as resolution increases. In comparison, a boundary representation (B-rep) such as polygonal surfaces or spline surfaces may represent arbitrarily small features and a precise surface location with comparatively less memory and processing requirements, yet do not offer the same ease as a voxel representation for emulating real-world modeling processes.

An important part of the coping and bridge modeling process involves achieving a precise fit to the margin line(s). A voxel representation would need to be sampled at a very high resolution to satisfy the 10 micron scale manufacturing tolerances necessary for the margin line. Using this high of a resolution would be prohibitive to providing an interactive and time-efficient modeling experience for a dental technician. By contrast, the illustrative system uses multiple representations. This allows a sufficiently accurate spatial resolution for the voxel volume to represent the majority of the designed part while supplementing the surface representation with more accurate boundary representation geometry near the margin line. The output of this process is a triangulated surface in which much of the surface is based on an isosurface extraction from the virtual wax volume and just the triangles on the interior surface of the designed part(s) near the margin(s) are obtained from trimming the scanned patient geometry from our virtual refractory model. Optionally, tessellated spline surfaces may be used to define the exterior surface near the margin.

The process for preparing, trimming and stitching the virtual wax can be performed as follows. It may be applied for one or more margin line junctions between the coping or bridge and the patient scan data. The input to this process is triangulated patient scan data for each coping with a corresponding precisely defined margin line curve. As a preparation step, the margin line curve is used to trim the triangulated patient scan data to yield a clean and precise surface boundary. The excess geometry from the scan data below the margin is discarded. Additionally, the refractory volume is subtracted from the wax volume to produce an isolated wax part of the coping or bridge. The portion of the surface near the margin is not guaranteed to be smooth and free from topological defects. Therefore, a small extruded surface perpendicular to the path of insertion is made using the margin line which is swept downwards to produce a volume. This volume is subtracted from the wax part to eliminate stray geometry near the margin and to produce a clean surface for trimming. Additionally, a volumetric flood fill selection is performed to identify and remove all stray portions of virtual wax which are disjoint from the wax part.

Once the virtual wax and scan data geometry have been prepared, a trimming process is used to isolate portions of geometry near the margin from both the virtual wax and scan data. A trimming surface is formed from the margin loop based on sweeping a circle profile. The radius of the circle profile is selected based on the desired size of the transition region between triangulated voxel data and triangulated scan data, which is typically the size of a few polygons wide. The swept circle profile surface is computed as a lofted NURBS surface which is then tessellated. The trimming surface is used to both trim and eliminate defects from the triangulated wax isosurface extraction while also trimming the patient scan data to produce a strip of more precise surface data for a highly accurate interior margin region. The same trimming surface is applied to both surfaces to ensure consistency and continuity of the result. A triangle flood fill is used to gather the exterior and interior trimmed surfaces while discarding the portions of the virtual wax surface near the margin. Additionally, a flood fill is used to gather the strip of surface from the scan data which is closest to the margin loop.

The final stage of processing is to stitch the trimmed exterior and interior virtual wax surfaces to the scan data surface to produce a watertight 2-manifold triangulated boundary representation of the part to be manufactured. The boundary polylines from the interior, exterior and scan data strips are identified and paired based on proximity. Then these paired polyline boundaries are connected using strips of triangles.

7.1 Edge Thickness

Figure 23:
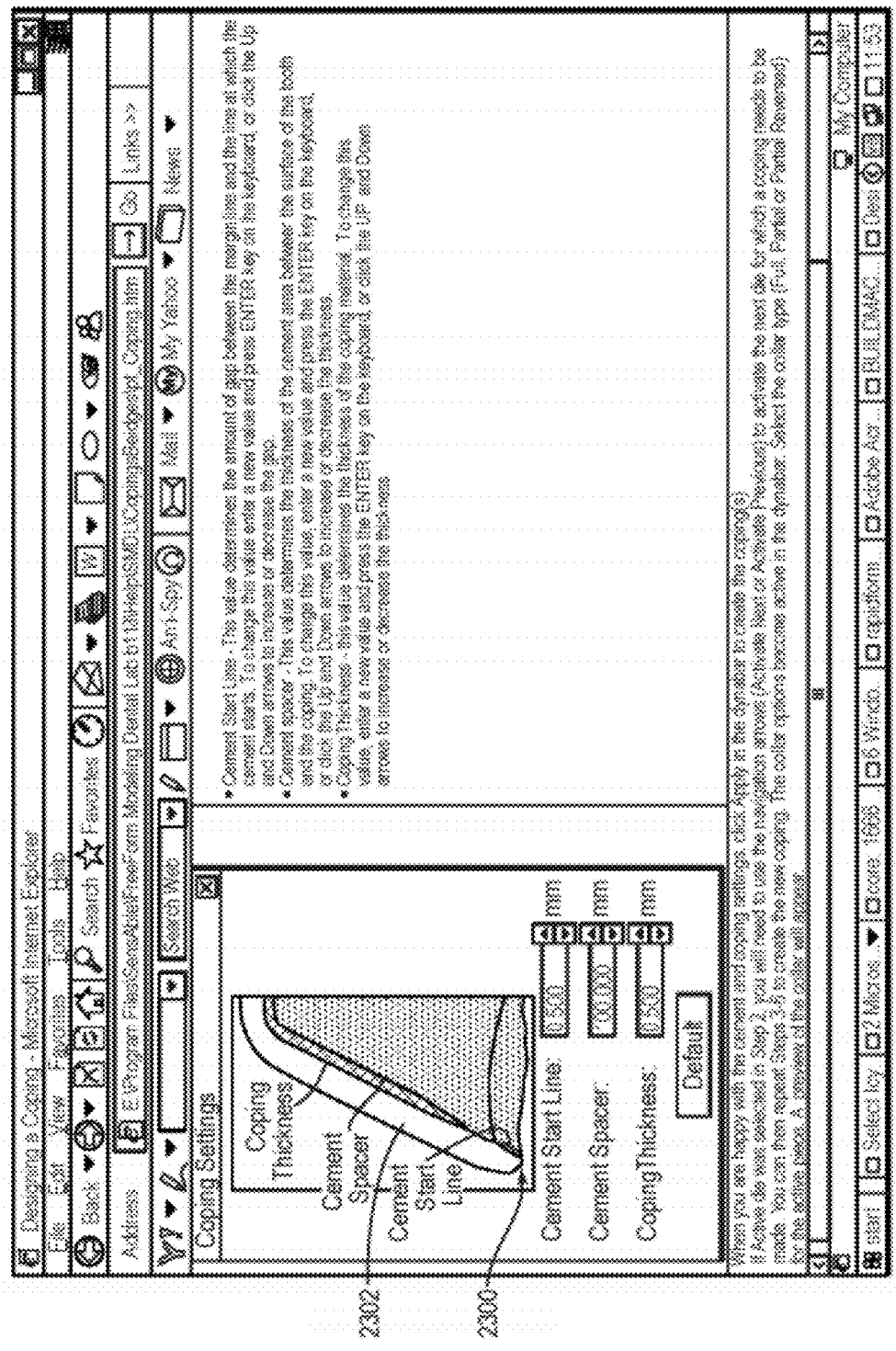
FIG. 23 illustrates a screen capture of a knife edge in a coping in accordance with one embodiment of the invention.
Figure 24:
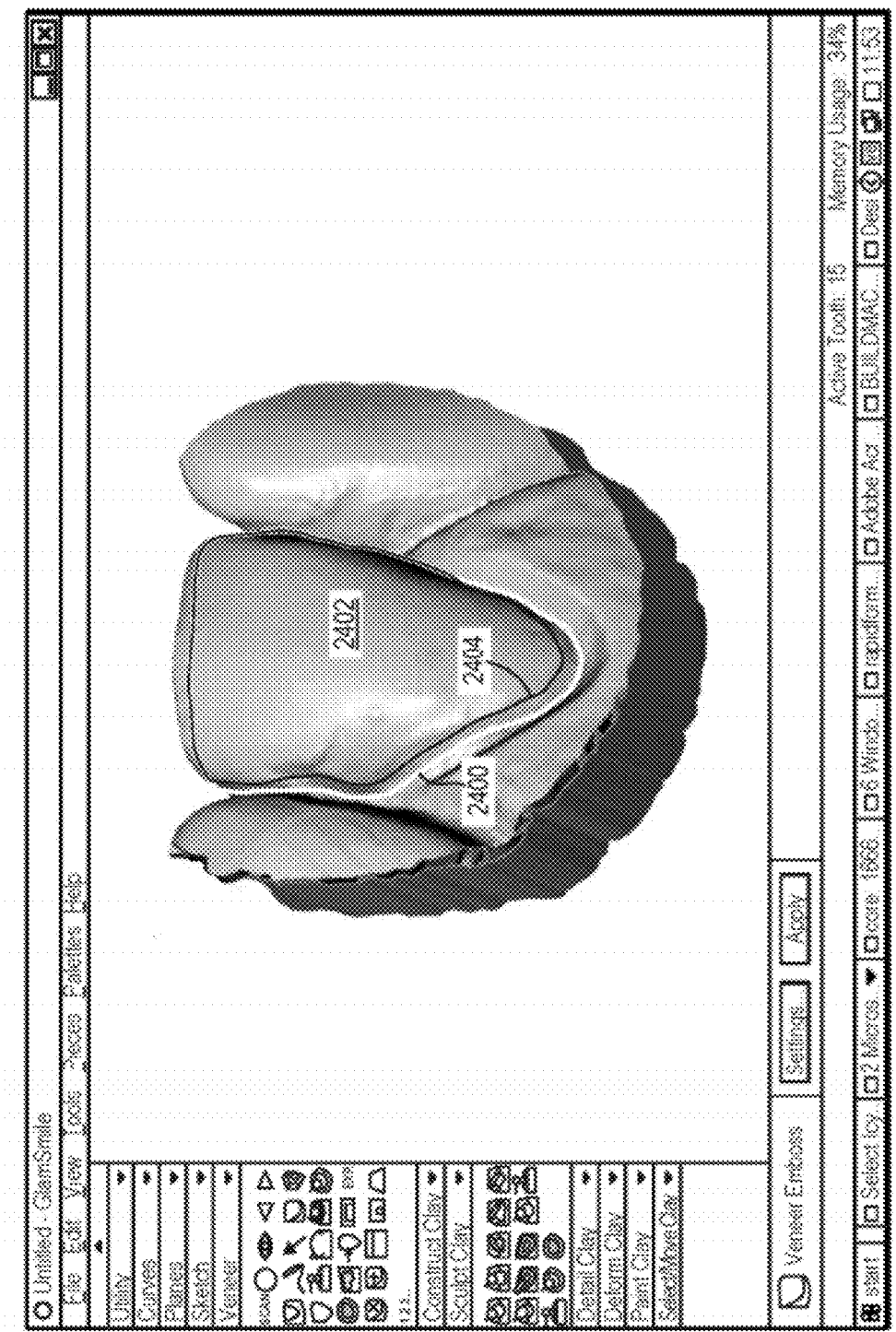
FIG. 24 illustrates a screen capture of a knife edge in a veneer design in accordance with one embodiment of the invention.

Additional parameterization and geometrical construction may be performed to better utilize the capabilities of rapid prototyping (RP) machines for dental design. RP machines that can directly print three-dimensional parts are manufactured by, for example, 3D Systems, Objet, and other companies. Because these RP machines have a finite amount of resolution, small, thin features, and/or knife edge designs (where the edge thins down to zero thickness) may exhibit mismatches between the designed part and the physical output of the Rapid Prototype machine. Copings and veneers may terminate in such a knife edge where, ideally, the edge thins down to zero thickness. FIG. 23 illustrates a knife edge 2300 in a coping 2302. Similarly, FIG. 24 illustrates a knife edge 2400 in a veneer design 2402.

Figure 25:
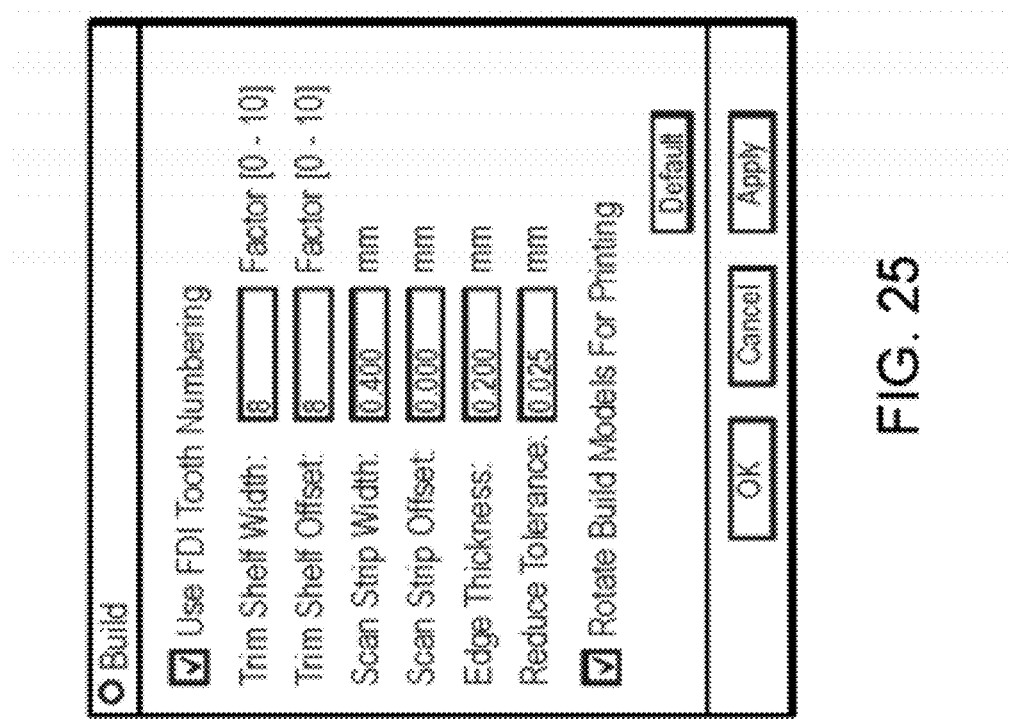
FIG. 25 illustrates a screen capture of a edge thickness dialog box in accordance with one embodiment of the invention.

In both the case of the coping and the veneer, the location of the knife edge may be defined by the anatomical margin line of a tooth. An additional parameter for "edge thickness" may be added that constructs a geometric "shelf" at the margin line 2404 that, as shown in FIG. 24, may have a width of 0.2 mm. This value may be variable to match the resolution of different RP machines and any other constraints in the dental design. FIG. 25 shows a configuration dialog box 2500 with the new parameter edge thickness.

Figure 26:
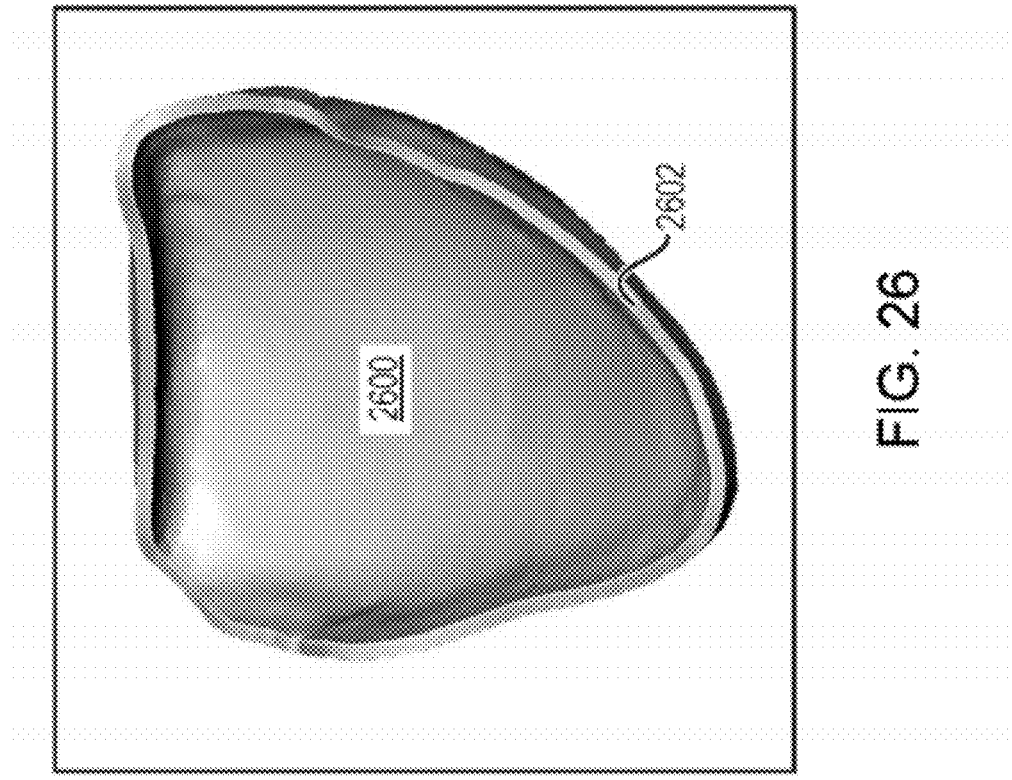
FIG. 26 illustrates a screen capture of a finished veneer in accordance with one embodiment of the invention.

Finally, FIG. 26 shows a finished veneer 2600 with an edge thickness 2602 of 0.2 mm. Because of the large amount of zoom available in the design software, the shelf looks big visually, while the actual physical size may be less than a millimeter. The shelf may be oriented to be mainly perpendicular to the original surface of the designed veneer.

Furthermore, while the above description of embodiments of the invention is in terms of designing copings and veneers, it should be appreciated that this utilization of the margin line with an additional edge thickness parameter may be applied to the geometric construction of other dental prosthetics or implants as well.

Figure 27A:
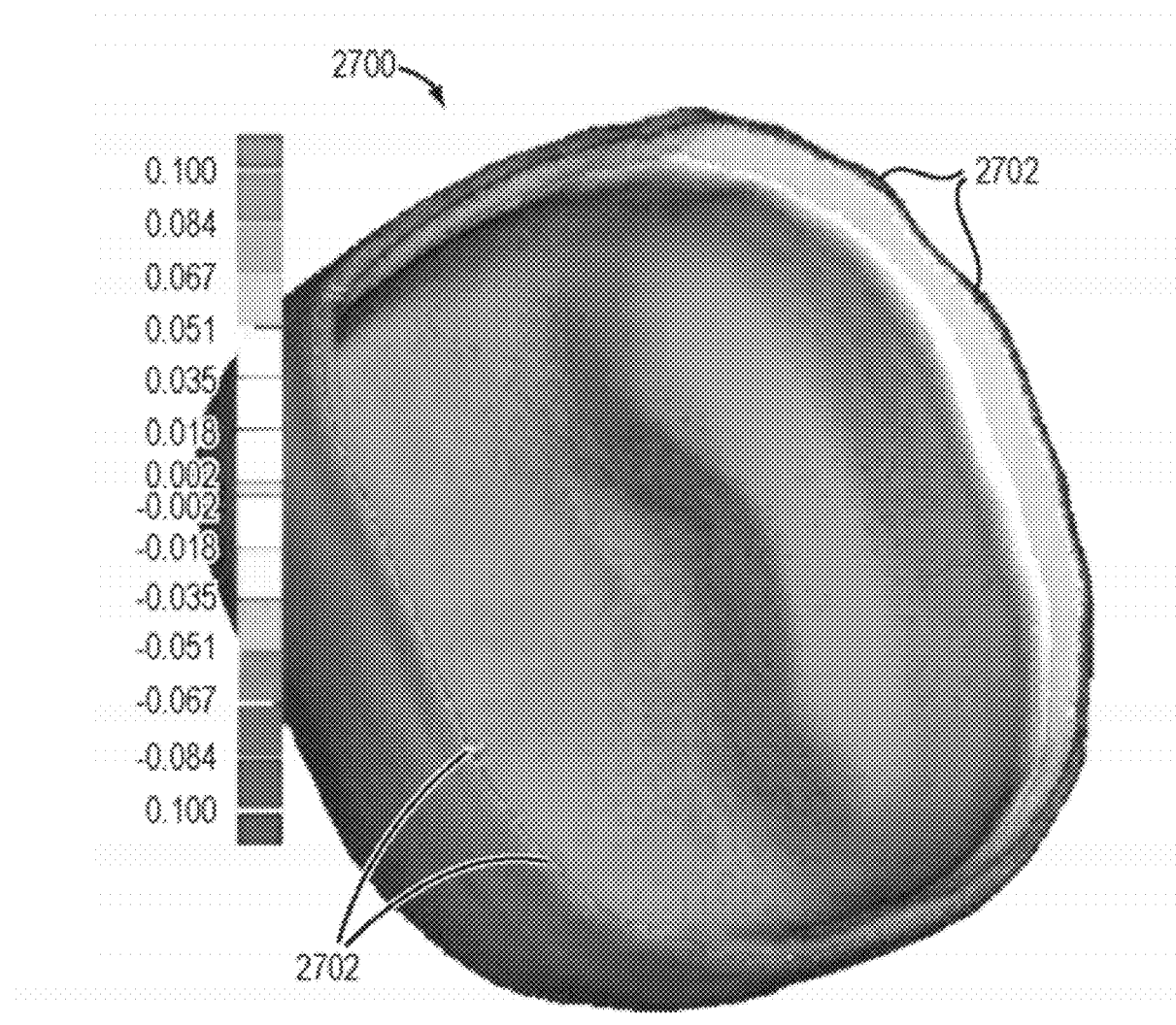
FIGS. 27a-27c illustrate screen captures of mixed representation usage in accordance with embodiments of the invention.
Figure 27B:
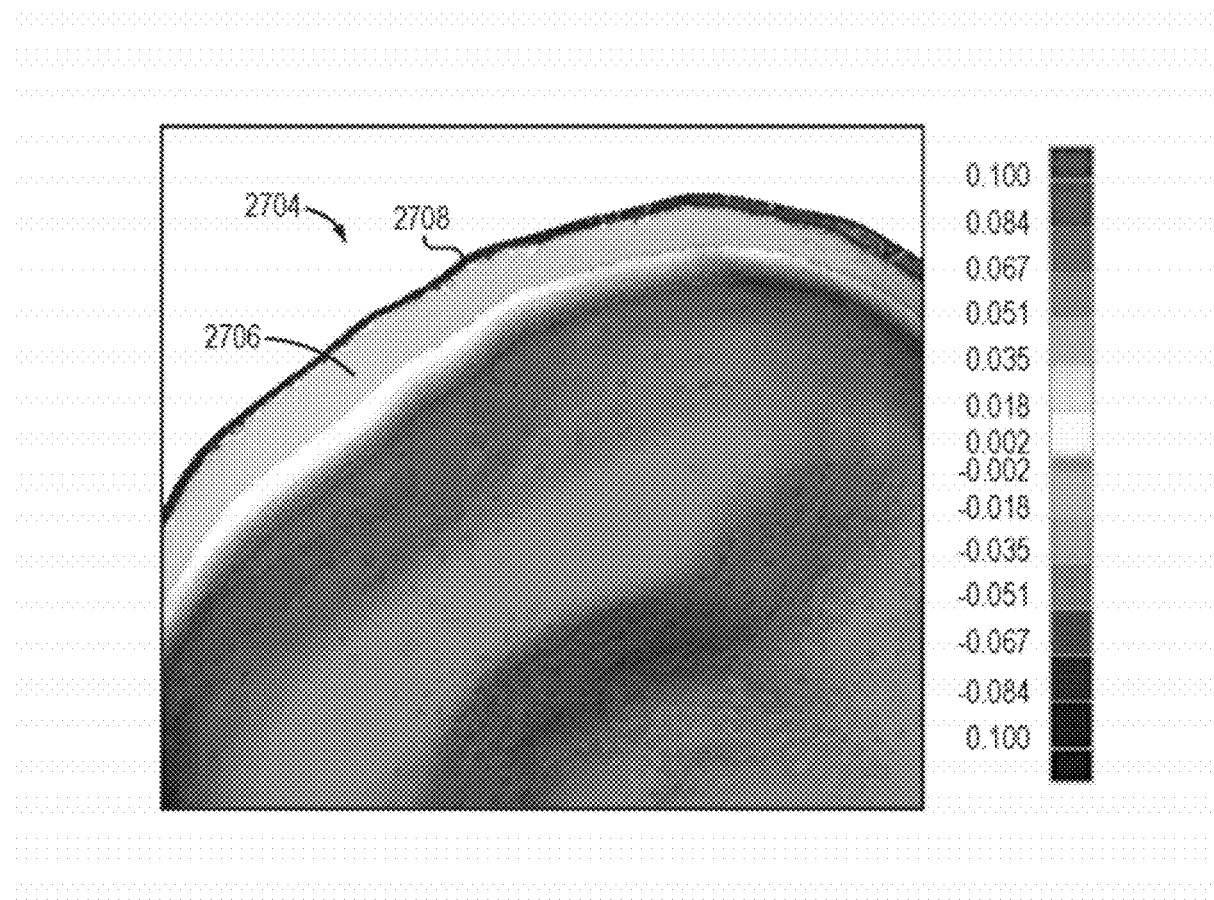
Figure 27C:
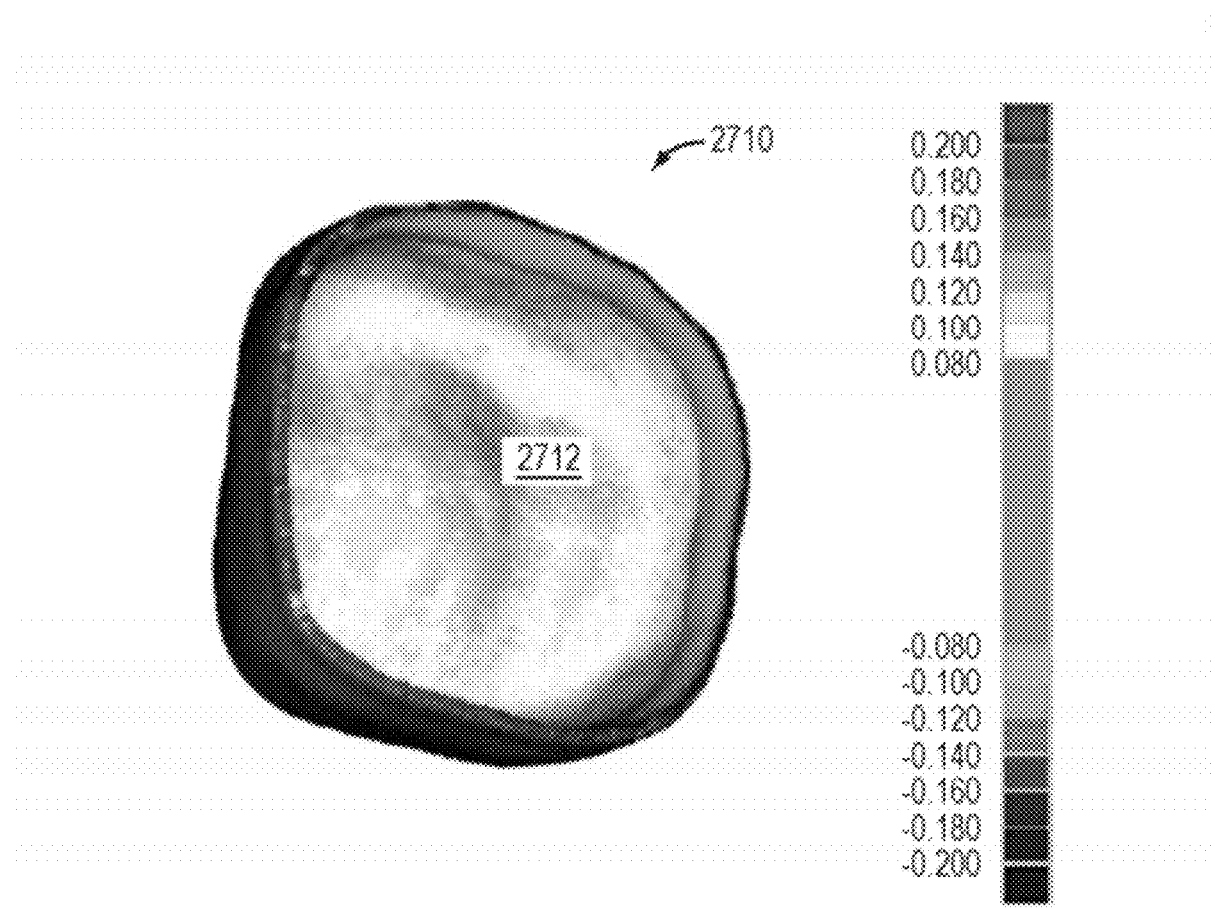

FIGS. 27a to 17c demonstrate mixed representation usage, and show the precision of the margin line and cement gap. FIG. 27a shows the margin for a voxel-based coping export 2700 (see areas 2702 near the edge of the export 2700 which show discrepancy with prepped tooth). FIG. 27b shows the margin for a scan-data stitched coping export 2704 (showing that the area 2706 near the margin 2708 is very precise). FIG. 27c demonstrates that the voxel representation 2710 accurately represents the cement gap 2712 at 100 microns.

8. Preparing a Tooth for a Coping

A stump of a prepared tooth may be shelled to create a coping or bridge substructure that fits over a prepared tooth, with a cement, glue, or bonding gap. A voxel representation may be used to create the coping or bridge substructure with the glue gap.

Figure 28:
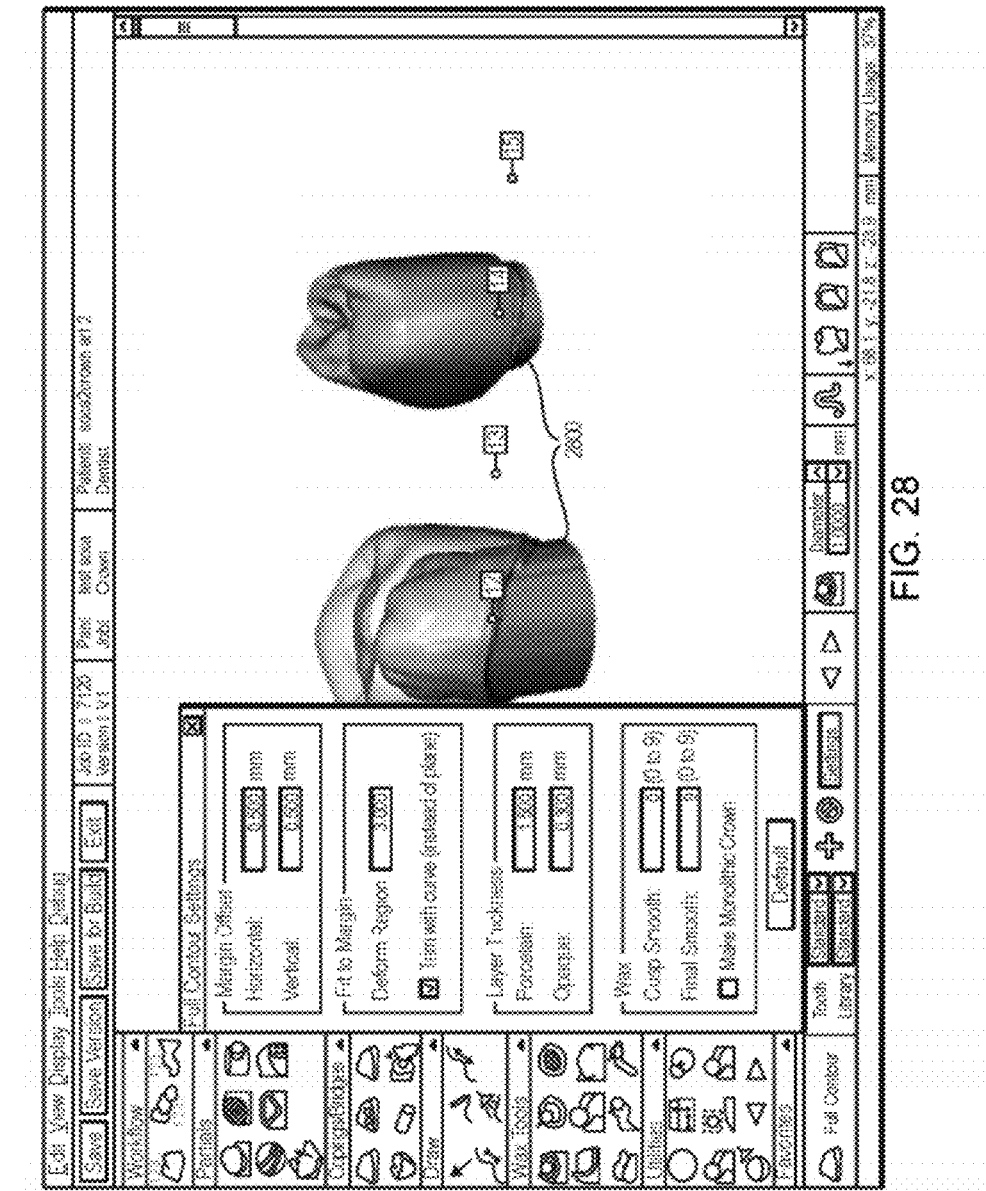
FIG. 28 illustrates a screen capture of a coping with a voxel offset in accordance with one embodiment of the invention.

A voxel offset may be used for anatomical copings, as shown in FIG. 28. The voxels may be used to automatically derive an anatomical coping 2800 from a full-contour tooth design. The anatomical coping may be derived at an offset specified by the user. The anatomical coping may optionally include a user-specified gap for an opaque layer (usually a light-colored material to hide a darker-colored coping so that a porcelain overstructure looks natural with no dark spots). Unlike a simple, thimble-like coping, an anatomical coping may provide a stronger understructure, and allow for application of a uniform porcelain overstructure thickness, which may reduce stress fractures and cracking.

9. Technician-Assisted Design

A technician may select preferences according to an order placed by a particular dentist. The system may provide user-defined preferences to set commonly used parameters. These preferences may be set to the user, the lab, and/or the dentist. When a new case is started for a particular patient, the appropriate preferences may then be automatically applied to affect the final restoration design. For example, a dentist may prefer clasps of a certain profile and dimensions, or a restoration with a tight or loose fit. When a prosthetic for one of that dentist's patients is designed, these preferences may be automatically inherited.

Figure 29:
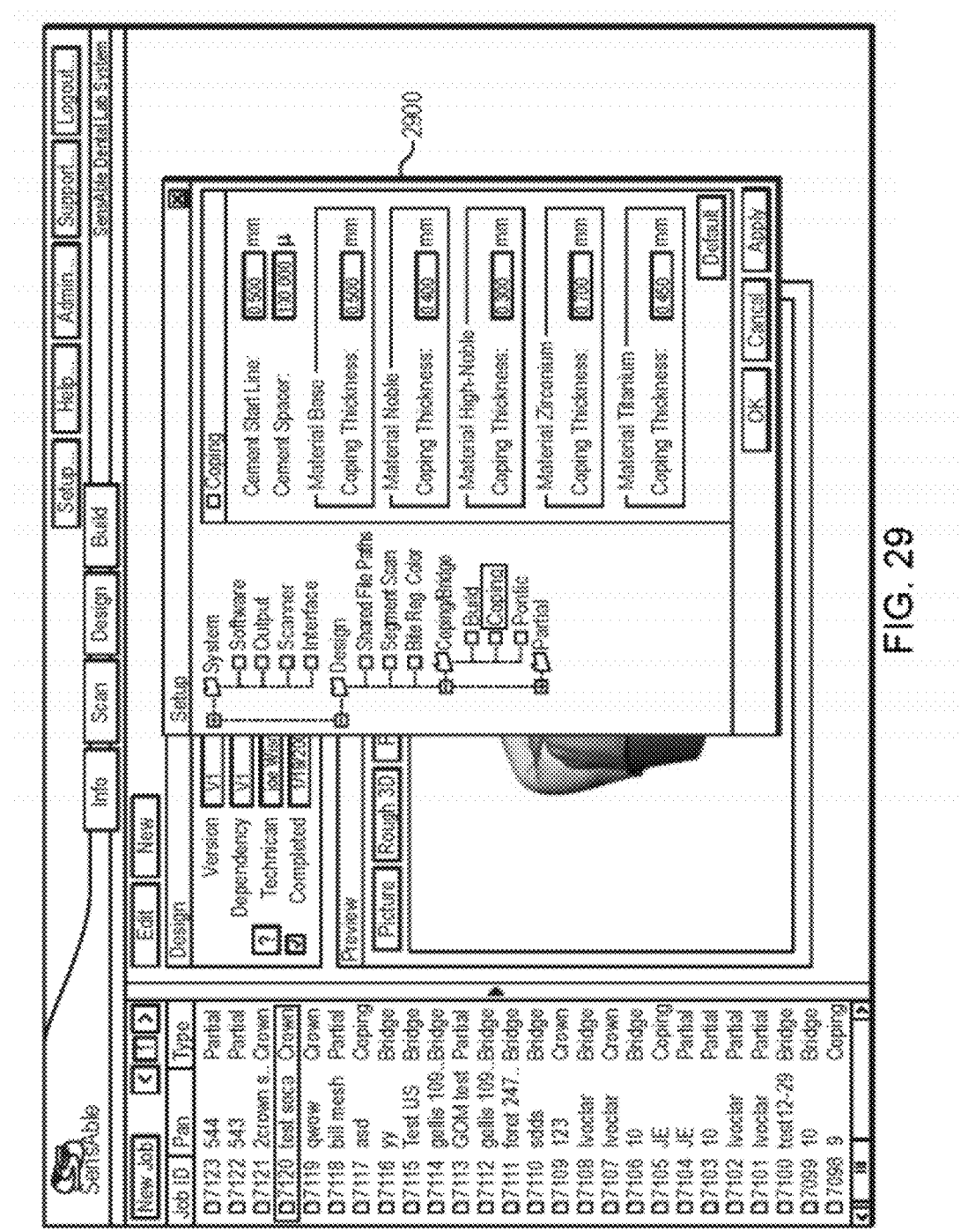
FIG. 29 illustrates a screen capture of a preferences dialog box in accordance with one embodiment of the invention.

The technician may select preferences 2900 according to which kind of material is to be used in a dental restoration, as shown in FIG. 29. As above, the system may use knowledge of the target material for the restoration to automatically alter the design and design parameters. For example, a semi-precious coping may be xx mm thick, whereas a precious gold coping may be yy mm thick, and the system may automatically assign these thicknesses. In another example, porcelain layers for pressing may vary from vendor to vendor and from specific material formulation to another, and, again, the system may automatically compensate for these differences. The design may also be automatically altered to compensate for different fabrication techniques, e.g. additive RP resin, laser sintering, milling of zirconium/other ceramics/metal.

10. Attachments Library

Figure 30:
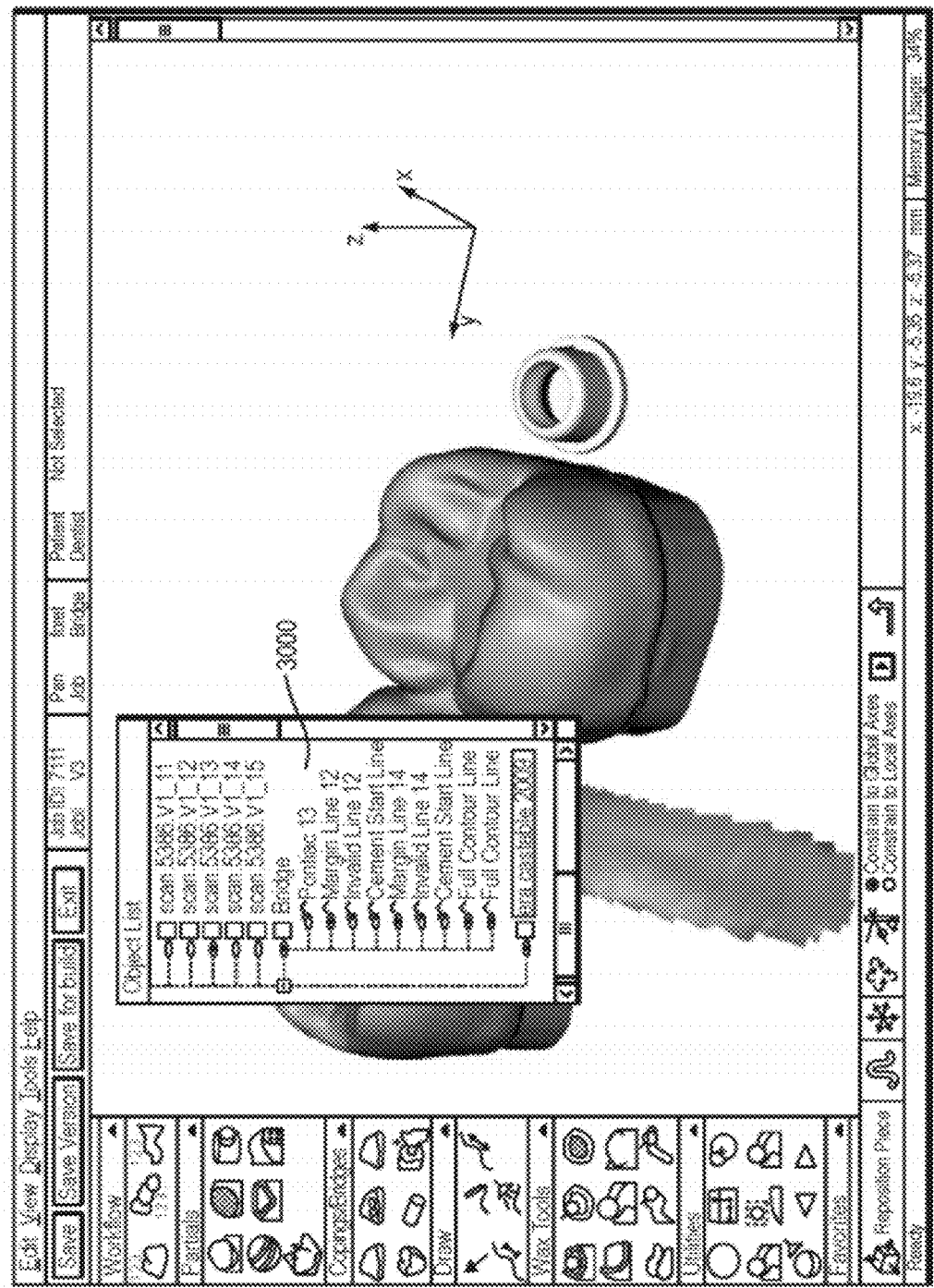
FIG. 30 illustrates a screen capture of an attachments library in accordance with one embodiment of the invention.

FIG. 30 illustrates one embodiment of an attachments library 3000 that includes a first element that is fixed to an existing tooth structure and a second element. The second element may be selected by a technician, added to the partial framework design, output as a plastic resin, and then cast. Rather than providing a mated pair, embodiments of the current invention provide a unisexual attachment system where one member is specified as virtual design wax.

The attachment part may be stored in a virtual parts library. These parts may be placed in the system to automatically line up with a path of insertion or any other orientation to ensure the proper alignment. A user may place two or more attachments to be aligned in parallel, thereby allowing the restoration to be inserted and removed without binding. Using haptics, the virtual attachment part may be automatically constrained to a desired orientation, e.g. path of insertion, to speed the design and accuracy of the finished restoration.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims. Insofar as this is a provisional application, what is considered applicants' invention is not necessarily limited to embodiments that fall within the claims below.

What is claimed is:

1. A system for building a virtual wax object corresponding to a three-dimensional dental restoration, the system comprising:
    a user interface configured to receive input from a user; and
    a design application in communication with the user interface, wherein the design application comprises:
        a design module configured to produce a virtual refractory model, the virtual refractory model comprising (a) an initial 3D computer model created from a scan of a dental stone or created from a scan of a patient's mouth, and (b) virtual block-out wax added to fill in undercuts of the initial 3D computer model and, optionally, a defective portion of the initial 3D computer model; and
        one or more virtual wax-up tools configured to build the virtual wax object corresponding to the three-dimensional dental restoration onto the virtual refractory model according to user input via the user interface, wherein the undercuts are automatically identified based at least in part on a geometry of the initial 3D computer model and a direction of insertion of the three-dimensional dental restoration, wherein the virtual block-out wax is added automatically via a processor or semi-automatically via the user interface, and wherein components (a) and (b) of the virtual refractory model are separately stored volumes that are combined with a volumetric union operation to produce the virtual refractory model.

2. The system of claim 1, wherein the virtual wax object is predominately voxel based, and has a boundary representation geometry near a margin line.

3. The system of claim 1, wherein the one or more virtual wax-up tools comprises one or more members selected from the group consisting of a virtual mesh tool, a virtual ridge tool, a virtual clasp tool, a virtual finish line tool, and a virtual lingual collar tool.

4. The system of claim 1, wherein the one or more virtual wax-up tools comprises a virtual mesh tool.

5. The system of claim 4, wherein the virtual mesh tool builds a three-dimensional patterned mesh portion of the virtual wax object within an arbitrary, user-identified region of a surface of the virtual refractory model with minimal distortion.

6. The system of claim 5, wherein the virtual mesh tool splits a user-defined closed loop curve fit to the surface of the virtual refractory model into four boundary curves within which a NURBS patch is fit.

7. The system of claim 5, wherein the virtual mesh tool further builds a spacer volume of a user-defined thickness, along with the three-dimensional patterned mesh portion.

8. The system of claim 1, wherein the one or more virtual wax up tools comprises a virtual ridge tool.

9. The system of claim 8, wherein the virtual ridge tool builds a long extruded wax pattern with a profile and end taper characteristic suitable for creation of clasps and finish lines around a mesh areas in a partial framework.

10. The system of claim 8, wherein the virtual ridge tool accepts as input one or more guide curves, one or more cross-sectional profiles, and one or more end taper parameters determined by the user.

11. The system of claim 10, wherein the one or more guide curves, one or more cross-sectional profiles, and one or more end taper parameters are selected by the user from a system-wide preferences database.

12. The system of claim 10, wherein the user interface is a haptic interface device configured to provide force feedback to the user and wherein the virtual ridge tool comprises one or more haptic aids delivered to the user via the haptic interface device to assist the user in creating and/or editing the one or more guide curves, the one or more cross-sectional profiles, or both.

13. The system of claim 12, wherein the one or more haptic aids comprises a haptic snap corresponding to each of a plurality of points of the one or more guide curves, facilitating selection of one or more points of the one or more guide curves by the user for adjustment.

14. The system of claim 13, wherein the one or more haptic aids comprises a two-dimensional restriction plane, facilitating selection and adjustment of profile points and/or handles of the one or more cross-sectional profiles.

15. The system of claim 1, wherein the one or more virtual wax up tools comprises a virtual clasp tool.

16. The system of claim 15, wherein the virtual clasp tool builds a simple ring clasp, a J-shaped clasp, or a T-shaped clasp based on one or more user-selected guide curves, profiles, and parameters defining end taper conditions.

17. The system of claim 1, wherein the one or more virtual wax up tools comprises a virtual finish line tool.

18. The system of claim 1, wherein the one or more virtual wax up tools comprises a virtual lingual collar tool.

19. The system of claim 1, wherein the user interface is a haptic interface device configured to provide force feedback to the user and wherein the haptic interface device comprises a stylus interface.

20. The system of claim 1, wherein the user interface is a haptic interface device configured to provide force feedback to the user and wherein the haptic interface device has at least six degrees of freedom.

21. The system of claim 1, wherein the dental restoration is a member selected from the group consisting of a partial framework, crown and bridge, implant, veneer, night guard, bite splint, and orthodonture.

22. The system of claim 1, wherein the design application further comprises a graphical user interface comprising a plurality of icons representing a plurality of virtual tools.

23. The system of claim 1, wherein the design module is configured to allow manual adjustment of the virtual block-out wax.

24. The system of claim 1, wherein the one or more virtual wax-up tools comprises one or more members selected from the group consisting of:
   a virtual mesh tool configured to build a three-dimensional patterned mesh portion of the virtual wax object within an arbitrary, user-identified region of a surface of the virtual refractory model with minimal distortion;
   a virtual ridge tool configured to build a long extruded wax pattern with a profile and end taper characteristic suitable for creation of clasps and finish lines around mesh areas in a partial framework;
   a virtual clasp tool configured to build a simple ring clasp, a J-shaped clasp, or a T-shaped clasp based on one or more user-selected guide curves, profiles, and parameters defining end taper conditions.

25. A method for designing a three-dimensional dental restoration, the method comprising the steps of:
   (a) creating an initial 3D computer model from a scan of a dental stone made from an impression of a patient's mouth, or, alternatively, creating the initial 3D computer model from a direct scan of the patient's mouth;
   (b) automatically adding virtual block-out wax via a processor, or semi-automatically adding virtual block-out wax via a user interface, to an undercut portion of the initial 3D computer model based at least in part on a geometry of the initial 3D computer model and a direction of insertion of the three-dimensional dental restoration,
   (c) joining the initial 3D computer model and the added virtual block-out wax, thereby forming a virtual refractory model, wherein the initial 3D computer model and the added virtual block-out wax of the virtual refractory model are separately stored volumes that are combined with a volumetric union operation to produce the virtual refractory model;
   (d) adding virtual design wax onto the virtual refractory model to define a final 3D computer model of the dental restoration;
   wherein the undercut portion is automatically identified based at least in part on the geometry of the initial 3D computer model and the direction of insertion of the three-dimensional dental restoration.

26. The method of claim 25, further comprising the step of adding virtual relief wax.

27. The method of claim 26, wherein the virtual relief wax is added automatically.

28. The method of claim 26, wherein the virtual relief wax is added manually.

29. The method of claim 26, wherein the virtual relief wax corrects one or more scanning errors in the scan of the dental stone and/or prevents one or more fit errors that may arise during casting of the dental restoration, and wherein the one or more scanning errors are caused by bubbles and/or holes in the dental stone and wherein the one or more fit errors are caused by high frequencies and/or hard corners in the dental stone.

30. The method of claim 25, comprising automatically identifying a user-adjustable margin line.

31. The method of claim 25, wherein at least one step is performed using a haptic interface device configured to provide force feedback to a user.

32. The method of claim 31, wherein the haptic interface device comprises a stylus.

33. The method of claim 31, wherein the haptic interface device comprises at least six degrees of freedom.

34. The method of claim 25, wherein step (d) comprises using one or more virtual wax-up tools selected from the group consisting of a clone tool, a major connector tool, a mesh tool, a ridge tool, a clasp tool, a finish tool, and a lingual collar tool.

35. The method of claim 25, wherein the final 3D computer model comprises a voxel-based representation and a boundary representation.

36. The method of claim 35, wherein the boundary representation improves precision of an identified margin line and cement gap.

37. The method of claim 25, comprising manually adjusting the block-out wax on the undercut portion of the initial 3D computer model.

38. The method of claim 25, comprising manufacturing the three-dimensional dental restoration using the final 3D computer model of the dental restoration.

39. An apparatus for preparing a virtual refractory model in a design of a three-dimensional dental restoration, the apparatus comprising:
   (a) memory that stores code defining a set of instructions; and
   (b) a processor that executes said instructions thereby to:
      (i) create an initial 3D computer model from a scan of a dental stone or a patient situation;
      (ii) automatically add virtual block-out wax via a processor, or semi-automatically add virtual block-out wax via a user interface, to an undercut portion of the initial 3D computer model based at least in part on a geometry of the initial 3D computer model and a direction of insertion of the three-dimensional dental restoration; and
      (iii) update the initial 3D computer model to incorporate the added virtual block-out wax upon a user command, thereby preparing a virtual refractory model onto which a virtual wax object corresponding to the three-dimensional dental restoration can be built, wherein the initial 3D computer model and the added virtual block-out wax of the virtual refractory model are separately stored volumes that are combined with a volumetric union operation to produce the virtual refractory model, wherein the undercut portion is automatically identified based at least in part on the geometry of the initial 3D computer model and the direction of insertion of the three-dimensional dental restoration.

40. The apparatus of claim 39, wherein the processor executes said instructions, before the step (ii) of adding virtual block-out wax, to modify the initial 3D computer model by carving or smoothing bubble artifacts or by ditching a prepared teeth.

41. The apparatus of claim 39, wherein the processor executes said instructions, before the step (iii) of updating the initial 3D computer model, to add virtual relief wax to the scan of the dental stone and/or the initial 3D computer model created from the scan of the dental stone to correct one or more errors due to scanning and/or casting the dental stone.

42. The apparatus of claim 41, wherein the one or more errors are caused by bubbles, holes, high frequencies, and/or hard corners in the dental stone.

43. The apparatus of claim 39, wherein the processor executes said instructions to automatically add virtual relief wax.

44. The apparatus of claim 39, wherein the processor executes said instructions to enable manual addition of virtual relief wax by a user.

45. The apparatus of claim 39, wherein the initial 3D computer model is a multi-representational model including a voxel-based representation and a boundary representation.

46. The apparatus of claim 39, wherein the three-dimensional dental restoration is a member selected from the group consisting of a partial framework, crown, coping, bridge framework, implant, veneer, night guard, bite splint, and orthodonture.

47. The apparatus of claim 39, wherein the virtual refractory model comprises a first volume component corresponding to the scan of the dental stone or the patient situation and a second, separate volume component corresponding to a volume of the virtual block-out wax added to the model.

48. The apparatus of claim 47, wherein the processor executes said instructions to further create a virtual wax object corresponding to the three-dimensional dental restoration, wherein the virtual wax object is built onto the virtual refractory model.

49. The apparatus of claim 48, wherein the virtual wax object is a multi-representational model including a voxel-based representation and a boundary representation.

50. The apparatus of claim 39, wherein the user command comprises activation of a button.

51. The apparatus of claim 39, wherein the processor executes said instructions to automatically identify and display the undercut portion of the initial 3D computer model graphically on a graphical interface based at least in part on the direction of insertion, thereby distinguishing the undercut portion from a non-undercut portion of the initial 3D computer model, wherein the direction of insertion is user-selected.

52. The apparatus of claim 51, wherein the undercut portion is displayed with contrasting colors based on degree of undercut.

53. The apparatus of claim 51, wherein the processor executes said instructions to display said initial 3D computer model in real time as the user adds virtual block-out wax via the user interface, wherein a reduction of the undercut portion is displayed to the user in real time as the user adds virtual block-out wax.

54. The apparatus of claim 39, wherein the processor executes said instructions to create a jagged understructure in the virtual refractory model.

55. The apparatus of claim 39, wherein the processor executes said instructions to apply a set of preferences to the virtual refractory model based on one or more parameters specified by a user.

56. The apparatus of claim 55, wherein the one or more parameters comprises or corresponds to patient data and/or a material to be used in the dental restoration.

57. The apparatus of claim 39, wherein the processor executes said instructions to enable manual adjustment of the block-out wax on the undercut portion of the initial 3D model.

* * * * *